(12) United States Patent
Sherman et al.

(10) Patent No.: US 7,732,491 B2
(45) Date of Patent: Jun. 8, 2010

(54) TREATMENT OF BREAST CANCER WITH A PARP INHIBITOR ALONE OR IN COMBINATION WITH ANTI-TUMOR AGENTS

(75) Inventors: Barry M. Sherman, Hillsborough, CA (US); Charles Bradley, Half Moon Bay, CA (US); Valeria S. Ossovskaya, San Francisco, CA (US)

(73) Assignee: BiPar Sciences, Inc., Brisbane, CA (US)

( * ) Notice: Subject to any disclaimer, the term of this patent is extended or adjusted under 35 U.S.C. 154(b) by 0 days.

(21) Appl. No.: 12/269,024

(22) Filed: Nov. 11, 2008

(65) Prior Publication Data

US 2009/0131529 A1    May 21, 2009

Related U.S. Application Data

(60) Provisional application No. 60/987,333, filed on Nov. 12, 2007, provisional application No. 61/012,364, filed on Dec. 7, 2007, provisional application No. 61/058,528, filed on Jun. 3, 2008.

(51) Int. Cl.
*A61K 31/166* (2006.01)
(52) U.S. Cl. .................................................. 514/619
(58) Field of Classification Search .................. 514/619
See application file for complete search history.

(56) References Cited

U.S. PATENT DOCUMENTS

| | | | |
|---|---|---|---|
| 2,006,735 A | 7/1935 | Fischer at al. | |
| 2,669,583 A | 2/1954 | Clinton et al. | |
| 2,937,204 A | 5/1960 | Harris at al. | |
| 3,161,564 A | 12/1964 | Morehouse | |
| 3,228,833 A | 1/1966 | Crounse at al. | |
| 4,604,463 A | 8/1986 | Miyasaka et al. | |
| 5,032,617 A | 7/1991 | Lee et al. | |
| 5,041,653 A | 8/1991 | Lee et al. | |
| 5,162,532 A | 11/1992 | Comins et al. | |
| 5,177,075 A | 1/1993 | Suto et al. | |
| 5,191,082 A | 3/1993 | Comins et al. | |
| 5,200,524 A | 4/1993 | Comins et al. | |
| 5,215,738 A | 6/1993 | Lee et al. | |
| 5,223,608 A | 6/1993 | Chou et al. | |
| 5,232,735 A | 8/1993 | Kurtz et al. | |
| 5,243,050 A | 9/1993 | Comins et al. | |
| 5,247,089 A | 9/1993 | Comins et al. | |
| 5,262,564 A | 11/1993 | Kun et al. | |
| 5,283,352 A | 2/1994 | Bäckström et al. | |
| 5,321,140 A | 6/1994 | Comins et al. | |
| 5,420,319 A | 5/1995 | Okamoto et al. | |
| 5,434,254 A | 7/1995 | Chou et al. | |
| 5,464,871 A | 11/1995 | Kun et al. | |
| 5,473,074 A | 12/1995 | Kun et al. | |
| 5,482,833 A | 1/1996 | Pero et al. | |
| 5,482,975 A | 1/1996 | Kun et al. | |
| 5,484,951 A | 1/1996 | Kun et al. | |
| 5,516,941 A | 5/1996 | Kun et al. | |
| 5,519,053 A | 5/1996 | Kun et al. | |
| 5,583,155 A | 12/1996 | Kun et al. | |
| 5,631,038 A | 5/1997 | Kurtz et al. | |
| 5,631,231 A | 5/1997 | Kurtz et al. | |
| 5,631,232 A | 5/1997 | Kurtz et al. | |
| 5,631,240 A | 5/1997 | Kurtz et al. | |
| 5,631,252 A | 5/1997 | Kurtz et al. | |
| 5,631,272 A | 5/1997 | Kurtz et al. | |
| 5,631,292 A | 5/1997 | Kurtz et al. | |
| 5,631,294 A | 5/1997 | Kurtz et al. | |
| 5,631,295 A | 5/1997 | Kurtz et al. | |
| 5,631,299 A | 5/1997 | Kurtz et al. | |
| 5,633,282 A | 5/1997 | Collins et al. | |
| 5,637,618 A | 6/1997 | Kurtz et al. | |
| 5,639,788 A | 6/1997 | Kurtz et al. | |
| 5,641,795 A | 6/1997 | Kurtz et al. | |
| 5,641,799 A | 6/1997 | Kurtz et al. | |
| 5,641,811 A | 6/1997 | Kurtz et al. | |
| 5,641,812 A | 6/1997 | Kurtz et al. | |
| 5,643,894 A | 7/1997 | Kurtz et al. | |
| 5,643,941 A | 7/1997 | Kurtz et al. | |
| 5,643,945 A | 7/1997 | Kurtz et al. | |
| 5,643,955 A | 7/1997 | Kurtz et al. | |
| 5,643,956 A | 7/1997 | Kurtz et al. | |
| 5,646,122 A | 7/1997 | Kurtz et al. | |

(Continued)

FOREIGN PATENT DOCUMENTS

CN    1768732 A    5/2006

(Continued)

OTHER PUBLICATIONS

Dent et al. Clin. Cancer Res., 2007, vol. 13, No. 15, pp. 4429-4434.*
Cleator et al. Lancet Oncol., 2007, vol. 8, pp. 235-244.*
Irvin et al. European Journal of Cancer, 2008, vol. 44, pp. 2799-2805.*
De Soto et al. International Journal of Medical Sciences, 2006, vol. 3, No. 4, pp. 117-123.*
Donawho et al. Clin. Cancer Res., 2007, vol. 13, No. 9, pp. 2728-2737.*
Ausubel, et al. Current Protocols of Molecular Biology, John Wiley and Sons (1997).
Ayhan, et. al. Topotecan as a second-line therapy in patients with ovarian and primary peritoneal cancer: initial response and long-term follow-up. Eur J Gynaecol Oncol. 2006;27(6):603-6.
Berchuck, et al. Overexpression of HER-2/neu in endometrial cancer is associated with advanced stage disease. Am J Obstet Gynecol. Jan. 1991;164(1 Pt 1):15-21.

(Continued)

*Primary Examiner*—James D Anderson
(74) *Attorney, Agent, or Firm*—Morrison & Foerster LLP

(57) ABSTRACT

In one aspect, the present invention provides a method of treating breast cancer that is negative for at least one of ER, PR, or HER2, comprising administering to a subject at least one PARP inhibitor. In another aspect, the present invention provides a method of treating breast cancer comprising administering to a subject at least one PARP inhibitor in combination with at least one anti-tumor agent.

10 Claims, 6 Drawing Sheets

U.S. PATENT DOCUMENTS

| | | | |
|---|---|---|---|
| 5,650,403 | A | 7/1997 | Kurtz et al. |
| 5,652,260 | A | 7/1997 | Kun et al. |
| 5,652,367 | A | 7/1997 | Kun et al. |
| 5,654,311 | A | 8/1997 | Kurtz et al. |
| 5,665,755 | A | 9/1997 | Kurtz et al. |
| 5,670,518 | A | 9/1997 | Kun et al. |
| 5,700,792 | A | 12/1997 | Kurtz et al. |
| 5,703,053 | A | 12/1997 | Kurtz et al. |
| 5,719,151 | A | 2/1998 | Shall et al. |
| 5,734,056 | A | 3/1998 | Burk et al. |
| 5,736,576 | A | 4/1998 | Kun et al. |
| 5,753,674 | A | 5/1998 | Kun et al. |
| 5,756,510 | A | 5/1998 | Griffin et al. |
| 5,770,599 | A | 6/1998 | Gibson |
| 5,783,599 | A | 7/1998 | Kun et al. |
| 5,837,729 | A | 11/1998 | Bourinbaiar |
| 5,866,608 | A | 2/1999 | Kurtz et al. |
| 5,874,444 | A | 2/1999 | West |
| 5,877,185 | A | 3/1999 | Kun et al. |
| 5,908,861 | A | 6/1999 | Kun |
| 5,922,775 | A | 7/1999 | Kun et al. |
| 5,959,133 | A | 9/1999 | Ohnishi |
| 6,004,978 | A | 12/1999 | Kun et al. |
| 6,008,250 | A | 12/1999 | Kurtz et al. |
| 6,015,792 | A | 1/2000 | Kurtz et al. |
| 6,015,827 | A | 1/2000 | Griffin et al. |
| 6,017,958 | A | 1/2000 | Kun et al. |
| 6,100,283 | A | 8/2000 | Griffin et al. |
| 6,121,278 | A | 9/2000 | Jackson et al. |
| 6,156,739 | A | 12/2000 | Griffin et al. |
| 6,169,104 | B1 | 1/2001 | Tusé et al. |
| 6,201,020 | B1 | 3/2001 | Zhang et al. |
| 6,235,748 | B1 | 5/2001 | Li et al. |
| 6,277,990 | B1 | 8/2001 | Jagtap et al. |
| 6,303,629 | B1 | 10/2001 | Kun |
| 6,310,082 | B1 | 10/2001 | Griffin et al. |
| 6,316,455 | B1 | 11/2001 | Griffin et al. |
| 6,316,495 | B1 | 11/2001 | Kun et al. |
| 6,326,517 | B1 | 12/2001 | Kume et al. |
| 6,380,193 | B1 | 4/2002 | Li et al. |
| 6,387,902 | B1 | 5/2002 | Zhang et al. |
| 6,395,749 | B1 | 5/2002 | Li et al. |
| 6,407,079 | B1 | 6/2002 | Müller et al. |
| 6,423,696 | B1 | 7/2002 | Collins et al. |
| 6,426,415 | B1 | 7/2002 | Jackson et al. |
| 6,448,271 | B1 | 9/2002 | Lubisch et al. |
| 6,476,048 | B1 | 11/2002 | Szabo et al. |
| 6,495,541 | B1 | 12/2002 | Webber et al. |
| 6,514,983 | B1 | 2/2003 | Li et al. |
| 6,548,494 | B1 | 4/2003 | Webber et al. |
| 6,664,269 | B2 | 12/2003 | Martin et al. |
| 6,677,333 | B1 | 1/2004 | Seko et al. |
| 6,723,733 | B2 | 4/2004 | Li et al. |
| 6,903,098 | B1 | 6/2005 | Lubisch et al. |
| 6,924,284 | B2 | 8/2005 | Beaton et al. |
| 6,989,388 | B2 | 1/2006 | Pellicciari et al. |
| 7,179,484 | B2 | 2/2007 | Singh |
| RE39,608 | E | 5/2007 | Lubisch et al. |
| 7,405,227 | B2 * | 7/2008 | Kun et al. ............ 514/309 |
| 7,538,252 | B2 | 5/2009 | Ossovskaya et al. |
| 2002/0028815 | A1 | 3/2002 | Ator et al. |
| 2002/0156050 | A1 | 10/2002 | Li et al. |
| 2002/0164633 | A1 | 11/2002 | Szabo et al. |
| 2004/0034078 | A1 | 2/2004 | Skalitzky et al. |
| 2004/0077667 | A1 | 4/2004 | Matsuoka et al. |
| 2004/0198693 | A1 | 10/2004 | DeNinno et al. |
| 2004/0248879 | A1 | 12/2004 | Canan-Koch et al. |
| 2004/0249841 | A1 | 12/2004 | Cameron et al. |
| 2005/0020595 | A1 | 1/2005 | Kalish et al. |
| 2005/0026933 | A1 | 2/2005 | Greenberger et al. |
| 2005/0054631 | A1 | 3/2005 | Jiang et al. |
| 2005/0059824 | A1 | 3/2005 | Vaidyanathan et al. |
| 2005/0080096 | A1 | 4/2005 | Ishida et al. |
| 2005/0113283 | A1 | 5/2005 | Solow-Cordero et al. |
| 2005/0171036 | A1 | 8/2005 | Arakawa et al. |
| 2005/0171101 | A1 | 8/2005 | Yamamoto et al. |
| 2005/0227919 | A1 | 10/2005 | Ashworth et al. |
| 2005/0287120 | A1 | 12/2005 | Fisher et al. |
| 2006/0063767 | A1 | 3/2006 | Javaid et al. |
| 2006/0074073 | A1 | 4/2006 | Steinfeldt et al. |
| 2006/0094676 | A1 | 5/2006 | Lahav et al. |
| 2006/0100198 | A1 | 5/2006 | Liu et al. |
| 2006/0229289 | A1 | 10/2006 | Zhu et al. |
| 2006/0229351 | A1 | 10/2006 | Zhu et al. |
| 2007/0015814 | A1 | 1/2007 | Kun et al. |
| 2007/0265324 | A1 | 11/2007 | Wernet et al. |
| 2007/0281948 | A1 | 12/2007 | Peukert et al. |
| 2007/0292883 | A1 | 12/2007 | Ossovskaya et al. |
| 2008/0025990 | A1 | 1/2008 | Ludwig |
| 2008/0039633 | A1 | 2/2008 | Jung et al. |
| 2008/0076778 | A1 | 3/2008 | Ossovskaya et al. |
| 2008/0103104 | A1 | 5/2008 | Moore et al. |
| 2008/0103208 | A1 | 5/2008 | Ossovskaya et al. |
| 2008/0167345 | A1 | 7/2008 | Jones et al. |
| 2008/0176946 | A1 | 7/2008 | Ossovskaya et al. |
| 2008/0262062 | A1 | 10/2008 | Ossovskaya et al. |
| 2008/0293795 | A1 | 11/2008 | Donawho et al. |
| 2008/0319054 | A1 | 12/2008 | Kun et al. |
| 2009/0076122 | A1 | 3/2009 | Kun et al. |
| 2009/0123419 | A1 | 5/2009 | Sherman et al. |
| 2009/0149397 | A1 | 6/2009 | Ossovskaya et al. |
| 2009/0149417 | A1 | 6/2009 | Ossovskaya et al. |
| 2009/0291924 | A1 | 11/2009 | Ossovskaya et al. |

FOREIGN PATENT DOCUMENTS

| | | | |
|---|---|---|---|
| CN | 1768732 | A | 5/2006 |
| CN | 1768733 | A | 5/2006 |
| CN | 1768733 | A | 5/2006 |
| CN | 101190211 | A | 6/2008 |
| CN | 101190211 | A | 6/2008 |
| EP | 0 841 924 | B1 | 5/1998 |
| EP | 1 127 052 | B1 | 8/2001 |
| EP | 1 348 432 | A1 | 10/2003 |
| EP | 1082416 | B1 | 3/2007 |
| FR | 2 456 731 | A | 1/1971 |
| GB | 1 463 575 | | 2/1977 |
| GB | 2 447 796 | B | 3/2009 |
| JP | 2000/191612 | A | 7/2000 |
| JP | 2005/336083 | A | 12/2005 |
| WO | WO-91/18591 | A1 | 12/1991 |
| WO | WO-94/05664 | A1 | 3/1994 |
| WO | WO 94/10202 | A1 | 5/1994 |
| WO | WO-94/26730 | A2 | 11/1994 |
| WO | WO-94/26730 | A3 | 11/1994 |
| WO | WO 94/27584 | A2 | 12/1994 |
| WO | WO 94/27584 | A3 | 5/1995 |
| WO | WO-96/22791 | A1 | 8/1996 |
| WO | WO 96/40210 | A1 | 12/1996 |
| WO | WO-97/34593 | A1 | 9/1997 |
| WO | WO-92/06687 | A1 | 10/1997 |
| WO | WO-98/45253 | A1 | 10/1998 |
| WO | WO-99/11624 | A1 | 3/1999 |
| WO | WO-99/11628 | A1 | 3/1999 |
| WO | WO-01/04086 | A1 | 1/2001 |
| WO | WO-02/49992 | A2 | 6/2002 |
| WO | WO-02/49992 | A3 | 6/2002 |
| WO | WO 03/007955 | A2 | 1/2003 |
| WO | WO 03/007955 | A3 | 5/2003 |
| WO | WO-03/062392 | A2 | 7/2003 |
| WO | WO-03/062392 | A3 | 7/2003 |
| WO | WO-2005/012305 | A2 | 2/2005 |
| WO | WO-2005/012305 | A3 | 2/2005 |
| WO | WO-2005/054201 | A1 | 6/2005 |

| | | |
|---|---|---|
| WO | WO-2005/054209 A1 | 6/2005 |
| WO | WO-2005/054210 A1 | 6/2005 |
| WO | WO-2005/058843 A1 | 6/2005 |
| WO | WO-2005/058843 C1 | 6/2005 |
| WO | WO-2005/097750 A1 | 10/2005 |
| WO | WO-2006/003146 A1 | 1/2006 |
| WO | WO-2006/003147 A1 | 1/2006 |
| WO | WO-2006/003148 A1 | 1/2006 |
| WO | WO-2006/003150 A1 | 1/2006 |
| WO | WO 2006/020681 A2 | 2/2006 |
| WO | WO 2006/046735 A1 | 5/2006 |
| WO | WO 2006/067472 A1 | 6/2006 |
| WO | WO 2006/020681 A3 | 12/2006 |
| WO | WO-2007/011962 A2 | 1/2007 |
| WO | WO-2007/011962 A3 | 1/2007 |
| WO | WO 2007/107305 A2 | 9/2007 |
| WO | WO 2007/107305 A3 | 11/2007 |
| WO | WO-2008/030883 A2 | 3/2008 |
| WO | WO-2008/089272 A1 | 7/2008 |
| WO | WO 2008/107478 A1 | 9/2008 |
| WO | WO-2008/147418 A1 | 12/2008 |
| WO | WO-2009/064444 A2 | 5/2009 |
| WO | WO-2009/064738 A2 | 5/2009 |
| WO | WO-2009/073869 A1 | 6/2009 |

OTHER PUBLICATIONS

Bigler, et.al. Evaluation of tamoxifen in persistent or recurrent nonsquamous cell carcinoma of the cervix: a Gynecologic Oncology Group study. Int J Gynecol Cancer. Sep.-Oct. 2004;14(5):871-4.

Bouchard, et.al. PARP-1, a determinant of cell survival in response to DNA damage. Exp Hematol. Jun. 2003;31(6):446-54.

Bryant, et al. Specific killing of BRCA2-deficient tumours with inhibitors of poly(ADP-ribose) polymerase. Nature. 2005;434:913-917.

Chakraborty, et.al. Co-targeting insulin-like growth factor I receptor and HER2: dramatic effects of HER2 inhibitors on nonoverexpressing breast cancer. Cancer Res. Mar. 1, 2008;68(5):1538-45.

Classen, et al. Structure of the topoisomerase II ATPase region and its mechanism of inhibition by the chemotherapeutic agent ICRF-187. Proc Natl Acad Sci U S A. Sep. 16, 2003;100(19):10629-34. and Erratum.

D'Amours, et al. Poly (ADP-ribosyl)ation reactions in the regulation of nuclear functions. *Biochem J.* 1999; 342: 249-268.

de Murcia, et al. Requirement of poly(ADP-ribose) polymerase in recovery from DNA damage in mice and in cells. Proc Natl Acad Sci U S A. Jul. 8, 1997;94(14):7303-7.

Drew, et al. The potential of PARP inhibitors in genetic breast and ovarian cancers. Ann N Y Acad Sci. Sep. 2008;1138:136-45.

Farmer, et.al. Targeting the DNA repair defect in BRCA mutant cells as a therapeutic strategy. Nature. Apr. 14, 2005;434(7035):917-21.

Fisher, et al. Endometrial cancer in tamoxifen-treated breast cancer patients: findings from the National Surgical Adjuvant Breast and Bowel Project (NSABP) B-14. J Natl Cancer Inst 1994; 86:527-37.

Gudmundsdottir, et al. The roles of BRCA1 and BRCA2 and associated proteins in the maintenance of genomic stability. Oncogene. Sep. 25, 2006;25(43):5864-74.

Gurpide, E. Endometrial Cancer: Biochemical and Clinical Correlates. J Natl Cancer Inst 1991;83(6): 405-416.

Helleday, et al. DNA repair pathways as targets for cancer therapy. Nat Rev Cancer. Mar. 2008;8(3):193-204.

Hellstrom, et.al. Overexpression of HER-2 in ovarian carcinomas. Cancer Res. Mar. 15, 2001;61(6):2420-3.

Herceg, et al. Functions of poly(ADP-ribose) polymerase (PARP) in DNA repair, genomic integrity and cell death. Mutat Res. Jun. 2, 2001;477(1-2):97-110.

Hod, Y. A simplified ribonuclease protection assay. Biotechniques. Dec. 1992;13(6):852-4.

Jones, et al. PARP inhibitors and cancer therapy—early results and potential applications. Br J Radiol. Oct. 2008;81 Spec No. 1:S2-S5.

Khalid, et al. Long circulating poly(ethylene glycol)-decorated lipid nanocapsules deliver docetaxel to solid tumors. Pharm Res. Apr. 2006;23(4):752-8.

Kurman, R. Ed. Blaustein's Pathology of the Female Genital Tract. 5th ed. Springer-Verlag. New-York 2002. (Cover pages/table of contents only).

Leslie, et al. Tyrosine kinase inhibitors in endometrial cancer. International Journal of Gynecological Cancer. 2005;15:409-411.

McCabe et al. Deficiency in the repair of DNA damage by homologous recombination and sensitivity to poly(ADP-ribose) polymerase inhibition. Cancer Res. Aug. 15, 2006;66(16):8109-15.

Narod, et al. BRCA1 and BRCA2: 1994 and beyond. Nat Rev Cancer. Sep. 2004;4(9):665-76.

Nitta, et al. Antitumor activity of new derivatives of camptothecin. Gan To Kagaku Ryoho. Mar. 1987;14(3 Pt 2):850-7. (in Japanese with English abstract).

Normura, et al. Enhancement of poly-adenosine diphosphate-ribosylation in human hepatocellular carcinoma. J Gastroenterol Hepatol. May 2000;15(5):529-35.

Parker, et al. mRNA: detection by in Situ and northern hybridization. Methods Mol Biol. 1999;106:247-83.

Rice, et al. Induction of Endonuclease-Mediated Apoptosis in Tumor Cells by C-Nitroso- Substituted Ligands of Poly(ADP-Ribose) Polymerase. Proceedings of the National Academy of Sciences. 1992; 89:7703-7707.

Rottenberg, et al. High sensitivity of BRCA1-deficient mammary tumors to the PARP inhibitor AZD2281 alone and in combination with platinum drugs. Proc Natl Acad Sci U S A. Nov. 4, 2008;105(44):17079-84.

Schreiber, et al. Poly(ADP-ribose): novel functions for an old molecule. Nat Rev Mol Cell Biol. Jul. 2006;7(7):517-28.

Serr, et al. NVP-BEZ235, a dual PI3K/mTOR inhibitor, prevents PI3K signaling and inhibits the growth of cancer cells with activating PI3K mutations. Cancer Res. Oct. 1, 2008;68(19):8022-30.

Shah, et al. Selenium disrupts estrogen receptor (alpha) signaling and potentiates tamoxifen antagonism in endometrial cancer cells and tamoxifen-resistant breast cancer cells. Mol Cancer Ther. 2005;4(8):1239-49.

Simon, R. Optimal two-stage designs for phase II clinical trials. Control Clin Trials. Mar. 1989;10(1):1-10.

Singh, N. Enhanced poly ADP-ribosylation in human leukemia lymphocytes and ovarian cancers. Cancer Lett. Jun. 14, 1991;58(1-2):131-5.

Wang, et al. PARP is important for genomic stability but dispensable in apoptosis. Genes Dev. Sep. 15, 1997;11(18):2347-58.

Weis, et al. Detection of rare mRNAs via quantitative RT-PCR. Trends Genet. Aug. 1992;8(8):263-4.

Yalcintepe, et al. Changes in NAD/ADP-ribose metabolism in rectal cancer. Braz J Med Biol Res. Mar. 2005;38(3):361-5.

Yanochko, et al. Type I insulin-like growth factor receptor overexpression induces proliferation and anti-apoptotic signaling in a three-dimensional culture model of breast epithelial cells. Breast Cancer Res. 2006;8(2):R18.

Arnone, et al. Nucleophilic substitution reactions of 1-halogeno-4-COR-2-nitrobenzenes and 1-halogeno-6-COR-2 nitrobenzenes with sodium benzenethiolate and piperidine. Can an 'inverted built-in solvation' be responsible for the peculiar activation by an o-carboxamido group in SNAr reactions with an anionic nucleophile? J. Org. Chem. 1997; 62(10):3093-3097.

Bauer, et al. Anti-cancer action of 4-iodo-3-nitrobenzamide in combination with buthionine sulfoximine: inactivation of poly(ADP-ribose) polymerase and tumor glycolysis and the appearance of a poly(ADP-ribose) polymerase protease. Biochem. Pharmacol. 2002; 63(3):455-462.

Bauer, et al. The influence of ATP on poly(ADP-ribose) metabolism. Int'l J. Mol. Med. 2005; 16:321-324.

Bentle, et al. New tricks for old drugs: the anticarcinogenic potential of DNA repair inhibitors. J. Mol. Histol. 2006; 37(5-7):203-218.

Cepeda, et al. Poly(ADP-ribose) polymerase-1 (PARP-1) inhibitors in cancer chemotherapy. Rec. Pat. Anti-Cancer Drug Discov. 2006; 1:39-53.

Chu, et al. Poly(ADP-ribose) polymerase-1 regulates vimentin expression in lung cancer cells. Am. J. Physiol.: Lung, Cell. Mol. Physiol. 2007;37(5):L1127-L1134.

Chuang, et al. Comparison of the cytotoxic and antiretroviral effects of 3-nitrosobenzamide and 4-iodo-3-nitrobenzamide. Proc. West. Pharmacol. Soc. 1994;37:117-119.

Cleator, et al. Triple-negative breast Cancer: therapeutic options. Lancet Oncol. 2007; 8:235-244.

Cosi, C. New inhibitors of poly(ADP-ribose) polymerase and their therapeutic targets. Exp. Opin. Therapeut. Pat. 2002;12(7):1047-1071.

Donawho, et al. ABT-888, an orally active poly(ADP-ribose) polymerase inhibitor that potentiates DNA-damaging agents in preclinical tumor models. Clin. Cancer Res. 2007;13:2728-2737.

Filmus, et al. Epidermal growth factor receptor gene-amplified MDA-468 breast cancer cell line and its nonamplified variants. Mol. Cell. Biol. 1987; 7(1):251-257.

Hassa, et al. Nuclear ADP-ribosylation reactions in mammalian cells: where are we today and where are we going? Microbiol. Mol. Biol. Rev. 2006; 70(3):789-829.

Hassa, et al. The enzymatic and DNA binding activity of PARP-1 are not required for NF-kB coactivator function. J. Biol. Chem. 2001; 276(49):45588-45597.

Irvin, Jr. et al. What is triple-negative breast cancer? Eur. J. Cancer. 2008;44:2799-2805.

Jacob, et al. Combination therapy of poly (ADP-ribose) polymerase inhibitor 3-aminobenzamide and gemcitabine shows strong antitumor activity in pancreatic cancer cells. J. Gastroenterol. Hepatol. 2007;22:738-748.

Jagtap, et al. Poly(ADP-ribose) polymerase and the therapeutic effects of its inhibitors. Nature Rev. Drug Disc. 2005;4:421-440.

Kandel, et al. Prevalence of BRCA1 mutations in triple negative breast cancer. J. Clin. Oncol. 2006 ASCO Annual Meeting Proceedings Part I. 24:2006 (Jun. 20 Supplement, Abstract 508).

Kirsten, et al. Cancer cell selectivity of 5-iodo-6-aminobenzopyrone (INH2BP) and methyl 3-5-diiodo-4(4'-methoxyphenol) benzoate (DIME). Int'l J. Mol. Med. 2000; 5(3):279-281.

Kun, et al. Cell biological functions of PARP-1: an overview, Ital. J. Biochem. 2001;50(1-2):15-18.

Kun, et al. Quantitative correlation between cellular proliferation and nuclear poly (ADP-ribose) polymerase (PAPR-1). Int'l J. Mol. Med. 2006;17:293-300.

Kun, et al. Synergistic anticancer action of reversibly and irreversibly acting ligands of poly (ADP-ribose) polymerase. Int'l J. Mol. Med. 2003; 11(2):191-193.

Mendeleyev, et al. Potential chemotherapeutic activity of 4-iodo-3-nitrobenzamide: metabolic reduction to the 3-nitroso derivative and induction of cell death in tumor cells in culture. Biochem. Pharmacol. 1995; 50(5):705-714.

Nguewa, et al. Pharmacological modulation of poly(ADP-ribose) polymerase-mediated cell death: exploitation in cancer chemotherapy. Mol. Pharmacol. 2003; 64(5):1007-1014.

Ramonas, et al. Treatment of Transgenic Murine Retinoblastoma With 4-Iodo-3-Nitrobenzamide. Invest. Ophthalmol. Vis. Sci. 2005; 46(5):E-Abstract 3422.

Ratnam, et al. Current development of clinical inhibitors of poly(ADP-ribose) polymerase in oncology. Clin. Cancer Res. 2007; 13(5):1383-1388.

Reis-Filho, et al. Triple negative tumours: a critical review. Histopathol. 52:108-118 (2008).

Simbulan-Rosenthal, et al. Misregulation of gene expression in primary fibroblasts lacking poly(ADP-ribose) polymerase. Proc. Nat'l Acad. Sci. USA. 2000; 97(21):11274-11279.

Thomas, et al. Preclinical selection of a novel poly(ADP-ribose) polymerase inhibitor for clinical trial, Mol. Cancer Ther. 2007; 6(3):945-956.

Wasseman, et al. Evolving strategies for the treatment of 'triple-negative' breast cancer, American Society of Clinical Oncology Educational Book 2008:120-126 (2008).

Winer, et al. Optimizing treatment of "triple-negative" breast cancer. 30th Annual San Antonio Breast Cancer Symposium (2007). (4 pages).

Byrant, H.E. et al. (Apr. 14, 2005). "Specific Killing of BRCA2-Deficient Tumours with Inhibitors of Poly(ADP-ribose) Polymerase," Nature 447:913-917.

Byrant, H.E. et al. (May 17, 2007). "Specific Killing of BRCA2-Deficient Tumours with Inhibitors of Poly(ADP-ribose) Polymerase," Addendum, Nature 434:346.

Comen, E.A. et al. (May 20, 2008). "Prevalence of BRCA1 and BRCA2 Mutations in Jewish Women with Triple Negative Breast Cancer," Abstract 22002, in ASCO Annual Meeting Proceedings, Part I, May 30-Jun. 3, 2008, Chicago, IL, J. Clin. Oncol. 126(15S):749s and located at <http://www.jco.ascopubs.org/cgi/mgca...>, last accessed on Jun. 14, 2009, eight pages.

Donegan, W.L. et al., eds. (1988). Cancer of the Breast, 3rd Edition, W. B. Saunders: Philadelphia, PA, p. 504.

Aachmann, F. L. et al. (2003). "Structural Background of Cyclodextrin-Protein Interactions," Prot. Eng. 16(12):905-912.

Arnold, N. et al. (May 1996). "Overrepresentation of 3q and 8q Material and Loss of 18q Material Are Recurrent Findings in Advanced Human Ovarian Cancer," Genes Chromosomes Cancer, 16(1):46-54.

Astrazeneca International. Gefitinib (IRESSA™) Lung Cancer ISEL Trial shows no overall survival advantage in a highly refractory population. Press release, Dec. 17, 2004. Available at: http://www.astrazeneca.com/pressrelease/4245.aspx, last visited Oct. 2, 2009.

Audebert, M. et al. (Dec. 31, 2004)."Involvement of Poly(ADP-Ribose) Polymerase-1 and XRCC1/DNA Ligase III in an Alternative Route for DNA Double-Strand Breaks Rejoining," J. Biol. Chem. 279(53):55117-55126. Epub Oct. 21, 2004.

Bale, A. E. et al. (1997). "The Nevoid Basal Cell Carcinoma Syndrome: Genetics and Mechanism of Carcinogenesis," Cancer Invest. 15(2):180-186.

Ball, H. G. et al. (Aug. 1996). "A Phase II Trial of Paclitaxel in Patients With Advanced or Recurrent Adenocarcinoma of the Endometrium: A Gynecologic Oncology Group Study," Gynecologic Oncology 62(2):278-281.

Banasik, M. et al. (1992). "Specific Inhibitors of Poly(ADP-Ribose) Synthetase and Mono(ADP-Ribosyl)Transferase," J. Biol. Chem. 267:1569-1575.

Bangham, A.D., et al. (1965). "Diffusion of Univalent Tons Across the Lamellae of Swollen Phospholipids," J. Mol. Biol. 13:238-252.

Banker, G. S. et al., eds. (1996). Modem Pharmaceutics, Marcel Dekker, New York, 3rd edition, p. 596 and Table of Content (with last page of the book).

Bello, M. J. et al. (Jan. 15, 1990). "Chromosome Aberrations in Metastatic Ovarian Cancer: Relationship With Abnormalities in Primary Tumors," Int. J. Cancer 45(1):50-54.

Ben-Hur, E. et al. (1984). "Inhibitors of Poly (ADP-Ribose) Synthesis Enhance Radiation Response by Differentially Affecting Repair of Potentially Lethal Versus Sublethal Damage," British Journal of Cancer 49:34-42.

Berger, N. (1985). "Poly(ADP-Ribose) in the Cellular Response to DNA Damage," Radiation Research 101:4-14.

Berkow, R. ed., (Aug. 1987). "Chapter 105. Oncology—Treatment and Prognosis," in The Merck Manual of Diagnosis and Therapy, 15th ed. Merck & Co., Inc., pp. 1218-1225 and Table of Contents.

Bhattacharjee, A. et al. (Nov. 20, 2001). "Classification of Human Lung Carcinomas by mRNA Expression Profiling Reveals Distinct Adenocarcinoma Subclasses," Proc. Natl. Acad. Sci. USA 98(24):13790-13795. (Epub. Nov. 13, 2001).

Bonadonna, G. et al. (Jan. 1998). "Primary Chemotherapy in Operable Breast Cancer: Eight-Year Experience at the Milan Cancer Institute," J. Clin. Oncol. 16(1):93-100.

Borczuk, A. C. et al. (Nov. 2003). "Non-Small-Cell Lung Cancer Molecular Signatures Recapitulate Lung Development Pathways," Am. J. Pathol. 163(5):1949-1960.

Buki, K. G. et al. (1991). "Destabilization of $Zn^{2+}$ Coordination in ADP-Ribose Transferase (Polymerizing) by 6-Nitroso-1,2-Benzopyrone Coincidental With Inactivation of the Polymerase but not the DNA Binding Function," FEBS Lett. 290:181-185.

Buki, K.G. et al. (1992). "Inactivation of the Polymerase but not the DNA Binding Function of ADPRT by Destabilization of one of its $Zn^{2+}$ Coordination Centers by 6-Nitroso-1,2-Benzopryone," in ADP-Ribosylation Reactions, Poirier, G.G. et al., eds., Springer-Verlag: New York, NY, pp. 329-333.

Chang, J. W. et al. (May 2000). "Correlation of Genetic Instability With Mismatch Repair Protein Expression and P53 Mutations in Non-Small Cell Lung Cancer," *Clin. Cancer Research* 6(5):1639-1646.

Chang, P. et al. (Dec. 2, 2004). "Poly(ADP-ribose) is Required for Spindle Assembly and Structure," *Nature* 432(7017):645-649.

Chen, X. et al. (1998). "Potential for Selective Modulation of Glutathione in Cancer Chemotherapy," *Chem. Biol. Interact.* 111-112:263-275.

Chen, Q.-R. et al. (2007). "Diagnosis of the Small Round Blue Cell Tumors Using Multiplex Polymerase Chain Reaction," *Journal of Molecular Diagnostics* 9(1):80-88.

Chevallier, B. et al. (1993). "Inflammatory Breast Cancer. Pilot Study of Intensive Chemotherapy (FEC-HD) Results in a High Histologic Response Rate," *Am. J. Clin. Oncol.* 16:223-228.

Chin, K. et al. (Dec. 2006). "Genomic and Transcriptional Aberrations Linked to Breast Cancer Pathophysiologies," *Cancer Cell* 10(6)529-541.

Christie, M. et al. (2006). "Molecular Pathology of Epithelial Ovarian," *Journal of the British Menopause Society* 12(2):57-63.

Chustecka, Z. (Jan. 22, 2007). "Adding Bevacizumab Not Beneficial in Pancreatic Cancer," *Gastrointestinal Cancers Symposium*, presented Jan. 20, 2007, 2 pages.

Clarke, M. J. (Oct. 8, 2008). Early Breast Cancer Trialists' Collaborative Group. "Tamoxifen for Early Breast Cancer," from the *Cochrane Database of Systematic Reviews* Oct. 8, 2008, (4):CD000486. This abstract was available at http://www.cochrane.org/reviews/en/ab000486.html , but is now withdrawn from the Cochrane Database System Review. This abstract was an updated version of Cochrane Database System Review (2001)(1):CD000486. Abstract available in PubMed at http://www.ncbi.nim.nih.gov/pubmed/18843611?ordinalpos=5&itool=EntrezSystem2.PEntrez.Pubmed.Pubmed_ResultsPanel.Pubmed_DefaultReportPanel.Pubmed_RVDoc:Sum, last visited Oct. 2, 2009.

Clinical Trials. US Government (2008). Evaluation of Paclitaxel (Taxol, NSC #673089), Carboplatin (Paraplatin, NSC #241240), and BSI-201 (NSC #746045, IND #71,677) in the Treatment of Advanced, Persistent, or Recurrent Uterine Carcinosarcoma, Verified by BiPar Sciences, Jul. 2009, first received: May 28, 2008 Last Updated: Jul. 23, 2009, located at http://clinicaltrials.gov/ct2/show/NCT00687687, last visited on Sep. 18, 2009.

Cosi, C. et al. (1994). "Poly(ADP-Ribose) Polymerase: Early Involvement in Glutamate-Induced Neurotoxicity in Cultured Cerebellar Granule Cells," *J. Neurosci. Res.* 39:38-46.

Costantino, G. et al. (2001). "Modeling of Poly(ADP-Ribose)Polymerase (PARP) Inhibitors. Docking of Ligands and Quantitative Structure-Activity Relationship Analysis," *J. Med. Chem.* 44(23): 3786-3794.

Crowson, M. C. et al. (Dec. 1986). "A Phase II Study to Evaluate Tamoxifen in Pancreatic Adenocarcinoma," *Eur. J. Surg. Oncol.*. 12(4):33535-33536.

Curtin, J. P. et al. (Nov. 2001). "Paclitaxel in the Treatment of Carcinosarcoma of the Uterus: A Gynecologic Oncology Group Study," *Gynecologic Oncology* 83(2):268-270.

D'Adda Di Fagagna, F. et al. (Sep. 1999). "Functions of Poly(ADP-Ribose) Polymerase in Controlling Telomere Length and Chromosomal Stability," *Nature Genetics* 23(1):76- 80.

Deger, R. B. et al. (Jul. 15, 1997). "Karyotic Analysis of 32 Malignant Epithelial Ovarian Tumors," *Cancer Genet. Cytogenet.* 96(2):166-173.

Delattre, O. et al. (Sep. 10, 1992). "Gene Fusion With an *ETS* DNA-Binding Domain Caused by Chromosome Translocation in Human Tumours," *Nature* 359(6391):162-165.

Delattre, O. et al. (Aug. 4, 1994). "The Ewing Family of Tumors—A Subgroup of Small-Round-Cell Tumors Defined by Specific Chimeric Transcripts," *N. Engl. J. Med.* 331(5):294-299.

De Murcia, G. et al. (Apr. 1994). "Poly(ADP-Ribose) Polymerase: a Molecular Nick-Sensor," *Trends in Biochemical Sciences* 19:172-176.

Desmarais, Y. et al. (Jun. 24, 1991). "Enzymological Properties of Poly(ADP-Ribose)Polymerase: Characterization of Automodification Sites and NADase Activity," *Biochim. Biophys. Acta.* 1078(2):179-186.

De Soto, J. et al. (2006). "The Inhibition and Treatment of Breast Cancer with Poly (ADP-Ribose) Polymerase (PARP-1) Inhibitors," *Int. J. Biol. Sci.* 2(4):179-185.

Diebold, J. et al. (Apr. 2000). "20q13 and Cyclin D1 in Ovarian Carcinomas. Analysis by Fluorescence in Situ Hybridization," *J. Pathol.*, 190(5):564-571.

Donawho, C. K. et al. (2008). "The PARP Inhibitor, ABT-888 Overcomes Resistance in Temozolomide-Refractory Prostate and Breast Xenograft Tumors Implanted in Metastatic Sites In Vivo," Meeting Poster No. 555 (one page), and Palma, J. et al. (Oct. 24, 2008). "The PARP Inhibitor, ABT-888 Overcomes Resistance in Temozolomide-Refractory Prostate and Breast Xenograft Tumors Implanted in Metastatic Sites In Vivo," $20^{th}$ *EORTC-NCI-AACR, Symposium on Molecular Targets and Cancer Therapeutics, European Journal of Cancer Supplements* 6(12):175, poster No. 555.

Dongiovanni, D. et al. (2008). "Gefitinib (ZD 1839): Therapy in Selected Patients With Non-Small Cell Lung Cancer (NSCLC)?" *Lung Cancer* Feb. 1, 2008 [Epub ahead of print] Available at: http://www.ncbi.nim.nih.gov/pubmed/18243402, last visited Oct. 2, 2009.

Dracopoli, N. C. et al. (Aug. 1, 1987). "Loss of Heterozygosity at Autosomal and X-Linked Loci During Tumor Progression in a Patient With Melanoma," *Cancer Research* 47(15):3995-4000.

Duell, E. J. et al. (Aug. 15, 2002). "A Population-Based Study of the *Arg399Gln* Polymorphism in X-Ray Repair Cross-Complementing Group 1 (XRCC1) and Risk of Pancreatic Adenocarcinoma," *Cancer Res.* 62:4630-4636.

Durkacz, B. W. et al. (Feb. 7, 1980). "(ADP-Ribose)$_n$ Participates in DNA Excision Repair," *Nature* 283:593-596.

Edwards, S. L. et al. (Feb. 28, 2008). "Resistance to Therapy Caused by Intragenic Deletion in *BRCA2*," *Nature* 451(7182):1111-1115, with one additional page "Methods".

El-Khaminsy, S. F. et al. (Oct. 2003). "A Requirement for PARP-1 for the Assembly or Stability of XRCC1 Nuclear Foci at Sites of Oxidative DNA Damage," *Nucleic Acid Res.* 31(19):5526-5533.

Ellis, M.K. et al. (Apr. 15, 1992). "Reactions of Nitrosonitrobenzenes with Biological Thiols: Identification and Reactivity of Glutathion-*S*-yl Conjugates," *Chem. Biol. Interactions* 82(2):151-163.

Erowid. (Jan. 2001). "Introduction to the Federal Controlled Substance Analogue Act," located at http://www.erowid.org/psychoactives/law/analog/analog_info 1.shtml. last visited Oct. 13, 2006, total of 4 pages.

Eyer, P. et al. (1980). "Biotransformation of Nitrosobenzene in the Red Cell and the Role of Glutathione," *Xenobiotica* 10(7/8):517-526.

Fierce Biotech. (2006). "Avastin encounters rare failure for pancreatic cancer," Fierce Biotech Web site, Jun. 26, 2006, available at: http://www.fiercebiotech.com/story/avastin-encounters-rare-failure-for-pancreatic-cancer/2006-06-27, last visited Oct. 2, 2008.

Fisher, B. et al. (Jul. 1997). "Effect of Preoperative Chemotherapy on Local-Regional Disease in Women With Operable Breast Cancer: Findings From the National Surgical Adjuvant Breast and Bowel Project B-18," *J. Clin. Oncol.* 15(7):2483-2493.

Fisher, B. et al. (Aug. 1998). "Effect of Preoperative Chemotherapy on the Outcome of Women With Operable Breast Cancer," *J. Clin. Oncol.* 16(8):2672-2685.

Flemming, G. F. (Jun. 1, 2004). "Phase III Trial of Doxorubicin plus Cisplatin With or Without Paclitaxel Plus Filgrastim in Advanced Endometrial Carcinoma: A Gynecologic Oncology Group Study," *J. Clin. Oncol.* 22(11):2159-2166; and comment in *Curr. Oncol. Rep.* (Nov. 2004). 6(6):455.

Flemming, G. F. et al. (Aug. 2004). "Phase III Randomized Trial of Doxorubicin + Cisplatin Versus Doxorubicin + 24-h Paclitaxel + Filgrastim in Endometrial Carcinoma, A Gynecologic Oncology Group Study," *Ann. Oncol.* 15(8):1173-1178.

Fletcher, J. A. et al. (Mar. 1991). "Ovarian Granulosa-Stromal Cell Tumors Are Characterized by Trisomy 12," *Am. J. Pathol.* 138(3):515-520.

Fojo, A. T. et al. (Nov. 1985). "Amplification of DNA Sequences in Human Multidrug-Resistant KB Carcinoma Cells," *Proc. Natl. Acad. Sci. USA* 82(22):7661-7665.

Fong, P. C. et al. (2006). "Phase I Pharmacokinetic (PK) and Pharmacodynamic (PD) Evaluation of a Small Molecule Inhibitor of Poly ADP-Ribose Polymerase (PARP), KU-0059436 (Ku) in Patients (p) With Advanced Tumours," *Supplement to Journal of*

*Clinical Oncology, 2006 ASCO Annual Meeting Proceedings*, Part I. vol. 24, No. 18S, Part I of II, (Jun. 20, 2006), p. 126s, abstract No. 3022.

Gäken, J. O. et al. (Jun. 1996). "Efficient Retroviral Infection of Mammalian Cells is Blocked by Inhibition of Poly(ADP-Ribose) Polymerase Activity," *Journal of Virology* 70(6):3992-4000.

Gallion, H. H. et al. (Sep. 1990). "Chromosome Abnormalities in Human Epithelial Ovarian Malignancies," *Gynecol. Oncol.* 38(3):473-477.

Garber, M. E. et al. (Nov. 20, 2001). "Diversity of Gene Expression in Adenocarcinoma of the Lung," *Proc. Natl. Acad. Sci. USA* 98(24):13784-13789. (Epub Nov. 13, 2001) and Erratum in *Proc. Natl. Acad. Sci. USA* (Jan. 22, 2002). 99(2):1098.

Garber, J. E. et al. (Dec. 14-17, 2006). "Neo-Adjuvant Cisplatin (CDDP) in 'Triple-Negative' Breast Cancer (BC)," *Breast Cancer Research and Treatment, Special Issue, 29th San Antonio Breast Cancer Symposium 2006*; vol. 100, Poster Session III, p. S149, Abstract No. 3074.

Goldstein, J. (Feb. 13, 2008). "Latest Avastin Breast Cancer Study Unlikely to Sway FDA," *The Wall Street Journal* located at http://blogs.wsj.com/health/2008/02/13/latest-avastin-breast-cancer-study-unlikely-to-sway-fda/, last visited on Feb. 15, 2008, 3 pages total.

Gradwohl, G. et al. (Apr. 1990). "The Second Zinc-Finger Domain of Poly(ADP-Ribose) Polymerase Determines Specificity for Single-Stranded Breaks in DNA," *Proc. Natl. Acad. Sci. USA* 87:2990-2994.

GREENFACTS.org. Definition of Solid Cancer, located at http://222.greenfacts.org/glossary/pqrs/solid-cancer.htm, last visited Jul. 18, 2009, one page total.

Griffin, R. J. et al. (Sep. 1995). "Novel Potent Inhibitors of the DNA Repair Enzyme Poly(ADP- Ribose)Polymerase (PARP)," *Anticancer Drug Design* 10(6):507-514.

Griffin, R. J. et al. (Jan. 10, 1996). "Novel Benzimidazole and Quinazolinone Inhibitors of the DNA Repair Enzyme Poly(ADP-Ribose)Polymerase," *Pharmaceutical Sciences* 2(1):43-47.

Griffin, R. J. et al. (1998). Resistance-Modifying Agents. 5. Synthesis and Biological Properties of Quinazolinone Inhibitors of the DNA Repair Enzyme Poly(ADP-Ribose) Polymerase (PARP). *J. Med. Chem.* 41:5247-5256.

Hakam, A. et al. (Feb. 1987). "Catalytic Activities of Synthetic Octadeoxyribonucleotides as Coenzymes of Poly(ADP-Ribose) Polymerase and the Identification of a New Enzyme Inhibitory Site," *FEBS Lett.* 212(1):73-78.

Harris, N. L. et al. (Dec. 1999). "World Health Organization Classification of Neoplastic Diseases of the Hematopoietic and Lymphoid Tissues: Report of the Clinical Advisory Committee Meeting-Airlie House, Virginia, Nov. 1997," *J. Clin. Oncol.* 17(12)3835-3849.

Heighway, J. et al. (Oct. 31, 2002). "Expression Profiling of Primary Non-Small Cell Lung Cancer for Target Identification," *Oncogene* 21(50):7749-7763.

Hegi, M. E. et al. (Mar. 10, 2005). "MGMT Gene Silencing and Benefit From Temozolomide in Glioblastoma," *N. Engl. J. Med.* 352(10):997-1003.

Henderson, Z. et al. (Aug. 25, 1981). "Primary Structure of the Low Molecular Weight Nucleic Acid-binding Proteins of Murine Leukemia Viruses," *J. Biol. Chem.* 256(16):8400-8403.

Hickman, J. A. (Sep. 1975). "Protection Against the Effects of the Antitumour Agent CB 1954 by Certain Imidazoles and Related Compounds," *Biochemical Pharmacology* 24(17):1947-1952.

Higashi, T. et al. (1983). "Retrospects and Prospects " *Glutathione: Storage, Transport and Turnover in Mammals*, eds., Sakamoto, Y. et al. Japan Sci. Soc. Press, Tokyo,/VNU Science Press, Utrecht, pp. 3-9.

Höglund, M. et al. (Jun. 15, 2003). "Ovarian Carcinoma Develops Through Multiple Modes of Chromosomal Evolution," *Cancer Research* 63(12):3378-3385.

Homesley, H. D. et al. (Feb. 10, 2007). "Phase III Trial of Ifosfamide With or Without Paclitaxel in Advanced Uterine Carcinosarcoma: A Gynecologic Oncology Group Study," *J. Clin. Oncol.* 25(5):526-531.

Honkoop, A. H. et al. (1998). "Prognostic Role of Clinical, Pathological and Biological Characteristics in Patients with Locally Advanced Breast Cancer," *Br. J. Cancer* 77(4):621-626.

Hubert, A. et al. (Aug.-Sep. 2004). "PARP-1, PARP-2 and ATM in the DNA Damage Response: Functional Synergy in Mouse Development," *DNA Repair (Amst)*. 3(8-9):1103-1108.

Hwang, S. J. et al. (Aug. 2003). "Lung Cancer Risk in Germline p53 Mutation Carriers: Association Between an Inherited Cancer Predisposition, Cigarette Smoking, and Cancer Risk," *Hum. Genet.* 113(3):238-243. Epub. Jun. 11, 2003.

Ishii, D. et al. (Aug. 2007). "Efficacy of Temozolomide is Correlated with 1p Loss and Methylation of the Deoxyribonucleic Acid Repair Gene MGMT in Malignant Gliomas," *Neurol. Med. Chir.* (Tokyo) 47(8):341-350.

Iwabuchi, H. et al. (Dec. 15, 1995). "Genetic Analysis of Benign, Low-Grade, and High-Grade Ovarian Tumors," *Cancer Res.* 55(24):6172-6180.

Jaboin, J. et al. (Nov. 1, 2002). "MS 27-275, an Inhibitor of Histone Deacetylase, Has Marked in Vitro and in Vivo Antitumor Activity Against Pediatric Solid Tumors," *Cancer Research* 62:6108-6115.

Jagtap, P. et al. (2002). "Novel Phenanthridinone Inhibitors of Poly (Adenosine 5'-Diphosphate- Ribose) Synthetase: Potent Cytoprotective and Antishock Agents," *Crit. Care Med*. 30(5):1071-1082.

Jemal, A. et al. (Jan./Feb. 2003). Cancer Statistics 2003). *CA Cancer J. Clin.* 53(1):5-26.

Jenkins, R. B. et al. (Nov. 1993). "Cytogenetic Studies of Epithelial Ovarian Carcinoma," *Cancer Genet. Cytogenet.* 71(1):76-86.

Jeon, I. S. et al. (Mar. 16, 1995). "A Varian Ewing's Sarcoma Translocation (7;22) Fuses the *EWS* Gene to the ETS Gene *ETV1*," *Oncogene* 10(6):1229-1234.

Karczewski, J. M. et al. (1999). "Prevention of Oxidant-Induced Cell Death in Caco-2 Colon Carcinoma Cells after Inhibition of Poly(ADP-Ribose) Polymerase and $Ca^{2+}$ Chelation: Involvement of a Common Mechanism," *Biochem. Pharmacol*. 57:19-26.

Kerley-Hamilton, J. S. et al. (Sep. 8, 2005). "A p53-Dominant Transcriptional Response to Cisplatin in Testicular Gene Cell Tumor-Derived Human Emnbyronal Carcinoma," *Oncogene* 24(40) :6090-6110.

Kiechle, M. et al. (Feb. 1, 2001). "Comparative Genomic Hybridization Detects Genetic Imbalances in Primary Ovarian Carcinomas as Correlated With Grade of Differentiation," *Cancer* 91(3):534-540.

Kiechle-Schwarz, M. et al. (Nov. 1994). "Recurrent Cytogenetic Aberrations and Loss of Constitutional Heterozygosity in Ovarian Carcinomas," *Gynecol. Oncol*. 55(2):198-205.

Kim, M. Y. et al. (Dec. 17, 2004). "$NAD^+$-Dependent Modulation of Chromatin Structure and Transcription by Nucleosome Binding Properties of PARP-1," *Cell* 119(6):803-814.

Kindler, H. L. (2007) "A Double-Blind, Placebo-Controlled, Randomized Phase III Trial of Gemcitabine (G) Plus Bevacizumab (B) Versus Gemcitabine plus Placebo (P) in Patients (pts) with Advanced Pancreatic Cancer (PC): A Preliminary Analysis of Cancer and Leukemia Group B (CALGB) 80303," Gastrointestintal Cancers Symposium: Mutidisciplinary Approaches to the Prevention, Diagnosis, and Therapy of GI Cancers, Jan. 19-21, 2007, Orlando, Florida, p. 319, abstract 108.

Kiyohara, C. et al. (Sep. 2002). "Genetic Polymorphisms and Lung Cancer Susceptibility: A Review," *Lung Cancer* 37(3):241-256.

Ko, A. H. (Feb. 17, 2003), "Cancer of the Pancreas," published by Cancer Supportive Care Programs, article located at http://www.cancersupportivecare.com/pancreas/html, last visited on Sep. 23, 2009, 5 pages total.

Kosower, E.M. (1976). "Chemical Properties of Glutathione," Chapter 1 in *Glutathione Metabolism and Function*, Arias, M. et al., eds., Raven Press: New York, NY, Kroc Foundation Series, vol. 6, pp. 1-15.

Kuerer H. M., et al. (1998). "Pathologic Tumour Response in the Breast Following Neoadjuvant Chemotherapy Predicts Axillary Lymph Node Status," *Cancer J. Sci. Am*. 4:230-236.

Kuerer H. M. et al. (Feb. 1999). "Clinical Course of Breast Cancer Patients With Complete Pathologic Primary Tumour and Axillary Lymph Node Response to Doxorubicin-Based Neoadjuvant Chemotherapy," *J. Clin. Oncol*. 17(2):460-469.

Kume, K. et al. (2005). "Mutations in the Serine Protease Inhibitor Kazal Type 1 (*SPINK1*) Gene in Japanese Patients with Pancreatitis," *Pancreatology* 5:354-360.

Kun, E. et al (1983). "Biochemical Basis of the Regulatory Role of Polyadenosine Diiphosphoribose," *Advances in Enzyme Regulation* 21:177-199.

Lau, A. et al. (Oct. 21-24, 2008). Pre-Clinical Activity of the PARP Inhibitor Olaparib (AZD2281) in Homologous Recombination Repair Deficient Triple Negative Breast Cancer, Poster at *20th EORTC-NCI-AACR Symposium on "Molecular Targets and Cancer Therapeutics,"* Oct. 21-24, 2008, Geneva, Switzerland, two pages.

Lee-Jones, L. (Aug. 2003). "Ovary: Germ Cell Tumors," *Atlas of Genetics and Cytogenetics in Oncology and Haematology*, pp. 591-605, located at http://atlasgeneticsoncology.org/Tumors/OvarianGermCellID5067.pdf, last visited on Sep. 25, 2009, 15 pages total.

Lee-Jones, L. (Nov. 2003). "Ovary: Sex Cord-Stromal Tumors," *Atlas of Genetics and Cytogenetics in Oncology and Haematology*, 8(1):125-131, located at http://AtlasGeneticsOncology.org/Tumors/OvarSexCordStromID5223.html, last visited on Sep. 25, 2009, 15 pages total.

Lee-Jones, L. (Dec. 2003). :Ovary: Epithelial Tumors, *Atlas Genet Cytogenet Oncol Haematol* 8(2):256-302, located at http://atlasgeneticsoncology.org/Tumors/OvaryEpithTumID5230.pdf, 51 pages total.

Lev, D. C. et al. (Aug. 2003). "Dacarbazine Causes Transcriptional up-Regulation of Interleukin 8 and Vascular Endothelial Growth Factor in Melanoma Cells; A Possible Escape Mechanism From Chemotherapy," *Mol. Cancer Therap.* 2(8):753-763.

Lever, A. et al. (1989). "Identification of a Sequence Required for Efficient Packaging of Human Immunodeficiency Virus Type 1 RNA into Virus," *J. Virol.* 63(9):4085-4087.

Lewis, G. D. et al. (Sep. 1993). "Differential Responses of Human Tumor Cell Lines to Anti-p185HER2 Monoclonal Antibodies," *Cancer Immunol. Immunother.* 37(4):255-263.

Li, J.-H. et al. (2001). "Synthesis of Substituted 5[*H*]phenanthridin-6-ones as Potent Poly(ADP- Ribose)Polymerase-1 (PARP1) Inhibitors," *Bioorg. Med. Chem. Lett.* 11:1687-1690.

Li, D. et al. (Mar. 27, 2004). "Pancreatic Cancer," *The Lancet* 363:1049-1057.

Loesch, D. M. (Dec. 8-11, 2005). "Phase II Trial of Gemcitabine Plus Carboplatin (plus Trastuzumab in HER-2 Positive Patients) in Metastatic Breast Cancer Patients," *Breast Cancer Research and Treatment, Special Issue 28th annual San Antonio Breast Cancer Symposium 2005*, San Antonio, Texas, vol. 94, Supplement 1, p. S280, Poster Session VI, Abstract No. 6092.

Marchesi, F. et al. (Oct. 2007). "Triazene Compounds: Mechanism of Action and Related DNA Repair Systems," *Pharmacol. Res.* 56(4):275-287.

Marsit, C. J. et al. (Jan. 29, 2004). "Inactivation of the Fanconi Anemia/BRCA Pathway in Lung and Oral Cancers: Implications For Treatment and Survival," *Oncogene* 23(4):1000-1004.

Masson, M. et al. (Jun. 1998). "XRCC1 is Specifically Associated With Poly(ADP-Ribose) Polymerase and Negatively Regulates its Activity Following DNA Damage," *Mol. Cell Biol.* 18(6):3563-3571.

Masutani, M. et al. (Dec. 2003). "Poly(ADP-Ribose) and Carcinogenesis," *Genes, Chromosomes, and Cancer* 38(4):339-348.

Mayr, D. et al. (Sep. 2002). "Characteristic Pattern of Genetic Aberrations in Ovarian Granulosa Cell Tumors," *Mod. Pathol.* 15(9):951-957.

Mazzon, E. et al. (2001). "GPI 6150, a Poly (ADP-Ribose) Polymerase Inhibitor, Exhibits an Anti- Inflammatory Effect in Rat Models of Inflammation," *Eur. J. Pharmacol.* 415:85-94.

McLaughlin, P. et al. (Aug. 1998). "Rituximab Chimeric Anti-CD20 Monoclonal Antibody Therapy for Relapsed Indolent Lymphoma: Half of Patients Respond to a Four-Dose Treatment Program," *J. Clin. Oncol.* 16(8):2825-2833.

McCluggage, W. G. (May 2002). "Malignant Biphasic Uterine Tumors: Carcinosarcomas or Metaplastic Carcinomas?" *J. Clin. Pathol.* 55(5):321-325.

Meric, C. et al. (Apr. 1989). "Characterization of Moloney Murine Leukemia Virus Mutants with Single-Amino-Acid Substitutions in the Cys-His Box of the Nucleocapsid," *J. Virol.* 63(4):1558-1568.

Mitsuuchi, Y. et al. (Oct. 30, 2002). "Cytogenetics and Molecular Genetics of Lung Cancer," *Am. J. Med. Genet.* 115(3):183-188.

Miller, D. S. et al. (Aug. 2005). "Phase II Evaluation of Topotecan in Carcinosarcoma of the Uterus: A Gynecologic Oncology Group Study," *Gynecologic Oncology* 98(2):217-221.

Mrózek, K. et al. (Mar. 1990). "Trisomy of Chromosome 12 in a Case of Thecoma of the Ovary," *Gynecol. Oncol.* 36(3):413-416.

Mugneret, F. et al. (Jun. 1988). "Chromosomes in Ewing's Sarcoma. II. Nonrandom Additional Changes, Trisomy 8 and der(16)t(1:16)," *Cancer Genet. Cytogenet.* 32(2):239-245.

Nahleh, Z. et al. (Nov. 2007). "Trastuzumab not for Ductal Carcinoma in Situ?" *Anticancer Drugs* 18(10):1231-1235.

Nahta, R. et al. (May 2006). "Mechanisms of Disease: Understanding Resistance to HER2-Targeted Therapy in Human Breast Cancer," *Nat. Clin. Pract. Oncol.* 3(5):269-280.

National Cancer Institute. (2005). "Bevacizumab Combined With Chemotherapy Improves Progression-Free Survival for Patients With Advanced Breast Cancer," U.S. National Institutes of Health, available at: http://www.cancer.gov/newscenter/pressreleases/AvastinBreast, last visited Oct. 2, 2009, also *Ther.* 4(8):1239.

O'Brien, J. et al. (2000). "Investigation of the Alamar Blue (Resazurin) Fluorescent Dye for the Assessment of Mammalian Cell Cytotoxicity," *Eur. J. Biochem. FEBS* 267(17):5421-5426.

Ogston, K. N. et al. (2003). "A New Histological Grading System to Assess Response of Breast Cancers to Primary Chemotherapy: Prognostic Significance and Survival," *Breast* 12:320-327.

Okano, S. et al. (Jun. 2003). "Spatial and Temporal Cellular Responses to Single-Strand Breaks in Human Cells," *Mol. Cell Biol.* 23(11): 3974-3981.

Olver, I. N. (Feb. 2008). "Trastuzumab as the Lead Monoclonal Antibody in Advanced Breast Cancer: Choosing Which Patient and When," *Future Oncol.* 4(1):125-131.

Omura, G. A. et al. (Aug. 15, 1983). "A Randomized Study of Adriamycin With and Without Dimethyl Triazenoimidazole Carboxamide in Advanced Uterine Sarcomas," *Cancer* 52(4):626-632.

Oosting-Lenstra, S. F. et al. (Dec. 2007). "Failure of CHOP with Rituximab for Lymphomatoid Granulomatosis," *Neth. J. Med.* 65(11):442-447.

(OSI)™ Pharmaceuticals, (Aug. 9, 2005). "Tarceva® (Erlotinib) Tablets NDA 21-743, S003, Supplemental NDA: Pancreatic Cancer, Briefing Document, ODAC Meeting Sep. 13, 2005," PDF located at http://www.fda.gov/ohrms/dockets/AC/05/briefing/2005-4174B1_03_01-OSI-Tarceva.pdf, 66 pages total, last visited Sep. 25, 2009.

Paez, J. G. et al. (Jun. 4, 2004). "*EGFR* Mutations in Lung Cancer: Correlation With Clinical Response to Gefitinib Therapy," *Science* 304(5676):1497-1500.

Palmer, B. D. et al. (Jul. 8, 1994). "Hypoxia-Selective Antitumor Agents. 9. Structure-Activity Relationships for Hypoxia-Selective Cytotoxicity Among Analogues of 5-[*N,N*- bis(2-Chloroethyl)Amino]-2,4-Dinitrobenzamide," *J. Med. Chem.* 37(14):2175-2184, (p. 2175 only).

Pao, W. et al. (Sep. 7, 2004). "EGF Receptor Gene Mutations are Common in Lung Cancers From 'Never Smokers' and are Associated With Sensitivity of Tumors to Gefitinib And Erlotinib," *Proc. Natl. Acad. Sci. USA* 101(36):13306-13311.

Park, C. et al. (2005). "Induction of Apoptosis and Inhibition of Cycloosygenase-2 Expression by *N*-Methyl-*N*-Nitro-*N*-Nitrosoguanidine in Human Leukemia Cells," *Anti-Cancer Drugs* 16(5):507-513.

Pedersen, M. I. et al. (Feb. 1, 1986). "Nonrandom Chromosome Structural Aberrations and Oncogene Loci in Human Malignant Melanoma," *Cancer Genet. Cytogenet.* 20(1-2):11-27.

Pejovic, T. et al. (May 1990). "Trisomy 12 is a Consistent Chromosomal Aberration in Benign Ovarian Tumors," *Genes Chromosomes Cancer* 2(1):48-52.

Pejovic, T. et al. (Jan. 1992). "Chromosome Aberrations in 35 Primary Ovarian Carcinomas," *Genes Chromosomes Cancer* 4(1):58-68.

Pejovic, T. et al. (Feb. 1995). "Genetic Changes in Ovarian Cancer," *Ann. Med.* 27(1):73-78.

Perkins, E. et al. (May 15, 2001). "Novel Inhibitors of Poly(ADP-Ribose) Polymerase/PARP1 and PARP2 Identified Using a Cell-Based Screen in Yeast," *Cancer Res.* 61:4175-4183.

Plummer, R. et al. (2005). "First in Human Phase I Trial of the PARP Inhibitor AG-014699 With Temozolomide (TMZ) in Patients (pts) With Advanced Solid Tumors, 2005 41st Annual Meeting of the American Society of Clinical Oncology, May 13-17, 2005, Orlando Florida, 2005 Annual Meeting Proceedings Part I, (a supplement to the Journal of Clinical Oncology," vol. 23, No. 16S, Part I of II (Jun. 1 Supplement), p. 208s, abstract No. 3065.

Plummer, R. et al. (2006)."First and Final Report of a Phase II Study of the Poly(ADP-Ribose) Polymerase (PARP) Inhibitor, AG014699, in Combination With Temozolomide (TMZ) in Patients With Metastatic Malignant Melanoma (MM)," 2006 42nd Annual Meeting of the American Society of Clinical Oncology, Jun. 2-6, 2006, Atlanta, GA, Supplement to the *Journal of Clinical Oncology*, Part I of II, vol. 24, No. 18S (Jun. 20, 2006) p. 456s, abstract No. 8013.

Porta, M. et al. (Dec. 18-25, 1999). "Serum Concentrations of Organochlorine Compounds and K-*ras* Mutations in Exocrine Pancreatic Cancer," from the PANKRAS II Study Group, *The Lancet* 354:2125-2129.

Powles, T. J. et al. (Mar. 1995). "Randomized Trial of Chemoendocrine Therapy Started Before or After Surgery for Treatment of Primary Breast Cancer," *J. Clin. Oncol.* 13(3):547-552.

Rattan, S. I. et al. (Jun. 15, 1994). "Kinetin Delays the Onset of Ageing Characteristics in Human Fibroblasts," *Biochem. Biophys. Res. Comm.* 201(2):665-672.

Razzak, A. R. et al. (2008). "Heterogeneity of Breast Cancer and Implications of Adjuvant Chemotherapy," *Breast Cancer* 15(1):31-34.

Ries, L.A.G., et al. (eds). (2007) SEER Cancer Statistics Review, 1975-2004, National Cancer Institute. Bethesda, MD, based on Nov. 2006 SEER data submission, posted to the SEER web site, 2007, located at http://seer.cancer.gov/csr/1975_2004/.

Richmond, A. et al. (Mar. 1986). "Growth Factor and Cytogenetic Abnormalities in Cultured Nevi and Malignant Melanomas," *J. Invest. Dermatol.* 86(3):295-302.

Roberts, C. G. et al. (Sep. 1990). "Cytogenetic Study of Solid Ovarian Tumors," *Cancer Genet. Cytogenet.* 48(2):243-253.

Roche—Media News. (2006). "US Phase III Study of Avastin in Advanced Pancreatic Cancer Does Not Meet Primary Endpoint," Basel, Jun. 27, 2006, Roche Web site, located at http://www.roche.com/investors/ir_update/inv-update-2006-06-27.htm, last visited Mar. 4, 2008.

Ruscetti, T. et al. (Jun. 5, 1998). "Stimulation of the DNA-Dependent Protein Kinase by Polv(ADP-Ribose) Polymerase," *J. Biol. Chem.* 273(23):14461-14467.

Said, S. I. et al. (May 1996). "Excitotoxicity in the Lung: *N*-Methyl-D-Aspartate-Induced, Nitric Oxide-Dependent, Pulmonary Edema is Attenuated by Vasoactive Intestinal Peptide and by Inhibitors of Poly(ADP-Ribose) Polymerase," *Proc. Natl. Acad. Sci. USA* 93:4688-4692.

Saito, A. et al. (Apr. 1999). "A Synthetic Inhibitor of Histone Deacetylase, MS-27-275, With Marked in vivo Antitumor Activity Against Human Tumors," *Proc. National Acad. Sci. USA* 96:4592-4597.

Sakai, W. et al. (Feb. 28, 2008). "Secondary Mutations as a Mechanism of Cisplatin Resistance in BRCA2-Mutated Cancers," *Nature* 451:1116-1121.

Sataloff, D. M. et al. (Mar. 1995). "Pathologic Response to Induction Chemotherapy in Locally Advanced Carcinoma of the Breast: a Determinant of Outcome," *J. Am.Coll. Surg.* 180(3):297-306.

Schlicker, A. et al. (Jan. 1, 1999). "4-Amino-1,8-Naphthalimide: a Novel Inhibitor of Poly(ADP-Ribose) Polymerase and Radiation Sensitizer," *Int. J. Radiat. Biol.* 75(1):91-100.

Seracchioli, R. et al. (Jun. 2001). "Conservative Treatment of Recurrent Ovarian Fibromas in a Young Patient Affected by Gorlin Syndrome," *Hum. Reprod.* 16(6):1261-1263.

Shall, S. et al. (May 11, 1999). "Preparation of Aminobenzamides and Related Compounds as Inhibitors of Poly(ADP-Ribose)-Metabolizing Enzymes," *Chemical Abstracts* 116(19):193929e.

Shall, S. et al. (Jun. 30, 2000). "Poly(ADP-Ribose) Polymerase-1: What Have We Learned From the Deficient Mouse Model?" *Mutat Res.* 460(1):1-15.

Shaw, et al. (1998). "Practice Parameters in Adults With Suspected or Known Supratentorial Nonoptic Pathway Low-Grade Glioma," *Neurosurg. Focus.* From American Association of Neurological Surgeons, 4(6), Article 10, 11 pages total.

Shen, D.-W. et al. (Jun. 15, 1986). "Multiple Drug-Resistant Human KB Carcinoma Cells Independently Selected for High-Level Resistance to Colchicine, Adriamycin, or Vinblastine Show Changes in Expression of Specific Proteins," *J. Biol. Chem.* 261(17):7762-7770.

Silverberg, S. G. et al. (1991). "Carcinomas," in Tumors of the Uterine Corpus and Gestational Trophoblastic Disease, *Atlas of Tumor Pathology*, in 3rd Series, Fascicule 3, Washington D. C., Armed Forces Institute of Pathology, pp. 166-179.

Simbulan-Rosenthal, C. M. et al., (Nov. 20, 2003). "PARP-1 Binds E2F-1 Independently of its DNA Binding and Catalytic Domains, and Acts as a Novel Coactivator of E2F-1-Mediated Transcription During Re-Entry of Quiescent Cells into S Phase," *Oncogene* 22(52):8460-8471.

Simonin, F. et al. (Jun. 25, 1993). "The Carboxyl-Terminal Domain of Human Poly(ADP-Ribose) Polymerase. Overproduction in *Escherichia coli*, Large Scale Purification and Characterization," *J. Biol. Chem.* 268(18):13454-13461.

Slayton, R. E. et al. (Jun. 1987). "Phase II Trial of Etoposide in the Management of Advanced or Recurrent Mixed Mesodermal Sarcomas of the Uterus: A Gynecologic Oncology Group Study," *Cancer Treatment Reports* 71(6):661-662.

Sonoda, G. et al. (Dec. 1997b). "Comparative Genomic Hybridization Detects Frequent Overrepresentation of Chromosomal Material From 3q26, 8q24, and 20q13 in Human Ovarian Carcinomas," *Genes Chromosomes Cancer* 20(4):320-328.

Soriano, F. G. et al. (Jan. 2001). "Diabetic Endothelial Dysfunction: The Role of Poly(ADP-Ribose) Polymerase Activation," *Nature Medicine* 7(1):108-113.

Sorlie, T. et al. (Jul. 8, 2003). "Repeated Observation of Breast Tumor Subtypes in Independent Gene Expression Data Sets," *Proc. Natl. Acad. Sci. USA* 100(14):8418-8423. Epub Jun. 26, 2003.

Stephenson, C. F. et al. (Nov. 1992). "Cytogenetic and Pathologic Aspects of Ewing's Sarcoma and Neuroectodermal Tumors," *Hum. Pathol.* 23(11):1270-1277.

Stryer, L. (1981). *Biochemistry*, Second Edition, W.H. Freeman and Company: San Francisco, CA, Part II, Chapter 15 entitled "Pentose Phosphate Pathway and Glucogenesis," pp. 343-345.

Sutton, G. P. et al. (Aug. 1989). "Phase II Trial of Ifosfamide and Mesna in Mixed Mesodermal Tumors of the Uterus, (A Gynecologic Oncology Group Study)." *Am. J. Obstet. Gynecol.* 161(2):309-312.

Sutton, G. et al. (Nov. 2000). "A Phase III Trial of Ifosfamide With or Without Cisplatin in Carcinosarcoma of the Uterus, A Gynecologic Oncology Group Study," *Gynecologic Oncology* 79(2):147-153, and comment in Gynecol. Oncol. (Nov. 2000) 79(2)145-146.

Suzuki, S. et al. (Oct. 1, 2000). "An Approach to Analysis of Large-Scale Correlations Between Genome Changes and Clinical Endpoints in Ovarian Cancer," *Cancer Research* 60(19):5382-5385.

Szabó, C. et al. (1997). "Regulation of Components of the Inflammatory Response by 5-Iodo-6-Amino-1,2Benzopyrone, an Inhibitor of Poly(ADP-Ribose) Synthetase and Pleiotropic Modifier of Cellular Signal Pathways," *International Journal of Oncology* 10(6):1093-1101.

Szoka, F. et al. (1978). "Procedure for Preparation of Liposomes With Large Internal Aqueous Space and High Capture by Reverse-Phase Evaporation," *Proc. Nat'l Acad. Sci. USA* 75(9):4194-4198.

Taetle, R. et al. (Jul. 1999). "Chromosome Abnormalities Adenocarcinoma: I. Nonrandom Chromosome Abnormalities from 244 Cases," *Genes Chromosomes Cancer* 25(3):290-300.

Tanner, M. M. et al. (May 2000). "Frequent Amplification of Chromosomal Region 20q12-q13 in Ovarian Cancer," *Clin. Cancer Research* 6(5):1833-1839.

Taruscio, D. et al. (Jun. 1993). "Detection of Trisomy 12 on Ovarian Sex Cord Stromal Tumors by Fluorescence in Situ Hybridization," *Diagn. Mol. Pathol.* 2(2):94-98.

Thigpen, J. T. et al. (Feb. 1986). "Phase II Trial of Cisplatin in the Treatment of Patients with Advanced or Recurrent Mixed Mesodermal Sarcomas of the Uterus: A Gynecologic Oncology Group Study," *Cancer Treatment Reports* 70(2):271-274.

Thigpen, J. T. et al. (Oct. 1, 2004). "Phase III Trial of Doxorubicin With or Without Cisplatin in Advanced Endometrial Carcinoma: A Gynecologic Oncology Group Study," *J. Clin. Oncol.* 22(19):3902-3908.

Thompson, F. H. et al. (Mar. 1994). "Clonal Chromosome Abnormalities in 54 Cases of Ovarian Carcinoma," *Cancer Genet. Cytogenet.* 73(1):33-45.

Tuma, R. S. et al. (Sep. 25, 2007). "Targeting DNA Repair in BRCA Mutation Carriers," *Oncology Times* 29(18):52-53.

Turc-Carel, C. et al. (Jun. 1988). "Chromosomes in Ewing's Sarcoma. I. An Evaluation of 85 Cases of Remarkable Consistency of t(11;22)(q24;q12)," *Cancer Genet. Cytogenet.* 32(2):229-238.

Virag, L. et al. (1999). "Inhibition of Poly(ADP-Ribose) Synthetase (PARS) and Protection Against Peroxynitrite-Induced Cytotoxicity by Zinc Chelation," *Br. J. Pharmacol.* 126:769-777.

Virag, L. (1999). "Requirement of Intracellular Calcium Mobilization for Peroxynitrite-Induced Poly(ADP-Ribose) Synthetase Activation and Cytotoxicity," *Mol. Pharmacol.* 56:824-833.

Virag, L. et al. (2001). "Purines Inhibit Poly(ADP-Ribose) Polymerase Activation and Modulate Oxidant-Induced Cell Death," *FASEB J.* 15:99-107.

Virag,L. et al. (2002). "The Therapeutic Potential of Poly(ADP-Ribose) Polymerase Inhibitors," *Pharmacol Rev.* 54(3):375-429.

Wang, Z. Q. et al. (1995). "Mice Lacking ADPRT and Poly(ADP-Ribosyl)ation Develop Normally but are Susceptible to Skin Disease," *Genes Dev.* 9:509-520.

Watson, C. Y. et al. (1998). "Synthesis of 3-Substituted Benzamides and 5-Substituted Isoquinolin- 1(2H)-ones and Preliminary Evaluation as Inhibitors of Poly(ADP-Ribose)Polymerase (PARP)," *Bioorg Med Chem.* 6:721-734.

White, A. W. et al. (2000). "Resistance-Modifying Agents. 9. Synthesis and Biological Properties of Benzimidazole Inhibitors of The DNA Repair Enzyme Poly(ADP-Ribose) Polymerase," *J. Med. Chem.* 43:4084-4097.

Wiewrodt, D. et al. (Mar. 15, 2008). "MGMT in Primary and Recurrent Human Glioblastomas After Radiation and Chemotherapy and Comparison With p53 Status and Clinical Outcome," *Int. J. Cancer* 122(6):1391-1399.

Williams, C. et al. (1998). "Tamoxifen for Relapse of Ovarian Cancer," Cochrane Database of Systematic Reviews of 1998, Issue 2, reprinted and published in the Cochrane Library 2009, Issue 4, 19 pages total.

Wolff, M. E. ed. M E ed. (1995). *Burger's Medicinal Chemistry and Drug Discovery*, vol. I: *Principles and Practice*, $5^{th}$ edition, John Wiley & Sons, pp. 975-977.

Yang-Feng, T. L. et al. (Jul. 9, 1991). "Trisomy 12 and K-ras-2-Amplification in Human Ovarian Tumors," *Int. J. Cancer* 48(5):678-681.

Yoshida, S. et al. (Jan. 1991). "Production of 2-Methyl-4[$3H$]-Quinazolinone, an Inhibitor of Poly(ADP-Ribose) Synthetase, by Bacterium," *The Journal of Antibiotics* (Tokyo), 44(1):111-112.

Zabarovsky, E. R. et al. (Oct. 7, 2002). "Tumor Suppressor Genes on Chromosome 3p Involved in the Pathogenesis of Lung and Other Cancers," *Oncogene* 21(45):6915-6935.

Zhang, J. et al. (Nov. 30, 2000). "GPI 6150 Prevents $H_2O_2$ Cytotoxicity by Inhibiting Poly(ADP-Ribose) Polymerase," *Biochem. Biophys. Res. Comm.* 278(3):590-598.

International Search Report mailed on Dec. 3, 2007, for PCT Application No. PCT/US07/71053 filed on Jun. 12, 2007, 1 page.

International Search Report mailed on Oct. 16, 2007, for PCT Application No. PCT/US06/27907 filed on Jul. 18, 2006, 1 page.

International Search Report mailed on Jun. 16, 2008, for PCT Application No. PCT/US07/77651 filed on Sep. 5, 2007, 1 page.

International Search Report mailed on Feb. 13, 2009, for PCT Application No. PCT/US08/85756 filed on Dec. 5, 2008, 1 page.

Written Opinion of the International Search Authority mailed on Oct. 16, 2007, for PCT Patent Application No. PCT/US06/27907 filed Jul. 18, 2006.

U.S. Appl. No. 12/496,593, filed Jul. 1, 2009, for Sherman et al.

U.S. Appl. No. 12/502,943, filed Jul. 14, 2009, for Sherman et al.

U.S. Appl. No. 12/510,969, filed Jul. 28, 2009, for Sherman et al.

Bowman, K. J. et al. (Jan. 5, 2001). "Differential Effects of the Poly(ADP-Ribose) Polymerase (PARP) Inhibitor NU1025 on Topoisomerase I and II Inhibitor Cytotoxicity in L1210 Cells in Vitro," *Br. J. Cancer* 84(1):106-112.

Cancer.org (2005). "What is Ovarian Cancer?" available online as of Feb. 5, 2005 as evidenced by the attached Internet Archive Report located at http://www.cancer.org/docroot/CRI/content/CRI_2_4_1X_What_is_ovarian_cancer_33.asp, 6 pages total.

Delaney, C. A. et al. (Jul. 2000). "Potentiation of Temozolomide and Topotecan Growth Inhibition and Cytotoxicity by Novel Poly(Adenosine Diphosphoribose) Polymerase Inhibitors in a Panel of Human Tumor Cell Lines," *Clin. Cancer Res.* 6(7):2860-2867.

Fedier, A. et al. (May 2003). "The Effect of Loss of BRCA1 on the Sensitivity to Anticancer Agents in p53-Deficient Cells," *Int. J. Oncol.* 22(5):1169-1173, Abstract only located in PubMed.

Herzog, T. J. (2002). "Update on the Role of Topotecan in the Treatment of Recurrent Ovarian Cancer," *Oncologist* 7(suppl. 5):3-10.

Powell, S. N. et al. (Sep. 1, 2003). "Roles of BRCA1 and BRCA2 in Homologous Recombination, DNA Replication Fidelity and the Cellular Response in Ionizing Radiation," Oncogene 22(37):5784-5791.

Andersen, B. et al. (Oct. 15, 2002). "The Effect of Glucose on the Potency of Two Distinct Glycogen Phosphorylase Inhibitors," *Biochem. J.* 367(Pt 2):443-450.

Balakumar, P. et al. (2006). "Effect of 3-Aminobenzamide, an Inhibitor of Poly(ADP-Ribose) Polymerase in Experimental Cardiac Hypertrophy," *Int. J. Pharmacol.* 2(5):543-548.

Boros, L. G. et al. (Mar. 6, 2002). "Metabolic Profiling of Cell Growth and Death in Cancer: Applications in Drug Discovery," *Drug Discovery Today* 7(6):364-372.

Comin-Anduix, B. et al. (Aug. 2001). "The Effect of Thiamine Supplementation on Tumour Proliferation. A Metabolic Control Analysis Study," *Eur. J. Biochem.* 268(15):4177-4182.

Kuhajda, F. P. et al. (Jul. 5, 1994). "Fatty Acid Synthesis: A Potential Selective Target for Antineoplastic Therapy," *Proc. Nat'l. Acad. Sci USA* 91(14):6379-6383.

Kuhajda, F. P. et al. (Mar. 28, 2000). "Synthesis and Antitumor Activity of an Inhibitor of Fatty Acid Synthase," *Proc. Nat'l. Acad. Sci USA* 97(7):3450-3454.

Lee, W.-N. et al. (Mar. 20, 1995). "Isotopomer Study of Lipogenesis in Human Hepatoma Cells in Culture: Contribution of Carbon and Hydrogen Atoms from Glucose," *Anal. Biochem.* 226(1):100-1 12.

Lee, W.-N. et al. (Sep.-Dec. 1996). "Mass Isotopomer Study of Glutamine Oxidation and Synthesis in Primary Culture of Astrocytes," *Dev. Neurosci.* 18(5-6):469-477.

Lee, W.-N. et al. (May 1998). "Mass Isotopomer Study of the Nonoxidative Pathways of the Pentose Cycle with [1,2-$^{13}C_2$] Glucose," *Am. J. Physiol. Endocrinol. Metab.* 274(5 Pt 1):E843-E851.

Lee, W.-N. et al. (Aug. 14, 1998). "Fatty Acid Cycling in Human Hepatoma Cells and the Effects of Troglitazone," *J. Biol. Chem.* 273(33):20929-20934.

Leimer, K. R. et al. (Aug. 21, 1977). "Complete Mass Spectra of N-Trifluoroacetyl-n-Butyl Esters of Amino Acids," *J. Chromatography* 141(2):121-144.

Loftus, T. M. et al. (Jun. 30, 2000). "Reduced Food Intake and Body Weight in Mice Treated with Fatty Acid Synthase Inhibitors," *Science* 288(5475):2379-2381.

Menendez, J. A. et al. (Apr. 1, 2005). "Does Endogenous Fatty Acid Metabolism Allow Cancer Cells to Sense Hypoxia and Mediate Hypoxic Vasodilation? Characterization of a Novel Molecular Connection Between Fatty Acid Synthase (FAS) and Hypoxia-Inducible Factor-1α (HIF-1α)-Related Expression of Vascular Endothelial Growth Factor (VEGF) in Cancer Cells Overexpressing Her-2/neu Oncogene," *J. Cell Biochem* 94(5):857-863.

Menendez, J. A. et al. (Jul./Aug. 2005). "Targeting Fatty Acid Synthase: Potential for Therapeutic Intervention in Her-2/neu-Overexpressing Breast Cancer," *Drug News & Perspective* 18(6):375-385.

Pizer, E. S. et al. (Jun. 15, 1996). "Inhibition of Fatty Acid Synthesis Induces Programmed Cell Death in Human Breast Cancer Cells," *Cancer Res.* 56(12):2745-2747.

Sabate, L. et al. (Jan. 12, 1995). "A Model of the Pentose Phosphate Pathway in Rat Liver Cells," *Mol. Cell Biochem.* 142(1):9-17.

Written Opinion of the International Search Authority mailed on Jun. 16, 2008, for PCT Application No. PCT/US07/77651 filed on Sep. 5, 2007, 4 pages.

Written Opinion of the International Search Authority mailed on Dec. 3, 2007, for PCT Application No. PCT/US07/71053 filed on Jun. 12, 2007, 5 pages.

Non Final Office Action mailed on Dec. 2, 2009, for U.S. Appl. No. 11/850,626, filed Sep. 5, 2007, 8 pages.

Non Final Office Action mailed on Mar. 4, 2010, for U.S. Appl. No. 12/269,833, filed Nov. 12, 2008, 25 pages.

U.S. Appl. No. 12/748,209 filed Mar. 26, 2010, for Ossovskaya et al.

* cited by examiner

TREATMENT OF BREAST CANCER WITH A PARP INHIBITOR ALONE OR IN COMBINATION WITH ANTI-TUMOR AGENTS

CROSS REFERENCE

This application claims the benefit of U.S. Provisional Application No. 60/987,333, entitled "Treatment of Triple Negative Metastatic Breast Cancer with a Combination of an Antimetabolite, a Platinum Complex, and a PARP Inhibitor" filed Nov. 12, 2007; U.S. Provisional Application No. 61/012,364, entitled "Treatment of Cancer with Combinations of Topoisomerase Inhibitors and PARP Inhibitors" filed Dec. 7, 2007; and U.S. Provisional Application No. 61/058,528, entitled "Treatment of Breast, Ovarian, and Uterine Cancer with a PARP Inhibitor" filed Jun. 3, 2008, each of which applications is incorporated herein in its entirety by reference.

BACKGROUND

Cancer is a group of diseases characterized by aberrant control of cell growth. The annual incidence of cancer is estimated to be in excess of 1.3 million in the United States alone. While surgery, radiation, chemotherapy, and hormones are used to treat cancer, it remains the second leading cause of death in the U.S. It is estimated that over 560,000 Americans will die from cancer each year.

Cancer cells simultaneously activate several pathways that positively and negatively regulate cell growth and cell death. This trait suggests that the modulation of cell death and survival signals could provide new strategies for improving the efficacy of current chemotherapeutic treatments.

Breast cancer is generally treated with a combination of surgery to remove the cancerous lesion and adjuvant therapy—radiation, chemotherapy or both—to attack any cancer cells that may be left after the surgery. Breast cancer can be classified broadly by the presence or absence of hormone receptors (HRs). Hormone receptor positive (HR+) cancer is characterized by the expression of one or both female hormone receptors—estrogen receptor (ER) or progesterone receptor (PR). Adjuvant therapy for ER+ breast cancer often includes chemotherapy with a selective estrogen receptor modulator (SERM), such as tamoxifen or raloxifene. Unfortunately, while about 70% of breast cancers are ER positive, the remaining 30% of breast cancers that are HR negative are not amenable to treatment with SERMs. Accordingly, other adjuvant chemotherapies, such as treatment with an anthracycline (alone or in combination with a taxane) have been tried on ER negative breast cancer.

Treatment with anthracycline is limited by lifetime dosing limits based on cardiotoxicity concerns. Treatment with gemcitabine and carboplatin is an established combination chemotherapy for metastatic breast cancer patients—whether taxane-naïve or taxane-pretreated. Platinum agents have demonstrated promising antitumor activity in basal-like locally advanced breast cancers. DNA damaging agents have promising antitumor efficacy against basal-like breast cancer because of defects in DNA repair pathways inherent in these breast cancers.

Despite the availability of antimetabolites such as gemcitabine and platinum complex agents such as carboplatin, there is no accepted standard of care for ER negative breast cancer. In particular, triple negative metastatic breast cancer (i.e. breast cancer that is ER negative, and/or PR negative, and/or human epidermal growth factor receptor 2 (HER2) negative) is refractory to standard treatments and is entirely refractory to SERM chemotherapy. There is thus a need for an effective treatment for cancer in general, and especially for triple negative metastatic breast cancer.

Although there are limited therapeutic options for cancer treatment, variants of cancers, including triple negative breast cancer, are especially difficult because they can be refractory to standard chemotherapeutic or hormonal treatment. There is thus a need for an effective treatment for cancer in general, and cancer variants in particular.

SUMMARY OF THE INVENTION

In some embodiments, the present invention provides a method of treating breast cancer that is negative for at least one of ER, PR, or HER2 in a patient, comprising administering to the patient at least one PARP inhibitor. In some embodiments, the present invention provides a method of treating breast cancer that is negative for at least one of ER, PR, or HER2 in a patient in need thereof, comprising: (a) obtaining a sample from the patient; (b) testing the sample to determine each of the following: whether the cancer is ER-positive or ER-negative; whether the cancer is PR-positive or PR-negative; whether the cancer is HER2-positive or HER2-negative; (c) if the testing indicates that the cancer is negative for at least one of ER, PR, or HER2, treating the patient with at least one PARP inhibitor. In some embodiments, the method further comprises treating the patient with at least one PARP inhibitor, if two or more of the following conditions are met: (a) the cancer is ER-negative, (b) the cancer is PR-negative, (c) the cancer is HER2-negative. In some embodiments, the present invention provides a method of treating breast cancer that is negative for at least one of ER, PR, or HER2 in a patient, comprising: (a) testing a sample from the patient for PARP expression; and (b) if the PARP expression exceeds a predetermined level, administering to the patient at least one PARP inhibitor.

In practicing any of the subject methods disclosed herein, at least one therapeutic effect is obtained, said at least one therapeutic effect being reduction in size of a breast tumor, reduction in metastasis, complete remission, partial remission, stable disease, or a pathologic complete response. In some embodiments, a comparable clinical benefit rate (CBR=CR+PR+SD≧6 months) is obtained with treatment of the PARP inhibitor as compared to treatment with an anti-tumor agent. In some embodiments, the improvement of clinical benefit rate is at least about 30% as compared to treatment with an anti-tumor agent alone. In some embodiments, the PARP inhibitor is a PARP-1 inhibitor. In some embodiments, the PARP 1 inhibitor is 4-iodo-3-nitrobenzamide or a metabolite thereof. In some embodiments, the PARP inhibitor is of Formula (IIa) or a metabolite thereof:

I.

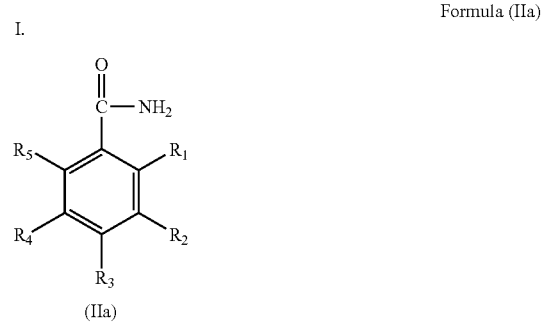

Formula (IIa)

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent to a $R_1$, $R_2$, $R_3$, $R_4$ or $R_5$ group that is a nitroso, hydroxyamino, hydroxy or amino group. In some embodiments, the compounds of (2) are such that the iodo group is always adjacent to a $R_1$, $R_2$, $R_3$, $R_4$ or $R_5$ group that is a nitroso, hydroxyamino, or amino group.

In some embodiments, the breast cancer is a metastatic breast cancer. In some embodiments, the breast cancer is at stage I, stage II, or stage III. In some embodiments, the breast cancer is negative for at least one of: ER, PR or HER2. In some embodiments, the breast cancer is negative for at least one of: ER, PR or HER2; and wherein the breast cancer is positive for at least one of ER, PR or HER2. In some embodiments, the breast cancer is deficient in homologous recombination DNA repair. In some embodiments, the breast cancer has impaired function of BRCA1 or BRCA2. In some embodiments, the treatment comprises a treatment cycle of at least 11 days, wherein on days 1, 4, 8 and 11 of the cycle, the patient receives about 1 to about 100 mg/kg of 4-iodo-3-nitrobenzamide or a molar equivalent of a metabolite thereof. In some embodiments, 4-iodo-3-nitrobenzamide is administered orally, as a parenteral injection or infusion, or inhalation. In some embodiments, the treatment cycle is about 11 to about 30 days in length. In some embodiments, the method further comprises administering to the patient a PARP inhibitor in combination with at least one anti-tumor agent. The anti-tumor agent is an antitumor alkylating agent, antitumor antimetabolite, antitumor antibiotics, plant-derived antitumor agent, antitumor platinum complex, antitumor camptothecin derivative, antitumor tyrosine kinase inhibitor, monoclonal antibody, interferon, biological response modifier, hormonal anti-tumor agent, anti-tumor viral agent, angiogenesis inhibitor, differentiating agent, PI3K/mTOR/AKT inhibitor, cell cycle inhibitor, apoptosis inhibitor, hsp 90 inhibitor, tubulin inhibitor, DNA repair inhibitor, anti-angiogenic agent, receptor tyrosine kinase inhibitor, topoisomerase inhibitor, taxane, agent targeting Her-2, hormone antagonist, agent targeting a growth factor receptor, or a pharmaceutically acceptable salt thereof. In some embodiments, the anti-tumor agent is citabine, capecitabine, valopicitabine or gemcitabine. In some embodiments, the anti-tumor agent is selected from the group consisting of Avastin, Sutent, Nexavar, Recentin, ABT-869, Axitinib, Irinotecan, topotecan, paclitaxel, docetaxel, lapatinib, Herceptin, lapatinib, tamoxifen, a steroidal aromatase inhibitor, a non-steroidal aromatase inhibitor, Fulvestrant, an inhibitor of epidermal growth factor receptor (EGFR), Cetuximab, Panitumimab, an inhibitor of insulin-like growth factor 1 receptor (IGF1R), and CP-751871. In some embodiments, the method further comprises administering to the patient a PARP inhibitor in combination with more than one anti-tumor agent. In some embodiments, the anti-tumor agent is administered prior to, concomitant with or subsequent to administering the PARP inhibitor. In some embodiments, the method further comprises surgery, radiation therapy, chemotherapy, gene therapy, DNA therapy, viral therapy, RNA therapy, DNA therapy, adjuvant therapy, neoadjuvant therapy, immunotherapy, nanotherapy or a combination thereof. In some embodiments, the method further comprises administering to the patient a PARP inhibitor in combination with gamma irradiation. In some embodiments, the sample is a tissue or bodily fluid sample. In some embodiments, the sample is a tumor sample, a blood sample, a blood plasma sample, a peritoneal fluid sample, an exudate or an effusion. In some embodiments, the method further comprises testing a sample from the patient for expression of estrogen receptor, progesterone receptor or human epidermal growth factor 2 receptor.

In some embodiments, the present invention provides a method of treating breast cancer in a patient, comprising administering to the patient at least one PARP inhibitor in combination with at least one anti-tumor agent. In some embodiments, the present invention provides a method of treating breast cancer in a patient in need thereof, comprising: (a) obtaining a sample from the patient; (b) testing the sample to determine each of the following: whether the cancer is ER-positive or ER-negative; whether the cancer is PR-positive or PR-negative; whether the cancer is HER2-positive or HER2-negative; (c) if the testing indicates that the cancer is negative for at least one of ER, PR, or HER2, treating the patient with a combination of therapeutic agents, wherein the therapeutic agents include at least one PARP inhibitor and at least one anti-tumor agent. In some embodiments, the method further comprises treating the patient with a combination of therapeutic agents, wherein the therapeutic agents include at least one PARP inhibitor and at least one anti-tumor agent, if two or more of the following conditions are met: (a) the cancer is ER-negative, (b) the cancer is PR-negative, (c) the cancer is HER2-negative. In some embodiments, the present invention provides a method of treating breast cancer in a patient, comprising: (a) testing a sample from the patient for PARP expression; and (b) if the PARP expression exceeds a predetermined level, administering to the patient at least one PARP inhibitor and at least one anti-tumor agent.

In practicing any of the subject methods disclosed herein, in some embodiments, at least one therapeutic effect is obtained, said at least one therapeutic effect being reduction in size of a breast tumor, reduction in metastasis, complete remission, partial remission, stable disease, or a pathologic complete response. In some embodiments, an improvement of clinical benefit rate (CBR=CR+PR+SD≧6 months) is obtained as compared to treatment with the anti-tumor agent but without the PARP inhibitor. In some embodiments, the improvement of clinical benefit rate is at least about 60%. In some embodiments, the PARP inhibitor is 4-iodo-3-nitrobenzamide or a metabolite thereof. In some embodiments, the PARP inhibitor is of Formula (IIa) or a metabolite thereof:

IIa.

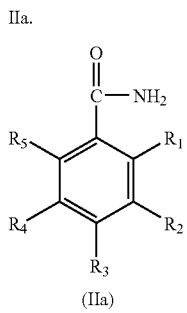

Formula (IIa)

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent to a $R_1$, $R_2$, $R_3$, $R_4$ or $R_5$ group that is a nitroso, hydroxyamino, hydroxy or amino group. In some embodiments, the compounds of (2) are such that the iodo group is always adjacent to a $R_1$, $R_2$, $R_3$, $R_4$ or $R_5$ group that is a nitroso, hydroxyamino, or amino group.

In some embodiments, the anti-tumor agent is an antitumor alkylating agent, antitumor antimetabolite, antitumor antibiotics, plant-derived antitumor agent, antitumor platinum complex, antitumor camptothecin derivative, antitumor tyrosine kinase inhibitor, monoclonal antibody, interferon, biological response modifier, hormonal anti-tumor agent, anti-tumor viral agent, angiogenesis inhibitor, differentiating agent, PI3K/mTOR/AKT inhibitor, cell cycle inhibitor, apoptosis inhibitor, hsp 90 inhibitor, tubulin inhibitor, DNA repair inhibitor, anti-angiogenic agent, receptor tyrosine kinase inhibitor, topoisomerase inhibitor, taxane, agent targeting Her-2, hormone antagonist, agent targeting a growth factor receptor, or a pharmaceutically acceptable salt thereof. In some embodiments, the anti-tumor agent is citabine, capecitabine, valopicitabine or gemcitabine. In some embodiments, the anti-tumor agent is selected from the group consisting of Avastin, Sutent, Nexavar, Recentin, ABT-869, Axitinib, Irinotecan, topotecan, paclitaxel, docetaxel, lapatinib, Herceptin, lapatinib, tamoxifen, a steroidal aromatase inhibitor, a non-steroidal aromatase inhibitor, Fulvestrant, an inhibitor of epidermal growth factor receptor (EGFR), Cetuximab, Panitumimab, an inhibitor of insulin-like growth factor 1 receptor (IGF1R), and CP-751871. In some embodiments, the method further comprises surgery, radiation therapy, chemotherapy, gene therapy, DNA therapy, viral therapy, DNA therapy, adjuvant therapy, neoadjuvant therapy, RNA therapy, immunotherapy, nanotherapy or a combination thereof. In some embodiments, the method further comprises administering to the patient a PARP inhibitor in combination with gamma irradiation.

In some embodiments, the breast cancer is a metastatic breast cancer. In some embodiments, the breast cancer is at stage I, stage II, or stage III. In some embodiments, the breast cancer is HR-negative breast cancer. In some embodiments, the breast cancer is negative for at least one of: ER, PR or HER2. In some embodiments, the breast cancer is negative for at least one of: ER, PR or HER2; and wherein the breast cancer is positive for at least one of ER, PR or HER2. In some embodiments, the breast cancer is deficient in homologous recombination DNA repair. In some embodiments, the breast cancer has impaired function of BRCA1 or BRCA2. In some embodiments, the treatment comprises a treatment cycle of at least 11 days, wherein: (a) on days 1 and 8 of the cycle, the patient receives about 100-5000 mg/m² gemcitabine; (b) on days 1 and 8 of the cycle, the patient receives about 10 to about 400 mg/m² of carboplatin; and (c) on days 1, 4, 8 and 1 of the cycle, the patient receives about 1 to about 100 mg/kg of 4-iodo-3-nitrobenzamide or a molar equivalent of a metabolite thereof. In some embodiments, the treatment cycle is about 11 to about 30 days in length. In some embodiments, on days 1 and 8 of the cycle, the patient receives about 100-2500 mg/m² of gemcitabine and about 10 to about 400 mg/m² of carboplatin; and on days 1, 4, 8 and 11 of the cycle the patient receives about 1 to about 50 mg/kg of 4-iodo-3-nitrobenzamide or a molar equivalent of a metabolite thereof. In some embodiments, on days 1 and 8 of the cycle the patient receives about 500-2000 mg/m² of gemcitabine and about 50 to about 400 mg/m² of carboplatin; and on days 1, 4, 8 and 11 of the cycle the patient receives about 1 to about 50 mg/kg of 4-iodo-3-nitrobenzamide or a molar equivalent of a metabolite thereof. In some embodiments, on days 1 and 8 of the cycle the patient receives about 1000 mg/m² of gemcitabine and about AUC 2 of carboplatin; and on days 1, 4, 8 and 11 of the cycle the patient receives about 1, 2, 3, 4, 6, 8 or 10, 12, 14, 16, 18 or 20 mg/kg of 4-iodo-3-nitrobenzamide. In some embodiments, the anti-tumor agent is administered as a parenteral injection or infusion. In some embodiments, the PARP inhibitor is 4-iodo-3-nitrobenzamide, which is administered orally, or as a parenteral injection or infusion, or inhalation. In some embodiments, the method further comprises administering to the patient a taxane by parenteral injection or infusion. In some embodiments, the sample is a tissue or bodily fluid sample. In some embodiments, the sample is a tumor sample, a blood sample, a blood plasma sample, a peritoneal fluid sample, an exudate or an effusion. In some embodiments, the method further comprises testing a sample from the patient for expression of estrogen receptor, progesterone receptor or human epidermal growth factor 2 receptor.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
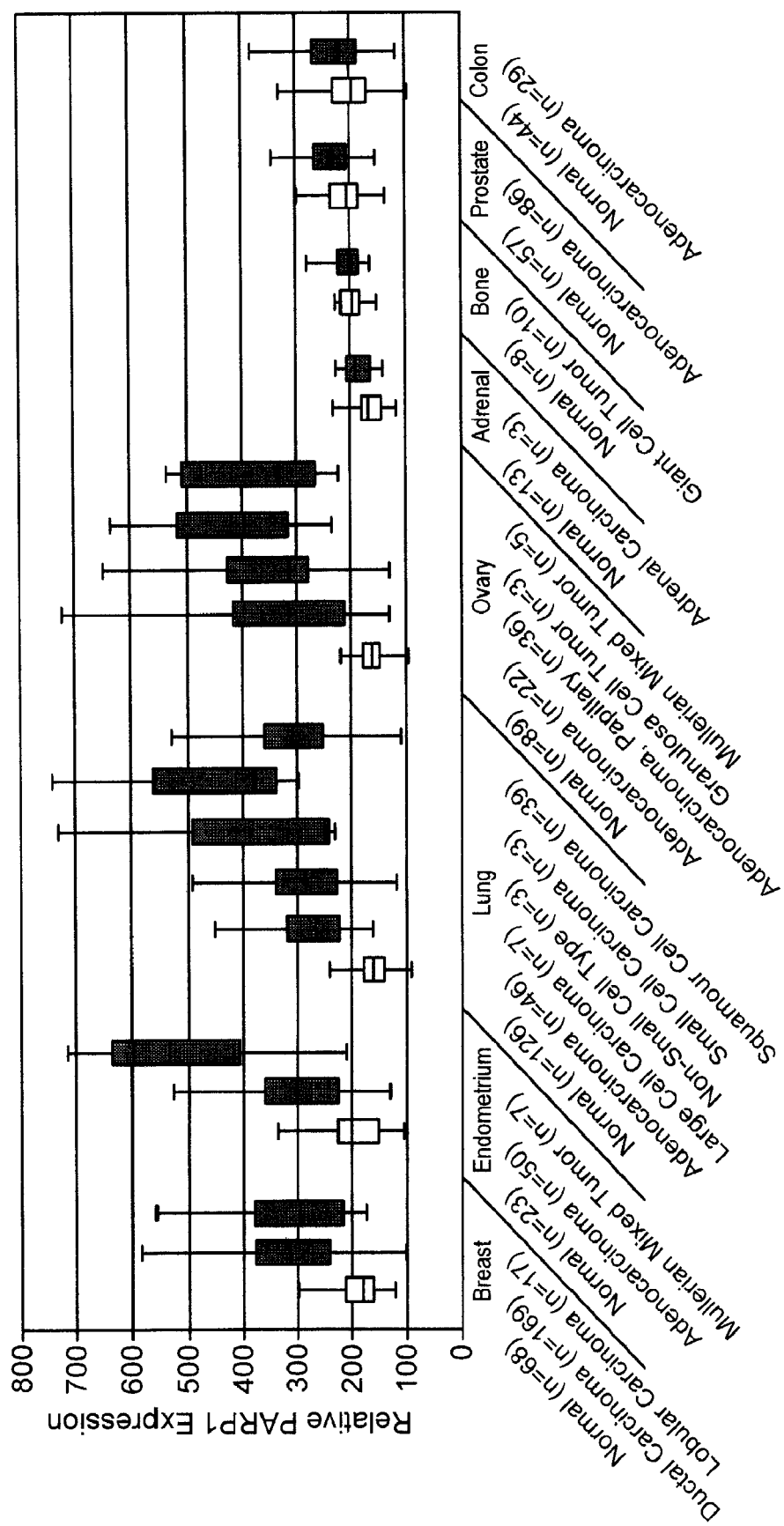
FIG. 1 shows upregulation of PARP1 gene expression in human primary cancers. Horizontal line, median PARP1 expression; box, interquartile range; bars, standard deviation.

In some embodiments, the present invention provides a method of treating breast cancer that is negative for at least one of ER, PR, or HER2 in a patient, comprising administering to the patient at least one PARP inhibitor. In some embodiments, at least one therapeutic effect is obtained, said at least one therapeutic effect being reduction in size of a breast tumor, reduction in metastasis, complete remission, partial remission, pathologic complete response, or stable disease. In some embodiments, a comparable clinical benefit rate (CBR=CR+PR+SD≧6 months) is obtained with treatment of the PARP inhibitor as compared to treatment with an anti-tumor agent. In some embodiments, the improvement of clinical benefit rate is at least about 30%. In some embodiments, the PARP inhibitor is a PARP-1 inhibitor. In some embodiments, the PARP inhibitor is of Formula (IIa) or a metabolite thereof:

III.

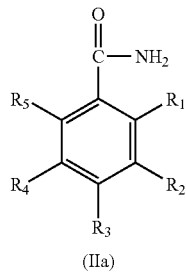

Formula (IIa)

(IIa)

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, $(C_1-C_6)$ alkyl, $(C_1-C_6)$ alkoxy, $(C_3-C_7)$ cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent to a $R_1$, $R_2$, $R_3$, $R_4$ or $R_5$ group that is a nitroso, hydroxyamino, hydroxy or amino group. In some embodiments, the compounds of (2) are such that the iodo group is always adjacent to a $R_1$, $R_2$, $R_3$, $R_4$ or $R_5$ group that is a nitroso, hydroxyamino, or amino group. In some embodiments, the PARP 1 inhibitor is 4-iodo-3-nitrobenzamide or a metabolite thereof.

In some embodiments, the breast cancer is a metastatic breast cancer. In some embodiments, the breast cancer is at stage I, II or III. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is an ER-negative breast cancer. In some embodiments, the breast cancer is ER-negative and HER2-positive. In some embodiments, the breast cancer is ER-negative and PR-positive. In some embodiments, the breast cancer is ER-negative and both HER2-positive and PR-positive. In some embodiments, the breast cancer is a PR-negative breast cancer. In some embodiments, the breast cancer is PR-negative and ER-positive. In some embodiments, the breast cancer is PR-negative and HER2-positive. In some embodiments, the breast cancer is PR-negative and both ER-positive and HER2-positive. In some embodiments, the breast cancer is a HER2-negative breast cancer. In some embodiments, the breast cancer is HER2-negative and ER-positive. In some embodiments, the breast cancer is HER2-negative and PR-positive. In some embodiments, the breast cancer is HER2-negative and both ER-positive and PR-positive. In some embodiments, the breast cancer is ER-negative and PR-negative. In some embodiments, the breast cancer is ER-negative, PR-negative and HER-2 positive. In some embodiments, the breast cancer is ER-negative and HER2-negative. In some embodiments, the breast cancer is ER-negative, HER2-negative and PR-positive. In some embodiments, the breast cancer is PR-negative and HER2-negative. In some embodiments, the breast cancer is PR-negative, HER2-negative and ER-positive. In some embodiments, the breast cancer is ER-negative, PR-negative and HER2-negative. In some embodiments, the breast cancer is deficient in homologous recombination DNA repair.

In some embodiments, the treatment comprises a treatment cycle of at least 11 days, wherein on days 1, 4, 8 and 11 of the cycle, the patient receives about 1 to about 100 mg/kg of 4-iodo-3-nitrobenzamide or a molar equivalent of a metabolite thereof. In some embodiments, 4-iodo-3-nitrobenzamide is administered orally, as a parenteral injection or infusion, or inhalation. In some embodiments, the treatment cycle is about 11 to about 30 days in length.

In some embodiments, the method further comprises administering to the patient a PARP inhibitor in combination with at least one anti-tumor agent. The anti-tumor agent is an antitumor alkylating agent, antitumor antimetabolite, antitumor antibiotics, plant-derived antitumor agent, antitumor organoplatinum compound, antitumor camptothecin derivative, antitumor tyrosine kinase inhibitor, monoclonal antibody, interferon, biological response modifier, hormonal anti-tumor agent, anti-tumor viral agent, angiogenesis inhibitor, differentiating agent, or other agent that exhibits anti-tumor activities, or a pharmaceutically acceptable salt thereof. In some embodiments, the anti-tumor agent is citabine, capecitabine, valopicitabine or gemcitabine. In some embodiments, the anti-tumor agent is a platinum complex. In some embodiments, the method further comprises administering to the patient a PARP inhibitor in combination with more than one anti-tumor agent. The anti-tumor agent is administered prior to, concomitant with or subsequent to administering the PARP inhibitor. In some embodiments, the method further comprises administering to the patient a PARP inhibitor in combination with an anti-angiogenic agent such as Avastin. In some embodiments, the method further comprises administering to the patient a PARP inhibitor in combination with a topoisomerase inhibitor, such as irinotecan or topotecan. In some embodiments, the method further comprises administering to the patient a PARP inhibitor in combination with a taxane such as paclitaxel or docetaxel. In some embodiments, the method further comprises administering to the patient a PARP inhibitor in combination with an agent targeting Her-2, such as Herceptin. In some embodiments, the method further comprises administering to the patient a PARP inhibitor in combination with hormone therapy, such as a hormone antagonist tamoxifen. In some embodiments, the method further comprises administering to the patient a PARP inhibitor in combination with an agent targeting a growth factor receptor, including an inhibitor of epidermal growth factor receptor (EGFR) and an inhibitor of insulin-like growth factor 1 (IGF-1) receptor (IGF1R). In some embodiments, the method further comprises administering to the patient a PARP inhibitor in combination with gamma irradiation. In some embodiments, the method further comprises surgery, radiation therapy, chemotherapy, gene therapy, DNA therapy, adjuvant therapy, neoadjuvant therapy, RNA therapy, DNA therapy, viral therapy, immunotherapy, nanotherapy or a combination thereof.

Some embodiments described herein provide a method of treating breast cancer in a patient, comprising administering to the patient at least one PARP inhibitor and at least one anti-tumor agent. In some embodiments, at least one therapeutic effect is obtained, said at least one therapeutic effect being reduction in size of a breast tumor, reduction in metastasis, complete remission, partial remission, pathologic complete response, or stable disease. In some embodiments, an improvement of clinical benefit rate (CBR=CR+PR+ SD≧6 months) is obtained as compared to treatment with the antimetabolite and platinum complex but without the PARP inhibitor. In some embodiments, the improvement of clinical benefit rate is at least about 60%. In some embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaplatin and oxaliplatin. In some embodiments, the platinum complex is carboplatin. In some embodiments, the antimetabolite is a citabine. In some embodiments, the antimetabolite is selected from the group consisting of citabine, capecitabine, gemcitabine and valopicitabine. In some embodiments, the antimetabolite is gemcitabine. In some embodiments, the method further comprises administering a taxane to the patient. In some embodiments, the taxane is paclitaxel or docetaxel. In some embodiments, the breast cancer is a metastatic breast cancer. In some embodiments, the breast cancer is at stage I, II or III. In some embodiments, the breast cancer is HR-negative breast cancer. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is HR-negative breast cancer. In some embodiments, the breast cancer is an ER-negative breast cancer. In some embodiments, the breast cancer is ER-negative and HER2-positive. In some embodiments, the breast cancer is ER-negative and PR-positive. In some embodiments, the breast cancer is ER-negative and both HER2-positive and PR-positive. In some embodiments, the breast cancer is a PR-negative breast cancer. In some embodiments, the breast cancer is PR-negative and ER-positive. In some embodiments, the breast cancer is PR-negative and HER2-positive. In some embodiments, the breast cancer is PR-negative and both ER-positive and HER2-positive. In some embodiments, the breast cancer is a HER2-negative breast cancer. In some embodiments, the breast cancer is HER2-negative and ER-positive. In some embodiments, the breast cancer is HER2-negative and PR-positive. In some embodiments, the breast cancer is HER2-negative and both ER-positive and PR-positive. In some embodiments, the breast cancer is ER-negative and PR-negative. In some embodiments, the breast cancer is ER-negative, PR-negative and HER-2 positive. In some embodiments, the breast cancer is ER-negative and HER2-negative. In some embodiments, the breast cancer is ER-negative, HER2-negative and PR-positive. In some embodiments, the breast cancer is PR-negative and HER2-negative. In some embodiments, the breast cancer is PR-negative, HER2-negative and ER-positive. In some embodiments, the breast cancer is ER-negative, PR-negative and HER2-negative. In some embodiments, the breast cancer is deficient in homologous recombination DNA repair.

In some embodiments, the methods further comprise administering a PARP inhibitor in combination with an anti-tumor agent. In some embodiments, the anti-tumor agent is an antitumor alkylating agent, antitumor antimetabolite, antitumor antibiotic, plant-derived antitumor agent, antitumor platinum complex, antitumor camptothecin derivative, anti-tumor tyrosine kinase inhibitor, monoclonal antibody, interferon, biological response modifier, hormonal anti-tumor agent, angiogenesis inhibitor, differentiating agent, or other agent that exhibits anti-tumor activities, or a pharmaceutically acceptable salt thereof. In some embodiments, the platinum complex is cisplatin, carboplatin, oxaplatin or oxaliplatin. In some embodiments, the antimetabolite is citabine, capecitabine, gemcitabine or valopicitabine. In some embodiments, the methods further comprise administering to the patient a PARP inhibitor in combination with more than one anti-tumor agent. In some embodiments, the anti-tumor agent is administered prior to, concomitant with or subsequent to administering the PARP inhibitor. In some embodiments, the anti-tumor agent is an anti-angiogenic agent, such as Avastin. In some embodiments, the anti-tumor agent is a topoisomerase inhibitor including but not limited to irinotecan, topotecan, or camptothecin. In some embodiments, the anti-tumor agent is a taxane including but not limited to paclitaxel or docetaxel. In some embodiments, the anti-tumor agent is an agent targeting Her-2, e.g. Herceptin. In some embodiments, the anti-tumor agent is a hormone antagonist, for example, tamoxifen. In some embodiments, the anti-tumor agent is an agent targeting a growth factor receptor. In some embodiments, such agent is an inhibitor of epidermal growth factor receptor (EGFR) or an inhibitor of insulin-like growth factor 1 (IGF-1) receptor (IGF1R). In other embodiments, the method further comprises surgery, radiation therapy, chemotherapy, gene therapy, DNA therapy, adjuvant therapy, neoadjuvant therapy, viral therapy, RNA therapy, immunotherapy, nanotherapy or a combination thereof.

In some embodiments, the treatment comprises a treatment cycle of at least 11 days, wherein on days 1, 4, 8 and 11 of the cycle, the patient receives about 10 to about 100 mg/kg of 4-iodo-3-nitrobenzamide or a molar equivalent of a metabolite thereof. In some embodiments, the treatment comprises a treatment cycle of at least 11 days, wherein on days 4, 8 and 11 of the cycle, the patient receives about 1 to about 50 mg/kg of 4-iodo-3-nitrobenzamide or a molar equivalent of a metabolite thereof. In some embodiments, the treatment comprises a treatment cycle of at least 11 days, wherein on days 1, 4, 8 and 11 of the cycle, the patient receives about 1, 2, 3, 4, 5, 6, 8, or 10, 12, 14, 16, 18, or 20 mg/kg of 4-iodo-3-nitrobenzamide.

In some embodiments, the treatment comprises a treatment cycle of at least 11 days, wherein: (a) on days 1 and 8 of the cycle, the patient receives about 100-2000 mg/m$^2$ gemcitabine; (b) on days 1 and 8 of the cycle, the patient receives about 10 to about 400 mg/m$^2$ of carboplatin; and (c) on days 1, 4, 8 and 11 of the cycle, the patient receives about 10 to about 100 mg/kg of 4-iodo-3-nitrobenzamide or a molar equivalent of a metabolite thereof. In some embodiments, on days 1 and 8 of the cycle, the patient receives about 100-2500 mg/m$^2$ of gemcitabine and about AUC 1-5 of carboplatin (about 10 to about 400 mg/m$^2$ of carboplatin); and on days 1, 4, 8 and 11 of the cycle the patient receives about 1 to about 50 mg/kg of 4-iodo-3-nitrobenzamide or a molar equivalent of a metabolite thereof. In some embodiments, on days 1 and 8 of the cycle the patient receives about 500-2000 mg/m$^2$ of gemcitabine and about 50 to about 400 mg/m$^2$ of carboplatin; and on days 1, 4, 8 and 11 of the cycle the patient receives about 1 to about 50 mg/kg of 4-iodo-3-nitrobenzamide or a molar equivalent of a metabolite thereof. In some embodiments, on days 1 and 8 of the cycle the patient receives about 1000 mg/m$^2$ of gemcitabine and about AUC 2 of carboplatin; and on days 1, 4, 8 and 11 of the cycle the patient receives about 1, 2, 3, 4, 6, 8 or 10, 12, 14, 16, 18 or 20 mg/kg of 4-iodo-3-nitrobenzamide.

Some embodiments described herein provide a method of treating breast cancer in a patient having triple negative breast cancer, comprising during a 21 day treatment cycle, on days 1, 4, 8 and 11 of the cycle, administering to the patient about 10 to about 100 mg/kg of 4-iodo-3-nitrobenzamide or a molar equivalent of a metabolite thereof. In some embodiments, the 4-iodo-3-nitrobenzamide is administered orally or as an intravenous infusion.

Some embodiments provide a method of treating breast cancer in a patient having triple negative breast cancer, comprising during a 21 day treatment cycle: (a) on days 1 and 8 of the cycle, administering to the patient about 100-2000 mg/m$^2$ gemcitabine; (b) on days 1 and 8 of the cycle, administering to the patient AUC 0.1-10 of carboplatin (about 10 to 400 mg/m$^2$ of carboplatin); and (c) on days 1, 4, 8 and 11 of the cycle, administering to the patient about 10 to about 100 mg/kg of 4-iodo-3-nitrobenzamide or a molar equivalent of a metabolite thereof. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Some embodiments described herein provide a method of treating breast cancer in a patient having triple negative breast cancer, comprising: (a) establishing a treatment cycle of about 10 to about 30 days in length; (b) on from 1 to 10 separate days of the cycle, administering to the patient about 1 mg/kg to about 50 mg/kg of 4-iodo-3-nitrobenzamide, or a molar equivalent of a metabolite thereof. In some embodiments, the 4-iodo-3-nitrobenzamide is administered orally or as an intravenous infusion.

Some embodiments described herein provide a method of treating breast cancer in a patient having triple negative breast cancer, comprising: (a) establishing a treatment cycle of about 10 to about 30 days in length; (b) on from 1 to 5 separate days of the cycle, administering to the patient about 100 to about 5000 mg/m$^2$ of gemcitabine by intravenous infusion; (c) on from 1 to 5 separate days of the cycle, administering to the patient AUC 1 to AUC 10 of carboplatin by intravenous infusion (e.g. about 10 to about 400 mg/m$^2$ of carboplatin); and (d) on from 1 to 10 separate days of the cycle, administering to the patient about 1 mg/kg to about 50 mg/kg of 4-iodo-3-nitrobenzamide, or a molar equivalent of a metabolite thereof. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Some embodiments include a method of treating breast cancer in a patient in need of such treatment, comprising: (a) obtaining a sample from the patient; (b) testing the sample to determine at least one of the following: (i) whether the cancer is ER-positive or ER-negative; (ii) whether the cancer is PR-positive or PR-negative; (iii) whether the cancer is HER2-positive or HER2-negative; (c) if the testing indicates that the cancer is ER-negative, PR-negative or HER2-negative, treating the patient with a combination of therapeutic agents, wherein the therapeutic agents include at least one antimetabolite, at least one platinum complex and at least one PARP inhibitor; and (d) if the testing does not indicate that the cancer is ER-negative, PR-negative or HER2-negative, selecting a different treatment option.

Some embodiments include a method of treating breast cancer in a patient in need of such treatment, comprising: (a) obtaining a sample from the patient; (b) testing the sample to determine at least one of the following: (i) whether the cancer is ER-positive or ER-negative; (ii) whether the cancer is PR-positive or PR-negative; (iii) whether the cancer is HER2-positive or HER2-negative; (c) if the testing indicates that the cancer is ER-negative, PR-negative or HER2-negative, treating the patient with at least one PARP inhibitor; and (d) if the testing does not indicate that the cancer is ER-negative, PR-negative or HER2-negative, selecting a different treatment option.

In some embodiments, at least one therapeutic effect is obtained, said at least one therapeutic effect being reduction in size of a breast tumor, reduction in metastasis, complete remission, partial remission, pathologic complete response, or stable disease. In some embodiments, an improvement of clinical benefit rate (CBR=CR+PR+SD$\geq$6 months) is obtained as compared to treatment without the PARP inhibitor. In some embodiments, the clinical benefit rate is at least about 30%. In some embodiments, an improvement of clinical benefit rate (CBR=CR+PR+SD$\geq$6 months) is obtained as compared to treatment with the antimetabolite and platinum complex but without the PARP inhibitor. In some embodiments, the clinical benefit rate is at least about 60%. In some embodiments, the PARP inhibitor is a PARP-1 inhibitor. In other embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaliplatin and oxaliplatin. In some embodiments, the platinum complex is carboplatin. In some embodiments, the antimetabolite is a citabine. In some embodiments, the antimetabolite is selected from the group consisting of citabine, capecitabine, gemcitabine and valopicitabine. In some embodiments, the antimetabolite is gemcitabine. In some embodiments, the method further comprises administering a taxane to the patient. In some embodiments, the taxane is paclitaxel or docetaxel. In some embodiments, the sample is a tissue or bodily fluid sample. In some embodiments, the sample is a tumor sample, a blood sample, a blood plasma sample, a peritoneal fluid sample, an exudate or an effusion. In some embodiments, the breast cancer is a metastatic breast cancer. In some embodiments, the breast cancer is an ER-negative metastatic breast cancer. In some embodiments, the breast cancer is at stage I, II or III. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is ER-negative and PR-positive. In some embodiments, the breast cancer is ER-negative and HER2-positive. In some embodiments, the breast cancer is ER-negative and both PR-positive and HER2-positive. In some embodiments, the breast cancer is a PR-negative metastatic breast cancer. In some embodiments, the breast cancer is PR-negative and ER-positive. In some embodiments, the breast cancer is PR-negative and HER2-positive. In some embodiments, the breast cancer is PR-negative and both ER-positive and HER2-positive. In some embodiments, the breast cancer is a HER2-negative metastatic breast cancer. In some embodiments, the breast cancer is HER2-negative and ER-positive. In some embodiments, the breast cancer is HER2-negative and PR-positive. In some embodiments, the breast cancer is HER2-negative and both ER-positive and PR-positive. In some embodiments, the breast cancer is ER-negative and PR-negative. In some embodiments, the breast cancer is ER-negative, PR-negative and HER2-positive. In some embodiments, the breast cancer is ER-negative and HER2-negative. In some embodiments, the breast cancer is ER-negative, HER2-negative and PR-positive. In some embodiments, the breast cancer is PR-negative and HER2-negative. In some embodiments, the breast cancer is PR-negative, HER2-negative and PR-positive. In some embodiments, the breast cancer is ER-negative, PR-negative and HER2-negative.

Some embodiments of the invention provide a method of treating breast cancer in a patient in need of such treatment, comprising: (a) obtaining a sample from the patient; (b) testing the sample to determine each of the following: (i) whether the cancer is ER-positive or -negative; (ii) whether the cancer is PR-positive or -negative; (iii) whether the cancer is HER2-positive or -negative; (c) if two or more of the following conditions are met, treating the patient with at least one PARP inhibitor: (i) the cancer is ER-negative, (ii) the cancer is PR-negative, or (iii) the cancer is HER2-negative; and (d) if at least two of the foregoing conditions are not met, selecting a different treatment option. Some embodiments of the invention provide a method of treating breast cancer in a patient in need of such treatment, comprising: (a) obtaining a sample from the patient; (b) testing the sample to determine each of the following: (i) whether the cancer is ER-positive or -negative; (ii) whether the cancer is PR-positive or -negative; (iii) whether the cancer is HER2-positive or -negative; (c) if two or more of the following conditions are met, treating the patient with a combination of therapeutic agents, wherein the therapeutic agents include at least one antimetabolite, at least one platinum complex and at least one PARP inhibitor: (i) the cancer is ER-negative, (ii) the cancer is PR-negative, or (iii) the cancer is HER2-negative; and (d) if at least two of the foregoing conditions are not met, selecting a different treatment option. In some embodiments, at least one therapeutic effect is obtained, said at least one therapeutic effect being reduction in size of a breast tumor, reduction in metastasis, complete remission, partial remission, pathologic complete response, or stable disease. In some embodiments, an improvement of clinical benefit rate (CBR=CR+PR+SD≧6 months) is obtained as compared to treatment without the PARP inhibitor. In some embodiments, the clinical benefit rate is at least about 30%. In some embodiments, an improvement of clinical benefit rate (CBR=CR+PR+SD≧6 months) is obtained as compared to treatment with the antimetabolite and platinum complex but without the PARP inhibitor. In some embodiments, the clinical benefit rate is at least about 60%. In some embodiments, the sample is a tissue or bodily fluid sample. In some embodiments, the sample is a tumor sample, a blood sample, a blood plasma sample, a peritoneal fluid sample, an exudate or an effusion. In some embodiments, the PARP inhibitor is a PARP-1 inhibitor. In other embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaliplatin and oxaliplatin. In some embodiments, the platinum complex is carboplatin. In some embodiments, the antimetabolite is a citabine. In some embodiments, the antimetabolite is selected from the group consisting of citabine, capecitabine, gemcitabine and valopicitabine. In some embodiments, the antimetabolite is gemcitabine. In some embodiments, the method further comprises administering a taxane to the patient. In some embodiments, the taxane is paclitaxel or docetaxel. In some embodiments, the breast cancer is a metastatic breast cancer. In some embodiments, the breast cancer is at stage I, II or III. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is an ER-negative metastatic breast cancer. In some embodiments, the breast cancer is a PR-negative metastatic breast cancer. In some embodiments, the breast cancer is a HER2-negative metastatic breast cancer. In some embodiments, the breast cancer is ER-negative and PR-negative. In some embodiments, the breast cancer is ER-negative and HER2-negative. In some embodiments, the breast cancer is PR-negative and HER2-negative. In some embodiments, the breast cancer is ER-negative, PR-negative and HER2-negative. In some embodiments, the treatment comprises selecting a treatment cycle of at least 11 days and: (a) on days 1, 4, 8 and 11 of the cycle, the patient receives about 10 to about 100 mg/kg of 4-iodo-3-nitrobenzamide or a molar equivalent of a metabolite thereof. In some embodiments, the 4-iodo-3-nitrobenzamide is administered orally or as an intravenous infusion. In some embodiments, the treatment comprises selecting a treatment cycle of at least 11 days and: (a) on days 1 and 8 of the cycle, the patient receives about 100-2000 mg/m² gemcitabine; (b) on days 1 and 8 of the cycle, the patient receives about 10 to about 400 mg/m² of carboplatin; and (c) on days 1, 4, 8 and 11 of the cycle, the patient receives about 10 to about 100 mg/kg of 4-iodo-3-nitrobenzamide or a molar equivalent of a metabolite thereof. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Some embodiments disclosed herein provide a method of treating breast cancer in a patient in need of such treatment, comprising: (a) obtaining a sample from the patient; (b) testing the sample to determine each of the following: (i) whether the cancer is ER-positive or -negative; (ii) whether the cancer is PR-positive or -negative; and (iii) whether the cancer is HER2-positive or -negative; (c) if two or more of the following conditions are met, treating the patient with at least one PARP inhibitor: (i) the cancer is ER-negative, (ii) the cancer is PR-negative, or (iii) the cancer is HER2-negative; and (d) if two or more of conditions (i)-(iii) are not met, selecting a different treatment option.

Some embodiments described herein provide a method of treating ER-negative, PR-negative, HER-2 negative metastatic breast cancer in a patient in need of such treatment, comprising administering to said patient at least one PARP inhibitor. In some embodiments, an improvement of clinical benefit rate (CBR=CR+PR+SD≧6 months) is obtained as compared to without the PARP inhibitor. In some embodiments, the clinical benefit rate is at least about 30%. In some embodiments, two or more of the therapeutic compounds are administered to the patient in a single dosage form. In some embodiments, the PARP inhibitor is a PARP-1 inhibitor. In other embodiments, the PARP inhibitor is a benzamide or a metabolite thereof. In some embodiments, the benzamide is 4-iodo-3-nitrobenzamide or a metabolite thereof. In some embodiments, the breast cancer is a metastatic breast cancer. In some embodiments, the breast cancer is an ER-negative metastatic breast cancer. In some embodiments, the breast cancer is a PR-negative metastatic breast cancer. In some embodiments, the breast cancer is a HER2-negative metastatic breast cancer. In some embodiments, the breast cancer is ER-negative and PR-negative. In some embodiments, the breast cancer is ER-negative and HER2-negative. In some embodiments, the breast cancer is PR-negative and HER2-negative. In some embodiments, the breast cancer is ER-negative, PR-negative and HER2-negative. In some embodiments, the treatment comprises selecting treatment cycle of at least 11 days and on days 1, 4, 8 and 11 of the cycle, the patient receives about 10 to about 100 mg/kg of 4-iodo-3-nitrobenzamide or a molar equivalent of a metabolite thereof. In some embodiments, the 4-iodo-3-nitrobenzamide is administered orally or as an intravenous infusion.

Some embodiments provide a method of treating breast cancer in a patient, comprising: (a) testing a sample from the patient for PARP expression; and (b) if the PARP expression exceeds a predetermined level, administering to the patient at least one PARP inhibitor. In some embodiments, at least one therapeutic effect is obtained, said at least one therapeutic effect being reduction in size of a breast tumor, reduction in metastasis, complete remission, partial remission, pathologic complete response, or stable disease. In some embodiments, an improvement of clinical benefit rate (CBR=CR+PR+SD≧6 months) is obtained as compared to treatment without the PARP inhibitor. In some embodiments, the improvement of clinical benefit rate is at least about 30%. In some embodiments, the PARP inhibitor is a PARP-1 inhibitor. In other embodiments, the PARP inhibitor is a benzamide or a metabolite thereof. In some embodiments, the benzamide is 4-iodo-3-nitrobenzamide or a metabolite thereof. In some embodiments, the breast cancer is a metastatic breast cancer.

In some embodiments, the method further comprises testing a sample from the patient for expression of estrogen receptor, progesterone receptor or human epidermal growth factor 2 receptor. In some embodiments, the breast cancer is HR-negative breast cancer. In some embodiments, the breast cancer is an ER-negative breast cancer. In some embodiments, the breast cancer is a PR-negative breast cancer. In some embodiments, the breast cancer is a HER2-negative breast cancer. In some embodiments, the breast cancer is ER-negative and PR-negative. In some embodiments, the breast cancer is ER-negative and HER2-negative. In some embodiments, the breast cancer is PR-negative and HER2-negative. In some embodiments, the breast cancer is ER-negative, PR-negative and HER2-negative. In some embodiments, the treatment comprises selecting a treatment cycle of at least 11 days and on days 1, 4, 8 and 11 of the cycle, the patient receives about 10 to about 100 mg/kg of 4-iodo-3-nitrobenzamide or a molar equivalent of a metabolite thereof. In some embodiments, the 4-iodo-3-nitrobenzamide is administered orally or as an intravenous infusion.

Some embodiments disclosed herein provide a method of treating breast cancer in a patient in need of such treatment, comprising: (a) obtaining a sample from the patient; (b) testing the sample to determine each of the following: (i) whether the cancer is ER-positive or -negative; (ii) whether the cancer is PR-positive or -negative; and (iii) whether the cancer is HER2-positive or -negative; (c) if two or more of the following conditions are met, treating the patient with a combination of therapeutic agents, wherein the therapeutic agents include at least one antimetabolite, at least one platinum complex and at least one PARP inhibitor: (i) the cancer is ER-negative, (ii) the cancer is PR-negative, or (iii) the cancer is HER2-negative; and (d) if two or more of conditions (i)-(iii) are not met, selecting a different treatment option. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Some embodiments described herein provide a method of treating ER-negative, PR-negative, HER-2 negative metastatic breast cancer in a patient in need of such treatment, comprising administering to said patient at least one antimetabolite, at least one platinum complex and at least one PARP inhibitor. In some embodiments, an improvement of clinical benefit rate (CBR=CR+PR+SD≧6 months) is obtained as compared to treatment with the antimetabolite and platinum complex but without the PARP inhibitor. In some embodiments, the clinical benefit rate is at least about 60%. In some embodiments, two or more of the therapeutic compounds are administered to the patient in a single dosage form. In some embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaplatin and oxaliplatin. In some embodiments, the platinum complex is carboplatin. In some embodiments, the antimetabolite is a citabine. In some embodiments, the antimetabolite is selected from the group consisting of citabine, capecitabine, gemcitabine and valopicitabine. In some embodiments, the antimetabolite is gemcitabine. In some embodiments, the method further comprises administering a taxane to the patient. In some embodiments, the taxane is paclitaxel or docetaxel. In some embodiments, the breast cancer is a metastatic breast cancer. In some embodiments, the breast cancer is at stage I, II or III. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is an ER-negative metastatic breast cancer. In some embodiments, the breast cancer is a PR-negative metastatic breast cancer. In some embodiments, the breast cancer is a HER2-negative metastatic breast cancer. In some embodiments, the breast cancer is ER-negative and PR-negative. In some embodiments, the breast cancer is ER-negative and HER2-negative. In some embodiments, the breast cancer is PR-negative and HER2-negative. In some embodiments, the breast cancer is ER-negative, PR-negative and HER2-negative. In some embodiments, the treatment comprises selecting treatment cycle of at least 11 days and: (a) on days 1 and 8 of the cycle, the patient receives about 100-2000 mg/m$^2$ gemcitabine; (b) on days 1 and 8 of the cycle, the patient receives about 10 to about 400 mg/m$^2$ of carboplatin; and (c) on days 1, 4, 8 and 11 of the cycle, the patient receives about 10 to about 100 mg/kg of 4-iodo-3-nitrobenzamide or a molar equivalent of a metabolite thereof. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Some embodiments provide a method of treating breast cancer in a patient, comprising: (a) testing a sample from the patient for PARP expression; and (b) if the PARP expression exceeds a predetermined level, administering to the patient at least one antimetabolite, at least one platinum complex and at least one PARP inhibitor. In some embodiments, at least one therapeutic effect is obtained, said at least one therapeutic effect being reduction in size of a breast tumor, reduction in metastasis, complete remission, partial remission, pathologic complete response, or stable disease. In some embodiments, an improvement of clinical benefit rate (CBR=CR+PR+SD≧6 months) is obtained as compared to treatment with the antimetabolite and platinum complex but without the PARP inhibitor. In some embodiments, the improvement of clinical benefit rate is at least about 60%. In some embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaplatin and oxaliplatin. In some embodiments, the platinum complex is carboplatin. In some embodiments, the antimetabolite is a citabine. In some embodiments, the antimetabolite is selected from the group consisting of citabine, capecitabine, gemcitabine and valopicitabine. In some embodiments, the antimetabolite is gemcitabine. In some embodiments, the method further comprises administering a taxane to the patient. In some embodiments, the taxane is paclitaxel or docetaxel. In some embodiments, the breast cancer is a metastatic breast cancer. In some embodiments, the method further comprises testing a sample from the patient for expression of estrogen receptor, progesterone receptor or human epidermal growth factor 2 receptor. In some embodiments, the breast cancer is negative for at least one of: ER, PR or HER2. In some embodiments, the breast cancer is negative for at least one of: ER, PR or HER2; and the breast cancer is positive for at least one of ER, PR or HER2. In some embodiments, the breast cancer is HR-negative breast cancer. In some embodiments, the breast cancer is an ER-negative breast cancer. In some embodiments, the breast cancer is a PR-negative breast cancer. In some embodiments, the breast cancer is a HER2-negative breast cancer. In some embodiments, the breast cancer is ER-negative and PR-negative. In some embodiments, the breast cancer is ER-negative and HER2-negative. In some embodiments, the breast cancer is PR-negative and HER2-negative. In some embodiments, the breast cancer is ER-negative, PR-negative and HER2-negative. In some embodiments, the treatment comprises selecting a treatment cycle of at least 11 days and: (a) on days 1 and 8 of the cycle, the patient receives about 100-2000 mg/m$^2$ gemcitabine; (b) on days 1 and 8 of the cycle, the patient receives about 10 to about 400 mg/m$^2$ of carboplatin; and (c) on days 1, 4, 8 and 11 of the cycle, the patient receives about 10 to about 100 mg/kg of 4-iodo-3-nitrobenzamide or a molar equivalent of a metabolite thereof. In some embodiments, the gemcitabine is administered as an intravenous infusion. In some embodiments, the carboplatin is administered as an intravenous infusion. In some embodiments, the 4-iodo-3-nitrobenzamide is administered orally or as an intravenous infusion.

Thus, embodiments provided herein comprise treating a patient with at least three chemically distinct substances, one of which is an antimetabolite, one of which is a platinum-containing complex and one of which is a PARP inhibitor. In some embodiments, one or more of these substances may be capable of being present in a variety of physical forms—e.g. free base, salts (especially pharmaceutically acceptable salts), hydrates, polymorphs, solvates, metabolites, etc. Unless otherwise qualified herein, use of a chemical name is intended to encompass all physical forms of the named chemical. For example, recitation of 4-iodo-3-nitrobenzamide, without further qualification, is intended to generically encompass the free base as well as all pharmaceutically acceptable salts, polymorphs, hydrates, metabolites, etc. Where it is intended to limit the disclosure or claims to a particular physical form of a compound, this will be clear from the context of the passage or claim in which the reference to the compound appears.

In some embodiments, the present disclosure provides a method of treating breast cancer, comprising administering to the patient at least one taxane, at least one platinum complex and at least one PARP inhibitor. In some embodiments, at least one therapeutic effect is obtained, said at least one therapeutic effect being reduction in size of a breast tumor, reduction in metastasis, complete remission, partial remission, pathologic complete response, or stable disease. In some embodiments, the PARP inhibitor is a benzamide or a metabolite thereof. In some embodiments, the benzamide is 4-iodo-3-nitrobenzamide or a metabolite thereof. In some embodiments, the platinum complex is selected from the group consisting of cisplatin, carboplatin, oxaplatin and oxaliplatin. In some embodiments, the platinum complex is carboplatin. In some embodiments, the taxane is paclitaxel or docetaxel. In some embodiments, the taxane is paclitaxel. In some embodiments, the method comprises, during a treatment cycle of at least 11 days: (a) on day 1 of the cycle, administering to the patient about 10-200 mg/m$^2$ of paclitaxel; (b) on day 1 of the cycle, administering to the patient about 10-400 mg/m$^2$ carboplatin; and (c) on day 1 and twice weekly throughout the cycle, administering to the patient about 1-100 mg/kg of 4-iodo-3-nitrobenzamide or a molar equivalent of a metabolite thereof.

In some embodiments, the disclosure herein provides a method of treating breast cancer in a patient, comprising: (a) obtaining a sample from the patient; (b) testing the sample to determine a level of PARP expression in the sample; (c) determining whether the PARP expression exceeds a predetermined level, and if so, administering to the patient at least one taxane, at least one platinum complex and at least one PARP inhibitor. In some embodiments, the method further comprises optionally selecting a different treatment option if the PARP expression in the sample does not exceed the predetermined level. In some embodiments, the cancer is a breast cancer that is negative for one or more hormone receptors. In some embodiments, the cancer is a breast cancer that is negative for HER2. In some embodiments, the cancer is negative for estrogen receptor (ER), progestin receptor (PR) or HER2. In some embodiments, the cancer is positive for at least one hormone receptor or HER2. In some embodiments, the taxane is cisplatin, carboplatin, oxaplatin or oxaliplatin. In some embodiments, the taxane is paclitaxel. In some embodiments, the platinum complex is cisplatin or carboplatin. In some embodiments, the platinum complex is carboplatin. In some embodiments, the PARP inhibitor is a benzamide or a metabolite thereof. In some embodiments, the PARP inhibitor is 4-iodo-3-nitrobenzamide or a metabolite thereof. In some embodiments, the sample is a tumor section or a bodily fluid.

Some embodiments described herein provide a method of treating breast cancer in a patient, comprising during a 21 day treatment cycle: (a) on day 1 of the cycle, administering to the patient about 750 mg/m$^2$ of paclitaxel; (b) on day 1 of the cycle, administering to the patient about 10-400 mg/m$^2$ of carboplatin; and (c) on day 1 of the cycle, and twice weekly thereafter, administering to the patient about 1-100 mg/kg of 4-iodo-3-nitrobenzamide. In some embodiments, the paclitaxel is administered as an intravenous infusion. In some embodiments, the carboplatin is administered as an intravenous infusion. In some embodiments, the 4-iodo-3-nitrobenzamide is administered orally or as an intravenous infusion.

Some embodiments described herein provide a method of treating breast cancer in a patient, comprising: (a) establishing a treatment cycle of about 10 to about 30 days in length; (b) on from 1 to 5 separate days of the cycle, administering to the patient about 100 to about 2000 mg/m$^2$ of paclitaxel by intravenous infusion over about 10 to about 300 minutes; (c) on from 1 to 5 separate days of the cycle, administering to the patient about 10-400 mg/m$^2$ of carboplatin by intravenous infusion over about 10 to about 300 minutes; and (d) on from 1 to 10 separate days of the cycle, administering to the patient about 1 mg/kg to about 8 mg/kg of 4-iodo-3-nitrobenzamide over about 10 to about 300 minutes.

Thus, embodiments provided herein comprise treating a patient with at least three chemically distinct substances, one of which is a taxane (e.g. paclitaxel or docetaxel), one of which is a platinum-containing complex (e.g. cisplatin or carboplatin or cisplatin) and one of which is a PARP inhibitor (e.g. BA or a metabolite thereof). In some embodiments, one or more of these substances may be capable of being present in a variety of physical forms—e.g. free base, salts (especially pharmaceutically acceptable salts), hydrates, polymorphs, solvates, metabolites, etc. Unless otherwise qualified herein, use of a chemical name is intended to encompass all physical forms of the named chemical. For example, recitation of 4-iodo-3-nitrobenzamide, without further qualification, is intended to generically encompass the free base as well as all pharmaceutically acceptable salts, polymorphs, hydrates, and metabolites thereof. Where it is intended to limit the disclosure or claims to a particular physical form of a compound, this will be clear from the context of the passage or claim in which the reference to the compound appears.

The terms "effective amount" or "pharmaceutically effective amount" refer to a sufficient amount of the agent to provide the desired biological, therapeutic, and/or prophylactic result. That result can be reduction and/or alleviation of the signs, symptoms, or causes of a disease, or any other desired alteration of a biological system. For example, an "effective amount" for therapeutic uses is the amount of a nitrobenzamide compound as disclosed herein per se or a composition comprising the nitrobenzamide compound herein required to provide a clinically significant decrease in a disease. An appropriate effective amount in any individual case may be determined by one of ordinary skill in the art using routine experimentation.

By "pharmaceutically acceptable" or "pharmacologically acceptable" is meant a material which is not biologically or otherwise undesirable, i.e., the material may be administered to an individual without causing significant undesirable biological effects or interacting in a deleterious manner with any of the components of the composition in which it is contained.

The term "treating" and its grammatical equivalents as used herein include achieving a therapeutic benefit and/or a prophylactic benefit. By therapeutic benefit is meant eradication or amelioration of the underlying disorder being treated. For example, in a cancer patient, therapeutic benefit includes eradication or amelioration of the underlying cancer. Also, a therapeutic benefit is achieved with the eradication or amelioration of one or more of the physiological symptoms associated with the underlying disorder such that an improvement is observed in the patient, notwithstanding the fact that the patient may still be afflicted with the underlying disorder. For prophylactic benefit, a method of the invention may be performed on, or a composition of the invention administered to a patient at risk of developing cancer, or to a patient reporting one or more of the physiological symptoms of such conditions, even though a diagnosis of the condition may not have been made.

Anti-Tumor Agents

Anti-tumor agents that may be used in the present invention include but are not limited to antitumor alkylating agents, antitumor antimetabolites, antitumor antibiotics, plant-derived antitumor agents, antitumor platinum-complex, antitumor camptothecin derivatives, antitumor tyrosine kinase inhibitors, monoclonal antibodies, interferons, biological response modifiers, and other agents that exhibit anti-tumor activities, or a pharmaceutically acceptable salt thereof.

In some embodiments, the anti-tumor agent is an alkylating agent. The term "alkylating agent" herein generally refers to an agent giving an alkyl group in the alkylation reaction in which a hydrogen atom of an organic compound is substituted with an alkyl group. Examples of anti-tumor alkylating agents include but are not limited to nitrogen mustard N-oxide, cyclophosphamide, ifosfamide, melphalan, busulfan, mitobronitol, carboquone, thiotepa, ranimustine, nimustine, temozolomide or carmustine.

In some embodiments, the anti-tumor agent is an antimetabolite. The term "antimetabolite" used herein includes, in a broad sense, substances which disturb normal metabolism and substances which inhibit the electron transfer system to prevent the production of energy-rich intermediates, due to their structural or functional similarities to metabolites that are important for living organisms (such as vitamins, coenzymes, amino acids and saccharides). Examples of antimetabolites that have anti-tumor activities include but are not limited to methotrexate, 6-mercaptopurine riboside, mercaptopurine, 5-fluorouracil, tegafur, doxifluridine, carmofur, cytarabine, cytarabine ocfosfate, enocitabine, S-1, gemcitabine, fludarabine or pemetrexed disodium, and preferred are 5-fluorouracil, S-1, gemcitabine and the like.

In some embodiments, the anti-tumor agent is an antitumor antibiotic. Examples of antitumor antibiotics include but are not limited to actinomycin D, doxorubicin, daunorubicin, neocarzinostatin, bleomycin, peplomycin, mitomycin C, aclarubicin, pirarubicin, epirubicin, zinostatin stimalamer, idarubicin, sirolimus or valrubicin.

In some embodiments, the anti-tumor agent is a plant-derived antitumor agent. Examples of plant-derived antitumor agents include but are not limited to vincristine, vinblastine, vindesine, etoposide, sobuzoxane, docetaxel, paclitaxel and vinorelbine, and preferred and docetaxel and paclitaxel.

In some embodiments, the anti-tumor agent is a camptothecin derivative that exhibits anti-tumor activities. Examples of anti-tumor camptothecin derivatives include but are not limited to camptothecin, 10-hydroxycamptothecin, topotecan, irinotecan or 9-aminocamptothecin, with camptothecin, topotecan and irinotecan being preferred. Further, irinotecan is metabolized in vivo and exhibits antitumor effect as SN-38. The action mechanism and the activity of the camptothecin derivatives are believed to be virtually the same as those of camptothecin (e.g., Nitta, et al., Gan to Kagaku Ryoho, 14, 850-857 (1987)).

In some embodiments, the anti-tumor agent is an organoplatinum compound or a platinum coordination compound having antitumor activity. Organoplatinum compound herein refers to a platinum containing compound which provides platinum in ion form. Preferred organoplatinum compounds include but are not limited to cisplatin; cis-diamminediaquoplatinum (II)-ion; chloro(diethylenetriamine)-platinum (II) chloride; dichloro(ethylenediamine)-platinum (II); diammine(1,1-cyclobutanedicarboxylato) platinum (II) (carboplatin); spiroplatin; iproplatin; diammine(2-ethylmalonato) platinum (II); ethylenediaminemalonatoplatinum (II); aqua(1,2-diaminodicyclohexane)sulfatoplatinum (II); aqua(1,2-diaminodicyclohexane)malonatoplatinum (II); (1,2-diaminocyclohexane)malonatoplatinum (II); (4-carboxyphthalato)(1,2-diaminocyclohexane) platinum (II); (1,2-diaminocyclohexane)-(isocitrato)platinum (II); (1,2-diaminocyclohexane)oxalatoplatinum (II); ormaplatin; tetraplatin; carboplatin, nedaplatin and oxaliplatin, and preferred is carboplatin or oxaliplatin. Further, other antitumor organoplatinum compounds mentioned in the specification are known and are commercially available and/or producible by a person having ordinary skill in the art by conventional techniques.

In some embodiments, the anti-tumor agent is an antitumor tyrosine kinase inhibitor. The term "tyrosine kinase inhibitor" herein refers to a chemical substance inhibiting "tyrosine kinase" which transfers a λ-phosphate group of ATP to a hydroxyl group of a specific tyrosine in protein. Examples of anti-tumor tyrosine kinase inhibitors include but are not limited to gefitinib, imatinib, erlotinib, Sutent, Nexavar, Recentin, ABT1-869, and Axitinib.

In some embodiments, the anti-tumor agent is an antibody or a binding portion of an antibody that exhibits anti-tumor activity. In some embodiments, the anti-tumor agent is a monoclonal antibody. Examples thereof include but are not limited to abciximab, adalimumab, alemtuzumab, basiliximab, bevacizumab, cetuximab, daclizumab, eculizumab, efalizumab, ibritumomab, tiuxetan, infliximab, muromonab-CD3, natalizumab, omalizumab, palivizumab, panitumumab, ranibizumab, gemtuzumab ozogamicin, rituximab, tositumomab, trastuzumab, or any antibody fragments specific for antigens.

In some embodiments, the anti-tumor agent is an interferon. Such interferon has antitumor activity, and it is a glycoprotein which is produced and secreted by most animal cells upon viral infection, it has not only the effect of inhibiting viral growth but also various immune effector mechanisms including inhibition of growth of cells (in particular, tumor cells) and enhancement of the natural killer cell activity, thus being designated as one type of cytokine. Examples of anti-tumor interferons include but are not limited to interferon α, interferon α-2a, interferon α-2b, interferon β, interferon γ-1a and interferon γ-n1.

In some embodiments, the anti-tumor agent is a biological response modifier. It is generally the generic term for substances or drugs for modifying the defense mechanisms of living organisms or biological responses such as survival, growth or differentiation of tissue cells in order to direct them to be useful for an individual against tumor, infection or other diseases. Examples of the biological response modifier include but are not limited to krestin, lentinan, sizofuran, picibanil and ubenimex.

In some embodiments, the anti-tumor agents include but are not limited to mitoxantrone, L-asparaginase, procarbazine, dacarbazine, hydroxycarbamide, pentostatin, tretinoin, alefacept, darbepoetin alfa, anastrozole, exemestane, bicalutamide, leuprorelin, flutamide, fulvestrant, pegaptanib octasodium, denileukin diftitox, aldesleukin, thyrotropin alfa, arsenic trioxide, bortezomib, capecitabine, and goserelin.

The above-described terms "antitumor alkylating agent", "antitumor antimetabolite", "antitumor antibiotic", "plant-derived antitumor agent", "antitumor platinum coordination compound", "antitumor camptothecin derivative", "antitumor tyrosine kinase inhibitor", "monoclonal antibody", "interferon", "biological response modifier" and "other antitumor agent" are all known and are either commercially available or producible by a person skilled in the art by methods known per se or by well-known or conventional methods. The process for preparation of gefitinib is described, for example, in U.S. Pat. No. 5,770,599; the process for preparation of cetuximab is described, for example, in WO 96/40210; the process for preparation of bevacizumab is described, for example, in WO 94/10202; the process for preparation of oxaliplatin is described, for example, in U.S. Pat. Nos. 5,420,319 and 5,959,133; the process for preparation of gemcitabine is described, for example, in U.S. Pat. Nos. 5,434,254 and 5,223,608; and the process for preparation of camptothecin is described in U.S. Pat. Nos. 5,162,532, 5,247,089, 5,191,082, 5,200,524, 5,243,050 and 5,321,140; the process for preparation of irinotecan is described, for example, in U.S. Pat. No. 4,604,463; the process for preparation of topotecan is described, for example, in U.S. Pat. No. 5,734,056; the process for preparation of temozolomide is described, for example, in JP-B No. 4-5029; and the process for preparation of rituximab is described, for example, in JP-W No. 2-503143.

The above-mentioned antitumor alkylating agents are commercially available, as exemplified by the following: nitrogen mustard N-oxide from Mitsubishi Pharma Corp. as Nitrorin (tradename); cyclophosphamide from Shionogi & Co., Ltd. as Endoxan (tradename); ifosfamide from Shionogi & Co., Ltd. as Ifomide (tradename); melphalan from GlaxoSmithKline Corp. as Alkeran (tradename); busulfan from Takeda Pharmaceutical Co., Ltd. as Mablin (tradename); mitobronitol from Kyorin Pharmaceutical Co., Ltd. as Myebrol (tradename); carboquone from Sankyo Co., Ltd. as Esquinon (tradename); thiotepa from Sumitomo Pharmaceutical Co., Ltd. as Tespamin (tradename); ranimustine from Mitsubishi Pharma Corp. as Cymerin (tradename); nimustine from Sankyo Co., Ltd. as Nidran (tradename); temozolomide from Schering Corp. as Temodar (tradename); and carmustine from Guilford Pharmaceuticals Inc. as Gliadel Wafer (tradename).

The above-mentioned antitumor antimetabolites are commercially available, as exemplified by the following: methotrexate from Takeda Pharmaceutical Co., Ltd. as Methotrexate (tradename); 6-mercaptopurine riboside from Aventis Corp. as Thioinosine (tradename); mercaptopurine from Takeda Pharmaceutical Co. Ltd. as Leukerin (tradename); 5-fluorouracil from Kyowa Hakko Kogyo Co., Ltd. as 5-FU (tradename); tegafur from Taiho Pharmaceutical Co., Ltd. as Futraful (tradename); doxyfluridine from Nippon Roche Co., Ltd. as Furutulon (tradename); cannofur from Yamanouchi Pharmaceutical Co., Ltd. as Yamafur (tradename); cytarabine from Nippon Shinyaku Co., Ltd. as Cylocide (tradename); cytarabine ocfosfate from Nippon Kayaku Co., Ltd. as Strasid (tradename); enocitabine from Asahi Kasei Corp. as Sanrabin (tradename); S-1 from Taiho Pharmaceutical Co., Ltd. as TS-1 (tradename); gemcitabine from Eli Lilly & Co. as Gemzar (tradename); fludarabine from Nippon Schering Co., Ltd. as Fludara (tradename); and pemetrexed disodium from Eli Lilly & Co. as Alimta (tradename).

The above-mentioned antitumor antibiotics are commercially available, as exemplified by the following: actinomycin D from Banyu Pharmaceutical Co., Ltd. as Cosmegen (tradename); doxorubicin from Kyowa Hakko Kogyo Co., Ltd. as adriacin (tradename); daunorubicin from Meiji Seika Kaisha Ltd. as Daunomycin; neocarzinostatin from Yamanouchi Pharmaceutical Co., Ltd. as Neocarzinostatin (tradename); bleomycin from Nippon Kayaku Co., Ltd. as Bleo (tradename); pepromycin from Nippon Kayaku Co, Ltd. as Pepro (tradename); mitomycin C from Kyowa Hakko Kogyo Co., Ltd. as Mitomycin (tradename); aclarubicin from Yamanouchi Pharmaceutical Co., Ltd. as Aclacinon (tradename); pirarubicin from Nippon Kayaku Co., Ltd. as Pinorubicin (tradename); epirubicin from Pharmacia Corp. as Pharmorubicin (tradename); zinostatin stimalamer from Yamanouchi Pharmaceutical Co., Ltd. as Smancs (tradename); idarubicin from Pharmacia Corp. as Idamycin (tradename); sirolimus from Wyeth Corp. as Rapamune (tradename); and valrubicin from Anthra Pharmaceuticals Inc. as Valstar (tradename).

The above-mentioned plant-derived antitumor agents are commercially available, as exemplified by the following: vincristine from Shionogi & Co., Ltd. as Oncovin (tradename); vinblastine from Kyorin Pharmaceutical Co., Ltd. as Vinblastine (tradename); vindesine from Shionogi & Co., Ltd. as Fildesin (tradename); etoposide from Nippon Kayaku Co., Ltd. as Lastet (tradename); sobuzoxane from Zenyaku Kogyo Co., Ltd. as Perazolin (tradename); docetaxel from Aventis Corp. as Taxsotere (tradename); paclitaxel from Bristol-Myers Squibb Co. as Taxol (tradename); and vinorelbine from Kyowa Hakko Kogyo Co., Ltd. as Navelbine (tradename).

The above-mentioned antitumor platinum coordination compounds are commercially available, as exemplified by the following: cisplatin from Nippon Kayaku Co., Ltd. as Randa (tradename); carboplatin from Bristol-Myers Squibb Co. as Paraplatin (tradename); nedaplatin from Shionogi & Co., Ltd. as Aqupla (tradename); and oxaliplatin from Sanofi-Synthelabo Co. as Eloxatin (tradename).

The above-mentioned antitumor camptothecin derivatives are commercially available, as exemplified by the following: irinotecan from Yakult Flonsha Co. Ltd. as Campto (tradename); topotecan from GlaxoSmithKline Corp. as Hycamtin (tradename); and camptothecin from Aldrich Chemical Co., Inc., U.S.A.

The above-mentioned antitumor tyrosine kinase inhibitors are commercially available, as exemplified by the following: gefitinib from AstraZeneca Corp. as Iressa (tradename); imatinib from Novartis AG as Gleevec (tradename); and erlotinib from OSI Pharmaceuticals Inc. as Tarceva (tradename).

The above-mentioned monoclonal antibodies are commercially available, as exemplified by the following: cetuximab from Bristol-Myers Squibb Co. as Erbitux (tradename); bevacizumab from Genentech, Inc. as Avastin (tradename); rituximab from Biogen Idec Inc. as Rituxan (tradename); alemtuzumab from Berlex Inc. as Campath (tradename); and trastuzumab from Chugai Pharmaceutical Co., Ltd. as Herceptin (tradename).

The above-mentioned interferons are commercially available, as exemplified by the following: interferon a from Sumitomo Pharmaceutical Co., Ltd. as Sumiferon (tradename); interferon $\alpha$-2a from Takeda Pharmaceutical Co., Ltd. as Canferon-A (tradename); interferon $\alpha$-2b from Schering-Plough Corp. as Intron A (tradename); interferon $\beta$ from Mochida Pharmaceutical Co., Ltd. as IFN.beta. (tradename); interferon $\gamma$-1a from Shionogi & Co., Ltd. as Immunomax-$\gamma$ (tradename); and interferon $\gamma$-n1 from Otsuka Pharmaceutical Co., Ltd. as Ogamma (tradename).

The above-mentioned biological response modifiers are commercially available, as exemplified by the following: krestin from Sankyo Co., Ltd. as krestin (tradename); lentinan from Aventis Corp. as Lentinan (tradename); sizofuran from Kaken Seiyaku Co., Ltd. as Sonifuran (tradename); picibanil from Chugai Pharmaceutical Co., Ltd. as Picibanil (tradename); and ubenimex from Nippon Kavaku Co., Ltd. as Bestatin (tradename).

The above-mentioned other antitumor agents are commercially available, as exemplified by the following: mitoxantrone from Wyeth Lederle Japan, Ltd. as Novantrone (tradename); L-asparaginase from Kyowa Hakko Kogyo Co., Ltd. as Leunase (tradename); procarbazine from Nippon Roche Co., Ltd. as Natulan (tradename); dacarbazine from Kyowa Hakko Kogyo Co., Ltd. as Dacarbazine (tradename); hydroxycarbamide from Bristol-Myers Squibb Co. as Hydrea (tradename); pentostatin from Kagaku Oyobi Kessei Ryoho Kenkyusho as Coforin (tradename); tretinoin from Nippon Roche Co., Ltd. As Vesanoid (tradename); alefacept from Biogen Idec Inc. as Amevive (tradename); darbepoetin alfa from Amgen Inc. as Aranesp (tradename); anastrozole from AstraZeneca Corp. as Arimidex (tradename); exemestane from Pfizer Inc. as Aromasin (tradename); bicalutamide from AstraZeneca Corp. as Casodex (tradename); leuprorelin from Takeda Pharmaceutical Co. Ltd. as Leuplin (tradename); flutamide from Schering-Plough Corp. as Eulexin (tradename); fulvestrant from AstraZeneca Corp. as Faslodex (tradename); pegaptanib octasodium from Gilead Sciences, Inc. as Macugen (tradename); denileukin diftitox from Ligand Pharmaceuticals Inc. as Ontak (tradename); aldesleukin from Chiron Corp. as Proleukin (tradename); thyrotropin alfa from Genzyme Corp. as Thyrogen (tradename); arsenic trioxide from Cell Therapeutics, Inc. as Trisenox (tradename); bortezomib from Millennium Pharmaceuticals, Inc. as Velcade (tradename); capecitabine from Hoffmann-La Roche, Ltd. as Xeloda (tradename); and goserelin from AstraZeneca Corp. as Zoladex (tradename). The term "antitumor agent" as used in the specification includes the above-described antitumor alkylating agent, antitumor antimetabolite, antitumor antibiotic, plant-derived antitumor agent, antitumor platinum coordination compound, antitumor camptothecin derivative, antitumor tyrosine kinase inhibitor, monoclonal antibody, interferon, biological response modifier, and other antitumor agents.

Other anti-tumor agents or anti-neoplastic agents can be used in combination with benzopyrone compounds. Such suitable anti-tumor agents or anti-neoplastic agents include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane, Actinomycin-D, Adriamycin, Adrucil, Agrylin, Ala-Cort, Aldesleukin. Alemtuzumab, ALIMTA, Alitretinoin, Alkaban-AQ, Alkeran, All-transretinoic Acid, Alpha Interferon, Altretamine, Amethopterin, Amifostine, Aminoglutethimide, Anagrelide, Anandron, Anastrozole, Arabinosylcvtosine, Ara-C, Aranesp, Aredia, Arimidex. Aromasin, Arranon, Arsenic Trioxide, Asparaginase, ATRA, Avastin, Azacitidine, BCG, BCNU, Bendamustine, Bevacizumab, Bexarotene, BEXXAR. Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine Wafer, Casodex, CC-5013, CCl-779, CCNU, CDDP, CeeNU, Cerubidine, Cetuximab, Chlorambucil, Cisplatin, Citrovorum Factor, Cladribine, Cortisone, Cosmegen, CPT-11, Cyclophosphamide, Cytadren, Cytarabine, Cytarabine Liposomal, Cytosar-U, Cytoxan, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome, Decadron, Decitabine, Delta-Cortef, Deltasone, Denileukin Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil, Doxorubicin, Doxorubicin Liposomal, Droxia™, DTIC, DTIC-Dome, Duralone, Efudex, Eligard, Ellence, Eloxatin, Elspar, Emcyt, Epirubicin, Epoetin Alfa, Erbitux, Erlotinib, Erwinia L-asparaginase, Estramustine, Ethyol, Etopophos, Etoposide, Etoposide Phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR Fulvestrant, G-CSF, Gefitinib, Gemcitabine, Gemtuzumab ozogamicin, Gemzar & Gemzar Side Effects—Chemotherapy Drugs, Gleevec, Gliadel Wafer, GM-CSF, Goserelin, Granulocyte—Colony Stimulating Factor, Granulocyte Macrophage Colony Stimulating Factor, Halotestin, Herceptin, Hexadrol, Hexylen, Hexamethylmelamine, HMM, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin, Idarubicin, Ifex IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A (interferon alfa-2b), Iressa, Irinotecan, Isotretinoin, Ixabepilone, Ixempra, Kidrolase (t), Lanacort, Lapatinib, L-asparaginase, LCR, Lenalidomide, Letrozole, Leucovorin, Leukeran, Leukine, Leuprolide, Leurocristine, Leustatin, Liposomal Ara-C, Liquid Pred, Lomustine, L-PAM, L-Sarcolysin, Lupron, Lupron Depot, Matulane, Maxidex, Mechlorethamine, Mechlorethamine Hydrochloride, Medralone, Medrol, Megace, Megestrol, Megestrol Acetate, Melphalan, Mercaptopurine, Mesna, Mesnex, Methotrexate, Methotrexate Sodium, Methylprednisolone, Meticorten, Mitomycin, Mitomycin-C, Mitoxantrone, M-Prednisol, MTC, MTX, Mustargen, Mustine, Mutamycin, Myleran, Mylocel, Mylotarg, Navelbine, Nelarabine, Neosar, Neulasta, Neumega, Neupogen, Nexavar, Nilandron, Nilutamide, Nipent, Nitrogen Mustard, Novaldex, Novantrone, Octreotide, Octreotide acetate, Oncospar, Oncovin, Ontak, Onxal, Oprevelkin, Orapred. Orasone, Oxaliplatin, Paclitaxel, Paclitaxel Protein-bound, Pamidronate, Panitumumab, Panretin, Paraplatin, Pediapred, PEG Interferon, Pegaspargase, Pegfilgrastim, PEG-INTRON, PEG-L-asparaginase, PEMETREXED, Pentostatin, Phenylalanine Mustard, Platinol, Platinol-AQ, Prednisolone, Prednisone, Prelone, Procarbazine, PROCRIT, Proleukin, Prolifeprospan 20 with Carmustine Implant, Purinethol, Raloxifene, Revilmid, Rheumatrex, Rituxan, Rituximab, Roferon-A (Interferon Alfa-2a), Rubex, Rubidomycin hydrochloride, Sandostatin, Sandostatin LAR, Sargramostim, Solu-Cortef, Solu-Medrol, Sorafenib, SPRYCEL, STI-571, Streptozocin, SUI 1248, Sunitinib, Sutent, Tamoxifen, Tarceva, Targretin, Taxol, Taxotere, Temodar, Temozolomide, Temsirolimus, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Torisel, Tositumomab, Trastuzumab, Tretinoin, Trexall™, Trisenox, TSPA, TYKERB, VCR, Vectibix, Vectibix, Velban, Velcade, VePesid, Vesanoid, Viadur, Vidaza, Vinblastine, Vinblastine Sulfate, Vincasar Pfs, Vincristine, Vinorelbine, Vinorelbine tartrate, VLB, VM-26, Vorinostat, VP-16, Vumon, Xeloda, Zanosar, Zevalin, Zinecard, Zoladex, Zoledronic acid, Zolinza, Zometa.

Antimetabolites:

Antimetabolites are drugs that interfere with normal cellular metabolic processes. Since cancer cells are rapidly replicating, interference with cellular metabolism affects cancer cells to a greater extent than host cells. Gemcitabine (4-amino-1-[3,3-difluoro-4-hydroxy-5-(hydroxymethyl) tetrahydrofuran-2-yl]-1H-pyrimidin-2-one; marketed as GEMZAR® by Eli Lilly and Company) is a nucleoside analog, which interferes with cellular division by blocking DNA synthesis, thus resulting in cell death, apparently through an apoptotic mechanism. The dosage of gemcitabine may be adjusted to the particular patient. In adults, the dosage of gemcitabine, when used in combination with a platinum agent and a PARP inhibitor, will be in the range of about 100 mg/m$^2$ to about 5000 mg/m$^2$, in the range of about 100 mg/m$^2$ to about 2000 mg/m$^2$, in the range of about 750 to about 1500 mg/m$^2$, about 900 to about 1400 mg/m$^2$ or about 1250 mg/m$^2$. The dimensions mg/m$^2$ refer to the amount of gemcitabine in milligrams (mg) per unit surface area of the patient in square meters (m$^2$). Gemcitabine may be administered by intravenous (IV) infusion, e.g. over a period of about 10 to about 300 minutes, about 15 to about 180 minutes, about 20 to about 60 minutes or about 10 minutes. The term "about" in this context indicates the normal usage of approximately; and in some embodiments indicates a tolerance of ±10% or ±5%.

Platinum Complexes:

Platinum complexes are pharmaceutical compositions used to treat cancer, which contain at least one platinum center complexed with at least one organic group. Carboplatin ((SP-4-2)-Diammine[1,1-cyclobutanedicarboxylato (2-)-O, O' platinum), like cisplatin and oxaliplatin, is a DNA alkylating agent. The dosage of carboplatin is determined by calculating the area under the blood plasma concentration curve (AUC) by methods known to those skilled in the cancer chemotherapy art, taking into account the patient's creatinine clearance rate. In some embodiments, the dosage of carboplatin for combination treatment along with an antimetabolite (e.g. gemcitabine) and a PARP inhibitor (e.g. 4-iodo-3-nitrobenzamide) is calculated to provide an AUC of about 0.1-6 mg/ml min, about 1-3 mg/ml min, about 1.5 to about 2.5 mg/ml min, about 1.75 to about 2.25 mg/ml min or about 2 mg/ml min. (AUC 2, for example, is shorthand for 2 mg/ml min.) In some embodiments, the dosage of carboplatin for combination treatment along with a taxane (e.g. paclitaxel or docetaxel), and a PARP inhibitor (e.g. 4-iodo-3-nitrobenzamide) is calculated to provide an AUC of about 0.1-6 mg/ml min, about 1-3 mg/ml min. about 1.5 to about 2.5 mg/ml min, about 1.75 to about 2.25 mg/ml min or about 2 mg/ml min. (AUC 2, for example, is shorthand for 2 mg/ml min.) In some embodiments, a suitable carboplatin dose is administered about 10 to about 400 mg/m$^2$, e.g. about 360 mg/m$^2$. Platinum complexes, such as carboplatin, are normally administered intravenously (IV) over a period of about 10 to about 300 minutes, about 30 to about 180 minutes, about 45 to about 120 minutes or about 60 minutes. In this context, the term "about" has its normal meaning of approximately. In some embodiments, about means±10% or ±5%.

Topoisomerase Inhibitors

In some embodiments, the methods of the invention may comprise administering to a patient with breast cancer an effective amount of a PARP inhibitor in combination with a topoisomerase inhibitor, for example, irinotecan or topotecan.

Topoisomerase inhibitors are agents designed to interfere with the action of topoisomerase enzymes (topoisomerase I and II), which are enzymes that control the changes in DNA structure by catalyzing the breaking and rejoining of the phosphodiester backbone of DNA strands during the normal cell cycle. Topoisomerases have become popular targets for cancer chemotherapy treatments. It is thought that topoisomerase inhibitors block the ligation step of the cell cycle, generating single and double stranded breaks that harm the integrity of the genome. Introduction of these breaks subsequently lead to apoptosis and cell death. Topoisomerase inhibitors are often divided according to which type of enzyme it inhibits. Topoisomerase I, the type of topoisomerase most often found in eukaryotes, is targeted by topotecan, irinotecan, lurtotecan and exatecan, each of which is commercially available. Topotecan is available from GlaxoSmithKline under the trade name Hycamtim®. Irinotecan is available from Pfizer under the trade name Camptosar®. Lurtotecan may be obtained as a liposomal formulation from Gilead Sciences Inc. Topoisomerase inhibitors may be administered at an effective dose. In some embodiments an effective dose for treatment of a human will be in the range of about 0.01 to about 10 mg/m$^2$/day. The treatment may be repeated on a daily, bi-weekly, semi-weekly, weekly, or monthly basis. In some embodiments, a treatment period may be followed by a rest period of from one day to several days, or from one to several weeks. In combination with a PARP-1 inhibitor, the PARP-1 inhibitor and the topoisomerase inhibitor may be dosed on the same day or may be dosed on separate days.

Compounds that target type II topoisomerase are split into two main classes: topoisomerase poisons, which target the topoisomerase-DNA complex, and topoisomerase inhibitors, which disrupt catalytic turnover. Topo II poisons include but are not limited to eukaryotic type II topoisomerase inhibitors (topo II): amsacrine, etoposide, etoposide phosphate, teniposide and doxorubicin. These drugs are anti-cancer therapies. Examples of topoisomerase inhibitors include ICRF-193. These inhibitors target the N-terminal ATPase domain of topo II and prevent topo II from turning over. The structure of this compound bound to the ATPase domain has been solved by Classen (Proceedings of the National Academy of Science, 2004) showing that the drug binds in a non-competitive manner and locks down the dimerization of the ATPase domain.

Anti-Angiogenic Agents

In some embodiments, the methods of the invention may comprise administering to a patient with breast cancer an effective amount of a PARP inhibitor in combination with an anti-angiogenic agent.

An angiogenesis inhibitor is a substance that inhibits angiogenesis (the growth of new blood vessels). Every solid tumor (in contrast to leukemia) needs to generate blood vessels to keep it alive once it reaches a certain size. Tumors can grow only if they form new blood vessels. Usually, blood vessels are not built elsewhere in an adult body unless tissue repair is actively in process. The angiostatic agent endostatin and related chemicals can suppress the building of blood vessels, preventing the cancer from growing indefinitely. In tests with patients, the tumor became inactive and stayed that way even after the endostatin treatment was finished. The treatment has very few side effects but appears to have very limited selectivity. Other angiostatic agents such as thalidomide and natural plant-based substances are being actively investigated.

Known inhibitors include the drug bevacizumab (Avastin), which binds vascular endothelial growth factor (VEGF), inhibiting its binding to the receptors that promote angiogenesis. Other anti-angiogenic agents include but are not limited to carboxyamidotriazole, TNF-470, CM 101, IFN-alpha, IL-12, platelet factor-4, suramin, SU5416, thrombospondin, angiostatic steroids+heparin, cartilage-derived angiogenesis inhibitory factor, matrix metalloproteinase inhibitors, angiostatin, endostatin, 2-methoxyestradiol, tecogalan, thrombospondin, prolactin, $\alpha_v\beta_3$ inhibitors and linomide.

Her-2 Targeted Therapy

In some embodiments, the methods of the invention may comprise administering to a patient with HER2 positive breast cancer an effective amount of a PARP inhibitor in combination with Herceptin.

Herceptin (trastuzumab) is a targeted therapy for use in early-stage HER2-positive breast cancers. Herceptin is approved for the adjuvant treatment of HER2-overexpressing, node-positive or node-negative (ER/PR-negative or with one high-risk feature) breast cancer. Herceptin can be used several different ways: as part of a treatment regimen including doxorubicin, cyclophosphamide, and either paclitaxel or docetaxel; with docetaxel and carboplatin; or as a single agent following multi-modality anthracycline-based therapy. Herceptin in combination with paclitaxel is approved for the first-line treatment of HER2-overexpressing metastatic breast cancer. Herceptin as a single agent is approved for treatment of HER2-overexpressing breast cancer in patients who have received one or more chemotherapy regimens for metastatic disease.

Lapatinib or lapatinib ditosylate is an orally active chemotherapeutic drug treatment for solid tumours such as breast cancer. During development it was known as small molecule GW572016. Patients who meet specific indication criteria may be prescribed lapatinib as part of combination therapy for breast cancer. Pharmacologically, lapatinib is a dual tyrosine kinase inhibitor that interrupts cancer-causing cellular signals. Lapatinib is used as a treatment for women's breast cancer in patients who have HER2-positive advanced breast cancer that has progressed after previous treatment with other chemotherapeutic agents, such as anthracycline, taxane-derived drugs, or trastuzumab (Herceptin, Genentech).

Hormone Therapy

In some embodiments, the methods of the invention may comprise administering to a patient with breast cancer an effective amount of a PARP inhibitor in combination with hormone therapy.

There are certain hormones that can attach to cancer cells and can affect their ability to multiply. The purpose of hormone therapy is to add, block or remove hormones. With breast cancer, the female hormones estrogen and progesterone can promote the growth of some breast cancer cells. So in these patients, hormone therapy is given to block the body's naturally occurring estrogen and fight the cancer's growth. There are two types of hormone therapy for breast cancer: drugs that inhibit estrogen and progesterone from promoting breast cancer cell growth and drugs or surgery to turn off the production of hormones from the ovaries.

Common hormone therapy drugs used for breast cancer include but are not limited to Tamoxifen, Fareston, Arimidex, Aromasin, Femara, and Zoladex.

Tamoxifen-Hormone Antagonist

Tamoxifen (marketed as Nolvadex) decreases the chance that some early-stage breast cancers will recur and can prevent the development of cancer in the unaffected breast. Tamoxifen also slows or stops the growth of cancer cells present in the body. In addition, tamoxifen may offer an alternative to watchful waiting or prophylactic (preventative) mastectomy to women at high risk for developing breast cancer. Tamoxifen is a type of drug called a selective estrogen-receptor modulator (SERM). At the breast, it functions as an anti-estrogen. Estrogen promotes the growth of breast cancer cells and tamoxifen blocks estrogen from attaching to estrogen receptors on these cells. By doing this, it is believed that the growth of the breast cancer cells will be halted. Tamoxifen is often given along with chemotherapy and other breast cancer treatments. It is considered an option in the following cases: Treatment of ductal carcinoma in situ (DCIS) along with breast-sparing surgery or mastectomy; Adjuvant treatment of lobular carcinoma in situ (LCIS) to reduce the risk of developing more advanced breast cancer; Adjuvant treatment of metastatic breast cancer in men and women whose cancers are estrogen-receptor positive; Treatment of recurrent breast cancer; To prevent breast cancer in women at high risk for developing breast cancer.

Steroidal and Non-Steroidal Aromatase Inhibitor

Aromatase inhibitors (AI) are a class of drugs used in the treatment of breast cancer and ovarian cancer in postmenopausal women that block the aromatase enzyme. Aromatase inhibitors lower the amount of estrogen in post-menopausal women who have hormone-receptor-positive breast cancer. With less estrogen in the body, the hormone receptors receive fewer growth signals, and cancer growth can be slowed down or stopped.

Aromatase inhibitor medications include Arimidex (chemical name: anastrozole), Aromasin (chemical name: exemestane), and Femara (chemical name: letrozole). Each is taken by pill once a day, for up to five years. But for women with advanced (metastatic) disease, the medicine is continued as long as it is working well.

AIs are categorized into two types: irreversible steroidal inhibitors such as exemestane that form a permanent bond with the aromatase enzyme complex; and non-steroidal inhibitors (such as anastrozole, letrozole) that inhibit the enzyme by reversible competition.

Fulvestrant, also known as ICI 182,780, and "Faslodex" is a drug treatment of hormone receptor-positive metastatic breast cancer in postmenopausal women with disease progression following anti-estrogen therapy. It is an estrogen receptor antagonist with no agonist effects, which works both by down-regulating and by degrading the estrogen receptor. It is administered as a once-monthly injection.

Targeted Therapy

In some embodiments, the methods of the invention may comprise administering to a patient with breast cancer an effective amount of a PARP inhibitor in combination with an inhibitor targeting a growth factor receptor including but not limited to epidermal growth factor receptor (EGFR) and insulin-like growth factor 1 receptor (IGF1R).

EGFR is overexpressed in the cells of certain types of human carcinomas including but not limited to lung and breast cancers. Highly proliferating, invasive breast cancer cells often express abnormally high levels of the EGFR, and this is known to control both cell division and migration. The interest in EGFR is further enhanced by the availability and FDA approval of specific EGFR tyrosine kinase inhibitors, for example, Gefitinib. Inhibition of EGFR is an important anti-cancer treatment. Examples of EGFR inhibitors include but are not limited to cetuximab, which is a chimeric monoclonal antibody given by intravenous injection for treatment of cancers including but not limited to metastatic colorectal cancer and head and neck cancer. Panitumimab is another example of EGFR inhibitor. It is a humanized monoclonal antibody against EGFR. Panitumimab has been shown to be beneficial and better than supportive care when used alone in patients with advanced colon cancer and is approved by the FDA for this use.

Activation of the type 1 insulin-like growth factor receptor (IGF1R) promotes proliferation and inhibits apoptosis in a variety of cell types. Transgenic mice expressing a constitutively active IGF1R or IGF-1 develop mammary tumors and increased levels of IGF1R have been detected in primary breast cancers (Yanochko et. al. *Breast Cancer Research* 2006). It has also been shown that the insulin-like growth factor 1 receptor (IGF1R) and HER2 display important signaling interactions in breast cancer. Specific inhibitors of one of these receptors may cross-inhibit the activity of the other. Targeting both receptors give the maximal inhibition of their downstream extracellular signal-regulated kinase 1/2 and AKT signaling pathways. Hence, such drug combinations may be clinically useful and may be beneficial even in tumors in which single drugs are inactive, as exemplified by the effect of the HER2/IGF1R inhibitor combination in HER2 nonoverexpressing MCF7 cells (Chakraborty A K, et. al, Cancer Res. 2008 Mar. 1; 68(5):1538-45). One example of an IGF1R inhibitor is CP-751871. CP-751871 is a human monoclonal antibody that selectively binds to IGF1R, preventing IGF1 from binding to the receptor and subsequent receptor autophosphorylation. Inhibition of IGF1R autophosphorylation may result in a reduction in receptor expression on tumor cells that express IGF1R, a reduction in the anti-apoptotic effect of IGF, and inhibition of tumor growth. IGF1R is a receptor tyrosine kinase expressed on most tumor cells and is involved in mitogenesis, angiogenesis, and tumor cell survival.

PI3K/mTOR Pathway

Phosphatidylinositol-3-kinase (PI3K) pathway deregulation is a common event in human cancer, either through inactivation of the tumor suppressor phosphatase and tensin homologue deleted from chromosome 10 or activating mutations of p110-α. These hotspot mutations result in oncogenic activity of the enzyme and contribute to therapeutic resistance to the anti-HER2 antibody trastuzumab. The PI3K pathway is, therefore, an attractive target for cancer therapy. NVP-BEZ235, a dual inhibitor of the PI3K and the downstream mammalian target of rapamycin (mTOR) has been shown to inhibit the activation of the downstream effectors Akt, S6 ribosomal protein, and 4EBP1 in breast cancer cells. NVP-BEZ235 inhibits the PI3K/mTOR axis and results in antiproliferative and antitumoral activity in cancer cells with both wild-type and mutated p110-α (Violeta Serra, et. al. *Cancer Research* 68, 8022-8030, Oct. 1, 2008).

Hsp90 Inhibitors

These drugs target heat shock protein 90 (hsp90). Hsp90 is one of a class of chaperone proteins, whose normal job is to help other proteins acquire and maintain the shape required for those proteins to do their jobs. Chaperone proteins work by being in physical contact with other proteins. Hsp90 can also enable cancer cells to survive and even thrive despite genetic defects which would normally cause such cells to die. Thus, blocking the function of HSP90 and related chaperone proteins may cause cancer cells to die, especially if blocking chaperone function is combined with other strategies to block cancer cell survival.

Tubulin Inhibitors

Tubulins are the proteins that form microtubules, which are key components of the cellular cytoskeleton (structural network). Microtubules are necessary for cell division (mitosis), cell structure, transport, signaling and motility. Given their primary role in mitosis, microtubules have been an important target for anticancer drugs—often referred to as antimitotic drugs, tubulin inhibitors and microtubule targeting agents. These compounds bind to tubulin in microtubules and prevent cancer cell proliferation by interfering with the microtubule formation required for cell division. This interference blocks the cell cycle sequence, leading to apoptosis.

Apoptosis Inhibitors

The inhibitors of apoptosis (IAP) are a family of functionally- and structurally-related proteins, originally characterized in Baculovirus, which serve as endogenous inhibitors of apoptosis. The human IAP family consists of at least 6 members, and IAP homologs have been identified in numerous organisms. 10058-F4 is a c-Myc inhibitor that induces cell-cycle arrest and apoptosis. It is a cell-permeable thiazolidinone that specifically inhibits the c-Myc-Max interaction and prevents transactivation of c-Myc target gene expression. 10058-F4 inhibits tumor cell growth in a c-Myc-dependent manner both in vitro and in vivo. B1-6C9 is a tBid inhibitor and antiapoptotic. GNF-2 belongs to a new class of Bcr-abl inhibitors. GNF-2 appears to bind to the myristoyl binding pocket, an allosteric site distant from the active site, stabilizing the inactive form of the kinase. It inhibits Bcr-abl phosphorylation with an $IC_{50}$ of 267 nM, but does not inhibit a panel of 63 other kinases, including native c-Abl, and shows complete lack of toxicity towards cells not expressing Bcr-Abl. GNF-2 shows great potential for a new class of inhibitor to study Bcr-abl activity and to treat resistant Chronic myelogenous leukemia (CML), which is caused the Bcr-Abl oncoprotein. Pifithrin-α is a reversible inhibitor of p53-mediated apoptosis and p53-dependent gene transcription such as cyclin G, p21/waf1, and mdm2 expression. Pifithrin-α enhances cell survival after genotoxic stress such as UV irradiation and treatment with cytotoxic compounds including doxorubicin, etopoxide, paclitaxel, and cytosine-β-D-arabinofuranoside. Pifithrin-α protects mice from lethal whole body γ-irradiation without an increase in cancer incidence.

PARP Inhibitors:

In some embodiments, the present invention provides a method of treating breast cancer that is negative for at least one of ER, PR or —HER2, by administering to a subject in need thereof at least one PARP inhibitor. In other embodiments, the present invention provides a method of treating breast cancer by administering to a subject in need thereof at least one PARP inhibitor in combination with at least one anti-tumor agent described herein.

Not intending to be limited to any particular mechanism of action, the compounds described herein are believed to have anti-cancer properties due to the modulation of activity of a poly (ADP-ribose) polymerase (PARP). This mechanism of action is related to the ability of PARP inhibitors to bind PARP and decrease its activity. PARP catalyzes the conversion of β-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. *Experimental Hematology*, Volume 31, Number 6, June 2003, pp. 446-454(9); Herceg Z.; Wang Z.-Q. *Mutation Research/Fundamental and Molecular Mechanisms of Mutagenesis*, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921).

BRCA1 and BRCA2 act as an integral component of the homologous recombination machinery (HR) (Narod S A, Foulkes W D (2004) Nat Rev Cancer 4:665-676; Gudmundsdottir K, Ashworth A (2006) Oncogene 25:5864-5874).

Cells defective in BRCA1 or BRCA2 have a defect in the repair of double-strand breaks (DSB) by the mechanism of homologous recombination (HR) by gene conversion (Farmer H, et al. (2005) Nature 434:917-921; Narod S A, Foulkes W D (2004) Nat Rev Cancer 4:665-676; Gudmundsdottir K, Ashworth A (2006) Oncogene 25:5864-5874; Helleday T, et al. (2008) Nat Rev Cancer 8:193-204). Deficiency in either of the breast cancer susceptibility proteins BRCA1 or BRCA2 induces profound cellular sensitivity to the inhibition of poly(ADP-ribose) polymerase (PARP) activity, resulting in cell cycle arrest and apoptosis. It has been reported that the critical role of BRCA1 and BRCA2 in the repair of double-strand breaks by homologous recombination (HR) is the underlying reason for this sensitivity, and the deficiency of RAD51, RAD54, DSS1, RPA1, NBS1, ATR, ATM, CHK1, CHK2, FANCD2, FANCA, or FANCC induces such sensitivity (McCabe N. et. al. Deficiency in the repair of DNA damage by homologous recombination and sensitivity to poly (ADP-ribose) polymerase inhibition, *Cancer research* 2006, vol. 66, 8109-8115). It has been proposed that PARP1 inhibition can be a specific therapy for cancers with defects in BRCA1/2 or other HR pathway components (Helleday T, et al. (2008) Nat Rev Cancer 8:193-204). Triple-negative tumors account for 15% of all breast cancers and frequently harbor defects in DNA double-strand break repair through homologous recombination (HR), such as BRCA1 dysfunction (Rottenberg S, et. al. Proc Natl Acad Sci USA. 2008 Nov. 4; 105(44):17079-84).

Inhibiting the activity of a PARP molecule includes reducing the activity of these molecules. The term "inhibits" and its grammatical conjugations, such as "inhibitory," is not intended to require complete reduction in PARP activity. In some embodiments, such reduction is at least about 50%, at least about 75%, at least about 90%, or at least about 95% of the activity of the molecule in the absence of the inhibitory effect, e.g., in the absence of an inhibitor, such as a nitrobenzamide compound of the invention. In some embodiments, inhibition refers to an observable or measurable reduction in activity. In treatment some scenarios, the inhibition is sufficient to produce a therapeutic and/or prophylactic benefit in the condition being treated. The phrase "does not inhibit" and its grammatical conjugations does not require a complete lack of effect on the activity. For example, it refers to situations where there is less than about 20%, less than about 10%, and preferably less than about 5% of reduction in PARP activity in the presence of an inhibitor such as a nitrobenzamide compound of the invention.

Poly (ADP-ribose) polymerase (PARP) is an essential enzyme in DNA repair, thus playing a potential role in chemotherapy resistance. Targeting PARP potentially is thought to interrupt DNA repair, thereby enhancing taxane mediated-, antimetabolite mediated-, topoisomerase inhibitor-mediated, and growth factor receptor inhibitor, e.g. IGF1R inhibitor-mediated, and/or platinum complex mediated-DNA replication and/or repair in cancer cells. PARP inhibitors may also be highly active against breast cancers with impaired function of BRCA1 and BRCA2 or those patients with other DNA repair pathway defects. ER, PR, HER2-negative primary breast cancers demonstrate upregulation of PARP.

This breast cancer subtype has a 9-fold elevated risk of having a BRCA-1 mutation and may have additional defects in the Fanconi anemia DNA repair pathways.

4-Iodo-3-nitrobenzamide (BA) is a small molecule that acts on tumor cells without exerting toxic effects in normal cells. BA is believed to achieve its anti-neoplastic effect by inhibition of PARP. BA is very lipophilic and distributes rapidly and widely into tissues, including the brain and cerebrospinal fluid (CSF). It is active against a broad range of cancer cells in vitro, including against drug resistant cell lines. The person skilled in the art will recognize that BA may be administered in any pharmaceutically acceptable form. e.g. as a pharmaceutically acceptable salt, solvate, or complex. Additionally, as BA is capable of tautomerizing in solution, the tautomeric form of BA is intended to be embraced by the term BA (or the equivalent 4-iodo-3-nitrobenzamide), along with the salts, solvates or complexes. In some embodiments, BA may be administered in combination with a cyclodextrin, such as hydroxypropylbetacyclodextrin. However, one skilled in the art will recognize that other active and inactive agents may be combined with BA; and recitation of BA will, unless otherwise stated, include all pharmaceutically acceptable forms thereof.

Basal-like breast cancers have a high propensity to metastasize to the brain; and BA is known to cross the blood-brain barrier. While not wishing to be bound by any particular theory, it is believed that BA achieves its anti-neoplastic effect by inhibiting the function of PARP. In some embodiments, BA can be used in the treatment of triple negative metastatic breast tumors. In some embodiments, BA can be used in the treatment of breast tumors in which at least one of ER, PR, and Her2 is negative. In some embodiments, BA can be used in the treatment of breast tumors in which at least two of ER, PR, and Her2 is negative, e.g. ER-negative, PR-negative, and Her-2 positive; or ER-positive, PR-negative, and Her-2 negative; or ER-negative, PR-positive, and Her-2 negative.

In some embodiments, BA can be used in the treatment of breast tumors in combination with an anti-tumor agent. In some embodiments, the anti-tumor agent is an antitumor alkylating agent, antitumor antimetabolite, antitumor antibiotics, plant-derived antitumor agent, antitumor platinum complex, antitumor camptothecin derivative, antitumor tyrosine kinase inhibitor, monoclonal antibody, interferon, biological response modifier, hormonal anti-tumor agent, anti-tumor viral agent, angiogenesis inhibitor, differentiating agent, or other agent that exhibits anti-tumor activities, or a pharmaceutically acceptable salt thereof. In other embodiments, BA can be used in the treatment of breast tumors in combination with an antimetabolite such as gemcitabine and a platinum complex such as carboplatin. In still other embodiments, BA can be used in the treatment of metastatic breast tumors in combination with a taxane such as paclitaxel and a platinum complex such as carboplatin. In other embodiments, BA can be used in the treatment of breast tumors in combination with an antimetabolite such as gemcitabine and a platinum complex such as carboplatin. In still other embodiments, BA can be used in the treatment of metastatic breast tumors in combination with a taxane such as paclitaxel and a platinum complex such as carboplatin. In other embodiments, BA can be used in the treatment of breast tumors in combination with an anti-angiogenic agent. In still other embodiments, BA can be used in the treatment of breast tumors in combination with a topoisomerase inhibitor such as irinotecan or topotecan. In other embodiments, BA can be used in the treatment of breast tumors in combination with hormone therapy. In still other embodiments, BA can be used in the treatment of breast tumors in combination with a growth factor receptor inhibitor including but not limited to EGFR or IGF1R inhibitor. In some embodiments, the breast cancer is a metastatic triple negative breast cancer. In some embodiments, the breast cancer is negative for at least one of ER, PR, or Her-2. In some embodiments, the breast cancer is negative for at least two of ER, PR, or Her-2. In other embodiments, the breast cancer is negative for at least one of ER, PR, or Her-2, and positive for at least one of ER, PR, or Her-2. In some embodiments, the breast cancer is negative for at least two of ER, PR, or Her2, e.g. ER-negative, PR-negative, and Her-2 positive; or ER-positive, PR-negative, and Her-2 negative; or ER-negative, PR-positive, and Her-2 negative.

The dosage of PARP inhibitor may vary depending upon the patient age, height, weight, overall health, etc. In some embodiments, the dosage of BA is in the range of about 1 mg/kg to about 100 mg/kg; about 2 mg/kg to about 50 mg/kg, about 2 mg/kg, about 4 mg/kg, about 6 mg/kg, about 8 mg/kg, about 10 mg/kg, about 12 mg/kg, about 15 mg/kg, about 20 mg/kg, about 25 mg/kg, about 30 mg/kg, about 35 mg/kg, about 40 mg/kg, about 50 mg/kg, about 60 mg/kg, about 75 mg/kg, about 90 mg/kg, about 1 to about 25 mg/kg, about 2 to about 70 mg/kg, about 4 to about 100 mg, about 4 to about 25 mg/kg, about 4 to about 20 mg/kg, about 50 to about 100 mg/kg or about 25 to about 75 mg/kg. BA may be administered intravenously, e.g. by IV infusion over about 10 to about 300 minutes, about 30 to about 180 minutes, about 45 to about 120 minutes or about 60 minutes (i.e. about 1 hour). In some embodiments, BA may alternatively be administered orally. In this context, the term "about" has its normal meaning of approximately. In some embodiments, about means±10% or ±5%.

The synthesis of BA (4-iodo-3-nitrobenzamide) is described in U.S. Pat. No. 5,464,871, which is incorporated herein by reference in its entirety. BA may be prepared in concentrations of 10 mg/mL and may be packaged in a convenient form, e.g. in 10 mL vials.

BA Metabolites:

As used herein "BA" means 4-iodo-3-nitrobenzamide: "BNO" means 4-iodo-3-nitrosobenzamide; "BNHOH" means 4-iodo-3-hydroxyaminobenzamide.

Precursor compounds useful in the present invention are of Formula (Ia)

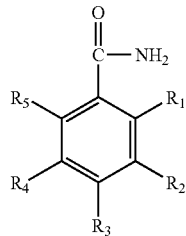

wherein $R_1$, $R_2$, $R_3$, $R_4$, and $R_5$ are, independently selected from the group consisting of hydrogen, hydroxy, amino, nitro, iodo, ($C_1$-$C_6$)-alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen, at least one of the five substituents are always nitro, and at least one substituent positioned adjacent to a nitro is always iodo, and pharmaceutically acceptable salts, solvates, isomers, tautomers, metabolites, analogs, or pro-drugs thereof. $R_1$, $R_2$, $R_3$, $R_4$, and $R_5$ can also be a halide such as chloro, fluoro, or bromo substituents.

A preferred precursor compound of formula Ia is:

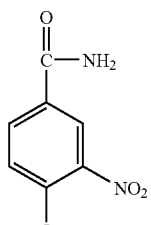

4-iodo-3-nitrobenzamide

Some metabolites useful in the present invention are of the Formula (IIa):

IV.

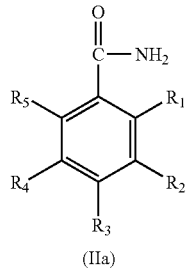

wherein either: (1) at least one of $R_1$, $R_2$, $R_3$, $R_4$, and $R_5$ substituent is always a sulfur-containing substituent, and the remaining substituents $R_1$, $R_2$, $R_3$, $R_4$, and $R_5$ are independently selected from the group consisting of hydrogen, hydroxy, amino, nitro, iodo, bromo, fluoro, chloro, ($C_1$-$C_6$) alkyl, ($C_1$-$C_6$) alkoxy, ($C_3$-$C_7$) cycloalkyl, and phenyl, wherein at least two of the five $R_1$, $R_2$, $R_3$, $R_4$, and $R_5$ substituents are always hydrogen; or (2) at least one of $R_1$, $R_2$, $R_3$, $R_4$, and $R_5$ substituents is not a sulfur-containing substituent and at least one of the five substituents $R_1$, $R_2$, $R_3$, $R_4$, and $R_5$ is always iodo, and wherein said iodo is always adjacent to a $R_1$, $R_2$, $R_3$, $R_4$, or $R_5$ group that is either a nitro, a nitroso, a hydroxyamino, hydroxy or an amino group; and pharmaceutically acceptable salts, solvates, isomers, tautomers, metabolites, analogs, or pro-drugs thereof. In some embodiments, the compounds of (2) are such that the iodo group is always adjacent to a $R_1$, $R_2$, $R_3$, $R_4$ or $R_5$ group that is a nitroso, hydroxyamino, hydroxy or amino group. In some embodiments, the compounds of (2) are such that the iodo group is always adjacent to a $R_1$, $R_2$, $R_3$, $R_4$ or $R_5$ group that is a nitroso, hydroxyamino, or amino group.

The following compositions are preferred metabolite compounds, each represented by a chemical formula:

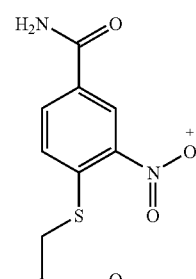

MS472

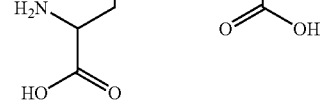

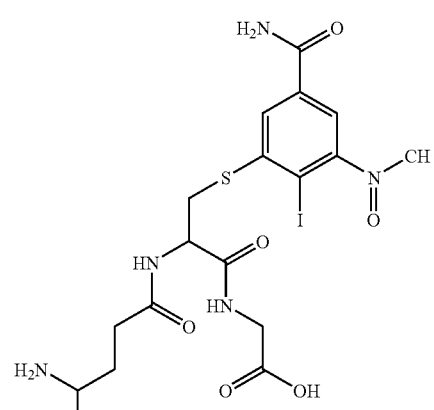

MS601

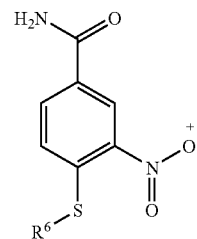

MS213

$R_6$ is selected from a group consisting of hydrogen, alkyl($C_1$-$C_8$), alkoxy ($C_1$-$C_8$), isoquinolinones, indoles, thiazole, oxazole, oxadiazole, thiphene, or phenyl.

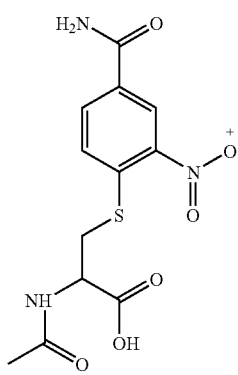 MS328
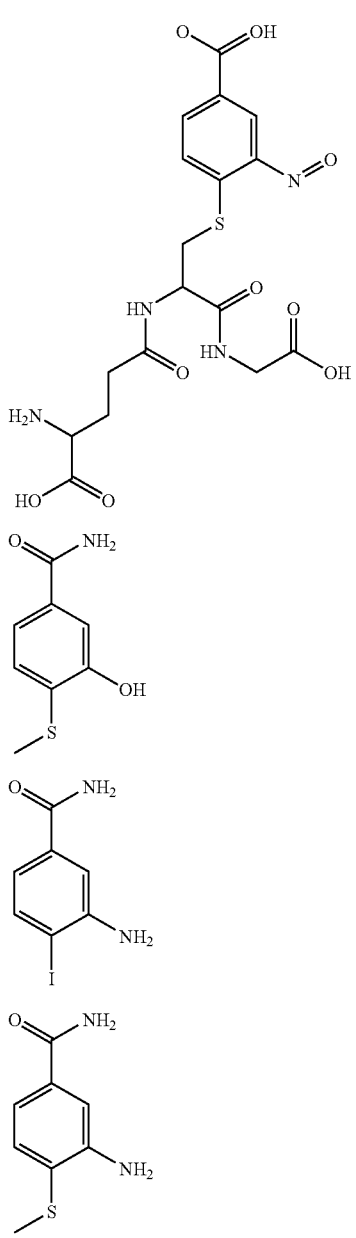
MS456
MS183
MS261
MS182
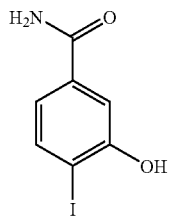 MS263
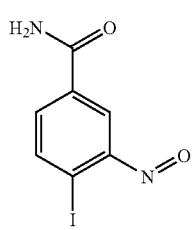 MS276
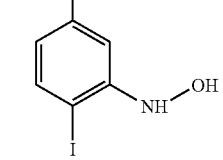 MS278
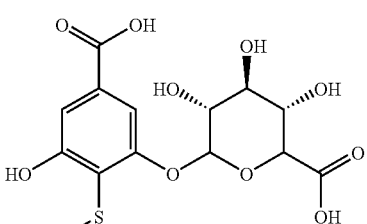 MS635a
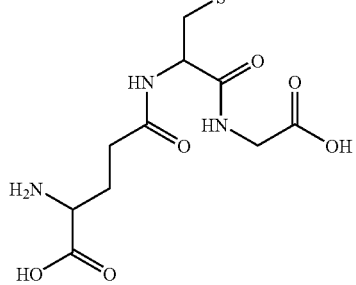

-continued
MS635b
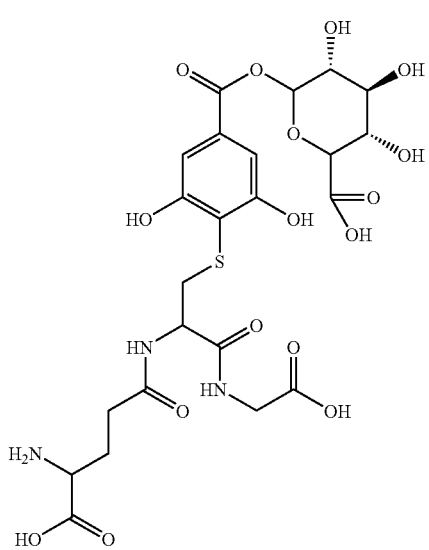
MS471
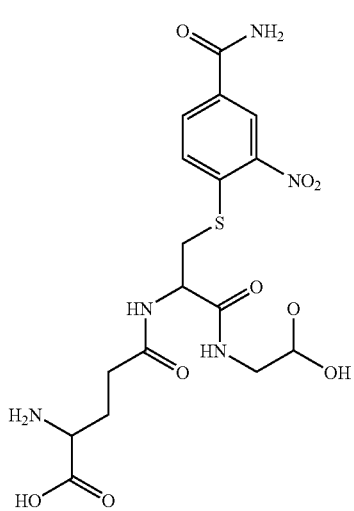
-continued
MS414
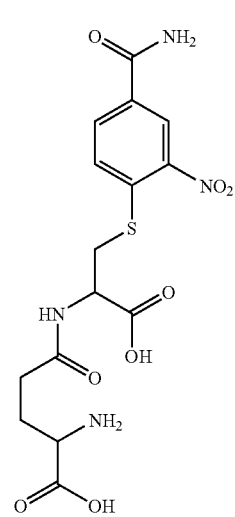
MS692
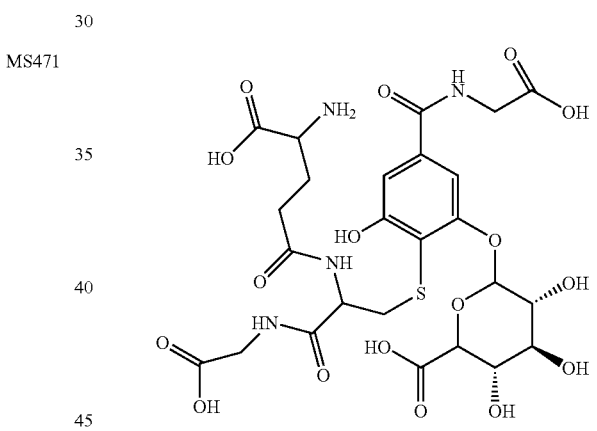
While not being limited to any one particular mechanism, the following provides an example for MS292 metabolism via a nitroreductase or glutathione conjugation mechanism:
Nitroreductase Mechanism
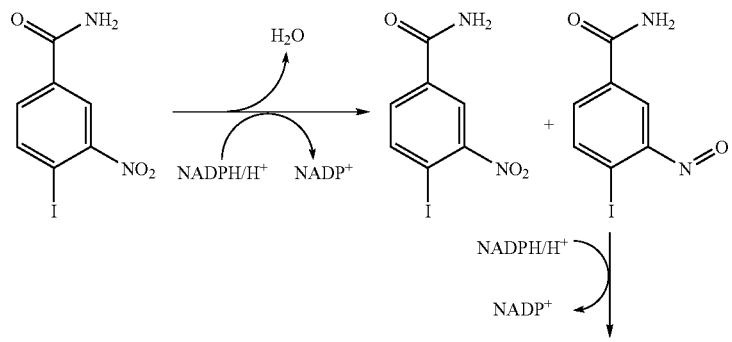

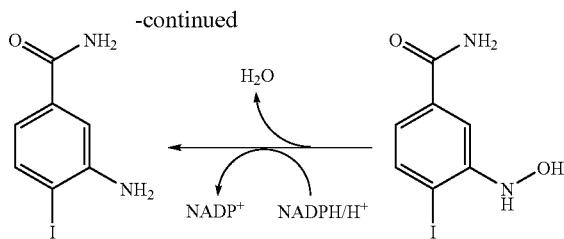
-continued

BA glutathione conjugation and metabolism:

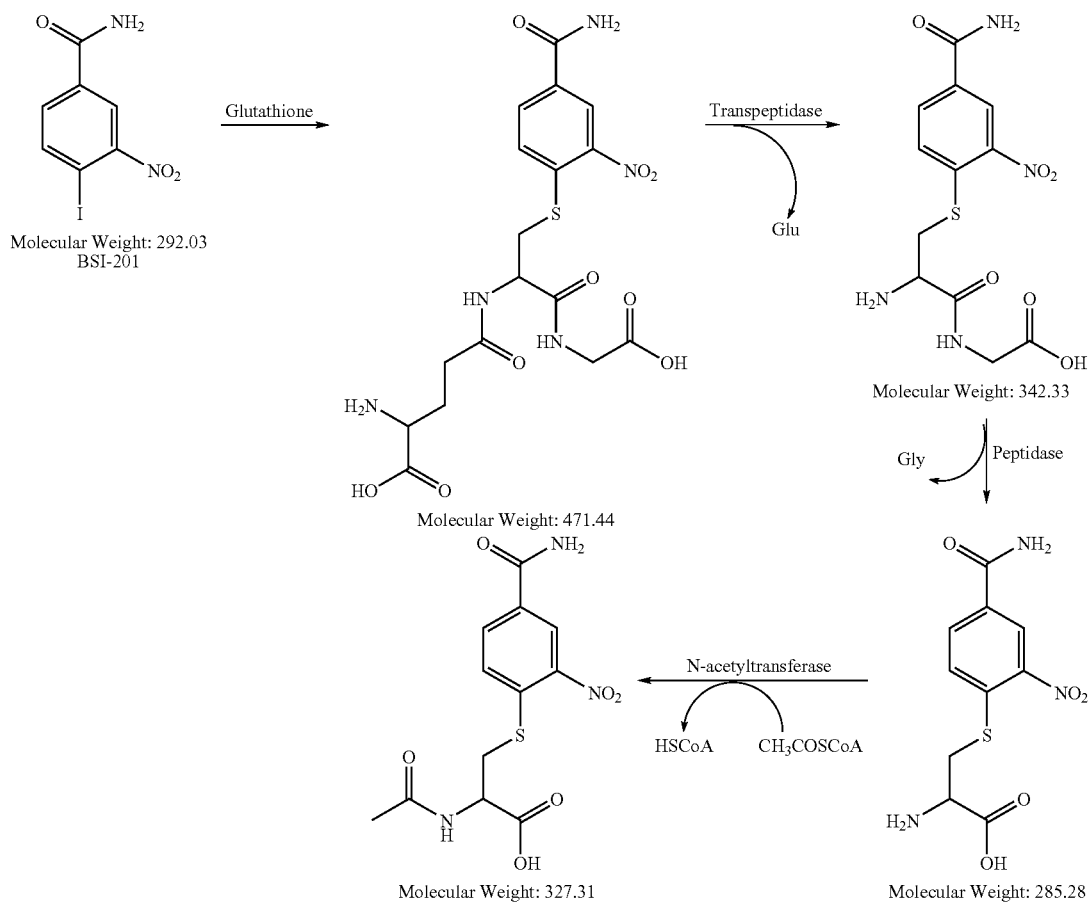

The present invention provides for the use of the aforesaid nitrobenzamide metabolite compounds for the treatment of breast cancers, including breast cancers that are negative for one or more of ER, PR and/or HER2

It has been reported that nitrobenzamide metabolite compounds have selective cytotoxicity upon malignant cancer cells but not upon non-malignant cancer cells. See Rice et at., Proc. Natl. Acad. Sci. USA 89:7703-7707 (1992), incorporated herein in it entirety. In one embodiment, the nitrobenzamide metabolite compounds utilized in the methods of the present invention may exhibit more selective toxicity towards tumor cells than non-tumor cells.

In some embodiments, the invention provides a method of treating breast cancer that is negative for at least one of ER, PR, or Her2, by administering to a subject in need thereof at least one PARP inhibitor. In other embodiments, the invention provides a method of treating breast cancer by administering to a subject in need thereof at least one PARP inhibitor and at least one anti-tumor agent. In some embodiments, the metabolites according to the invention are administered to a patient in need of such treatment in conjunction with chemotherapy with at least one antimetabolite (e.g. one of the citabines, such as gemcitabine) and at least one platinum complex (e.g. carboplatin, cisplatin, etc.) In other embodiments, the metabolites according to the invention are thus administered to a patient in need of such treatment in conjunction with chemotherapy with at least one taxane (e.g. paclitaxel or docetaxel) in addition to at least one platinum complex (e.g. carboplatin, cisplatin, etc.) The dosage range for such metabolites may be in the range of about 0.0004 to about 0.5 mmol/kg (millimoles of metabolite per kilogram of patient body weight), which dosage corresponds, on a molar basis, to a range of about 0.1 to about 100 mg/kg of BA. Other effective ranges of dosages for metabolites are 0.0024-0.5 mmol/kg and 0.0048-0.25 mmol/kg. Such doses may be administered on a daily, every-other-daily, twice-weekly, weekly, bi-weekly, monthly or other suitable schedule. Essentially the same modes of administration may be employed for the metabolites as for BA—e.g. oral, i.v., i.p., etc.

Taxanes:

Taxanes are drugs that are derived from the twigs, needles and bark of Pacific yew tress, *Taxus brevifolia*. In particular paclitaxel may be derived from 10-deacetylbaccatin through known synthetic methods. Taxanes such as paclitaxel and its derivative docetaxel have demonstrated antitumor activity in a variety of tumor types. The taxanes interfere with normal function of microtubule growth by hyperstabilizing their structure, thereby destroying the cell's ability to use its cytoskeleton in a normal manner. Specifically, the taxanes bind to the β subunit of tubulin, which is the building block of microtubules. The resulting taxane/tubulin complex cannot disassemble, which results in aberrant cell function and eventual cell death. Paclitaxel induces programmed cell death (apoptosis) in cancer cells by binding to an apoptosis-inhibiting protein called Bcl-2 (B-cell leukemia 2), thereby preventing Bcl-2 from inhibiting apoptosis. Thus paclitaxel has proven to be an effective treatment for various cancers, as it down-regulates cell division by interrupting normal cytoskeletal rearrangement during cell division and it induces apoptosis via the anti-Bcl-2 mechanism.

The dosage of paclitaxel may vary depending upon the height, weight, physical condition, tumor size and progression state, etc. In some embodiments, the dosage of paclitaxel will be in the range of about 100 to about 1500 mg/m$^2$, about 200 to about 1250 mg/m$^2$, about 500 to about 1000 mg/m$^2$, about 700 to 800 mg/m$^2$ or about 750 mg/m$^2$ of paclitaxel administered over a period of up to about 10 hours, up to about 8 hours or up to about 6 hours. The term "about" in this context indicates the normal usage of approximately; and in some embodiments indicates a tolerance of ±10% or ±5%.

Examples of taxanes include but are not limited to docetaxel, palitaxel, and Abraxane.

Combination Therapy

In certain embodiments of the present invention, the methods of the invention further comprise treating breast cancer by administering to a subject a PARP inhibitor with or without at least one anti-tumor agent in combination with another anti-cancer therapy including but not limited to surgery, radiation therapy (e.g. X ray), gene therapy, immunotherapy, DNA therapy, adjuvant therapy, neoadjuvant therapy, viral therapy, RNA therapy, or nanotherapy.

Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, by a significant period of time. The conjugate and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

Radiation Therapy

Radiation therapy (or radiotherapy) is the medical use of ionizing radiation as part of cancer treatment to control malignant cells. Radiotherapy may be used for curative or adjuvant cancer treatment. It is used as palliative treatment (where cure is not possible and the aim is for local disease control or symptomatic relief) or as therapeutic treatment (where the therapy has survival benefit and it can be curative). Radiotherapy is used for the treatment of malignant tumors and may be used as the primary therapy. It is also common to combine radiotherapy with surgery, chemotherapy, hormone therapy or some mixture of the three. Most common cancer types can be treated with radiotherapy in some way. The precise treatment intent (curative, adjuvant, neoadjuvant, therapeutic, or palliative) will depend on the tumour type, location, and stage, as well as the general health of the patient.

Radiation therapy is commonly applied to the cancerous tumor. The radiation fields may also include the draining of lymph nodes if they are clinically or radiologically involved with tumor, or if there is thought to be a risk of subclinical malignant spread. It is necessary to include a margin of normal tissue around the tumor to allow for uncertainties in daily set-up and internal tumor motion.

Radiation therapy works by damaging the DNA of cells. The damage is caused by a photon, electron, proton, neutron, or ion beam directly or indirectly ionizing the atoms which make up the DNA chain. Indirect ionization happens as a result of the ionization of water, forming free radicals, notably hydroxyl radicals, which then damage the DNA. In the most common forms of radiation therapy, most of the radiation effect is through free radicals. Because cells have mechanisms for repairing DNA damage, breaking the DNA on both strands proves to be the most significant technique in modifying cell characteristics. Because cancer cells generally are undifferentiated and stem cell-like, they reproduce more, and have a diminished ability to repair sub-lethal damage compared to most healthy differentiated cells. The DNA damage is inherited through cell division, accumulating damage to the cancer cells, causing them to die or reproduce more slowly. Proton radiotherapy works by sending protons with varying kinetic energy to precisely stop at the tumor.

Gamma rays are also used to treat some types of cancer including breast cancer. In the procedure called gamma-knife surgery, multiple concentrated beams of gamma rays are directed on the growth in order to kill the cancerous cells. The beams are aimed from different angles to focus the radiation on the growth while minimizing damage to the surrounding tissues.

In some embodiments, gamma irradiation is used to treat triple negative breast cancer and is exemplified in Example 9.

Gene Therapy Agents

Gene therapy agents insert copies of genes into a specific set of a patient's cells, and can target both cancer and non-cancer cells. The goal of gene therapy can be to replace altered genes with functional genes, to stimulate a patient's immune response to cancer, to make cancer cells more sensitive to chemotherapy, to place "suicide" genes into cancer cells, or to inhibit angiogenesis. Genes may be delivered to target cells using viruses, liposomes, or other carriers or vectors. This may be done by injecting the gene-carrier composition into the patient directly, or ex vivo, with infected cells being introduced back into a patient. Such compositions are suitable for use in the present invention.

Adjuvant Therapy

Adjuvant therapy is a treatment given after the primary treatment to increase the chances of a cure. Adjuvant therapy may include chemotherapy, radiation therapy, hormone therapy, or biological therapy.

Because the principal purpose of adjuvant therapy is to kill any cancer cells that may have spread, treatment is usually systemic (uses substances that travel through the bloodstream, reaching and affecting cancer cells all over the body). Adjuvant therapy for breast cancer involves chemotherapy or hormone therapy, either alone or in combination:

Adjuvant chemotherapy is the use of drugs to kill cancer cells. Research has shown that using chemotherapy as adjuvant therapy for early stage breast cancer helps to prevent the original cancer from returning. Adjuvant chemotherapy is usually a combination of anticancer drugs, which has been shown to be more effective than a single anticancer drug.

Adjuvant hormone therapy deprives cancer cells of the female hormone estrogen, which some breast cancer cells need to grow. Most often, adjuvant hormone therapy is treatment with the drug tamoxifen. Research has shown that when tamoxifen is used as adjuvant therapy for early stage breast cancer, it helps to prevent the original cancer from returning and also helps to prevent the development of new cancers in the other breast.

The ovaries are the main source of estrogen prior to menopause. For premenopausal women with breast cancer, adjuvant hormone therapy may involve tamoxifen to deprive the cancer cells of estrogen. Drugs to suppress the production of estrogen by the ovaries are under investigation. Alternatively, surgery may be performed to remove the ovaries.

Radiation therapy is sometimes used as a local adjuvant treatment. Radiation therapy is considered adjuvant treatment when it is given before or after a mastectomy. Such treatment is intended to destroy breast cancer cells that have spread to nearby parts of the body, such as the chest wall or lymph nodes. Radiation therapy is part of primary therapy, not adjuvant therapy, when it follows breast-sparing surgery.

Neoadjuvant Therapy

Neoadjuvant therapy refers to a treatment given before the primary treatment. Examples of neoadjuvant therapy include chemotherapy, radiation therapy, and hormone therapy. In treating breast cancer, neoadjuvant therapy allows patients with large breast cancer to undergo breast-conserving surgery.

Oncolytic Viral Therapy

Viral therapy for cancer utilizes a type of viruses called oncolytic viruses. An oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site.

There are two main approaches for generating tumor selectivity: transductional and non-transductional targeting. Transductional targeting involves modifying the specificity of viral coat protein, thus increasing entry into target cells while reducing entry to non-target cells. Non-transductional targeting involves altering the genome of the virus so it can only replicate in cancer cells. This can be done by either transcription targeting, where genes essential for viral replication are placed under the control of a tumor-specific promoter, or by attenuation, which involves introducing deletions into the viral genome that eliminate functions that are dispensable in cancer cells, but not in normal cells. There are also other, slightly more obscure methods.

Chen et al (2001) used CV706, a prostate-specific adenovirus, in conjunction with radiotherapy on prostate cancer in mice. The combined treatment results in a synergistic increase in cell death, as well as a significant increase in viral burst size (the number of virus particles released from each cell lysis).

ONYX-015 has undergone trials in conjunction with chemotherapy. The combined treatment gives a greater response than either treatment alone, but the results have not been entirely conclusive. ONYX-015 has shown promise in conjunction with radiotherapy.

Viral agents administered intravenously can be particularly effective against metastatic cancers, which are especially difficult to treat conventionally. However, bloodborne viruses can be deactivated by antibodies and cleared from the blood stream quickly e.g. by Kupffer cells (extremely active phagocytic cells in the liver, which are responsible for adenovirus clearance). Avoidance of the immune system until the tumour is destroyed could be the biggest obstacle to the success of oncolytic virus therapy. To date, no technique used to evade the immune system is entirely satisfactory. It is in conjunction with conventional cancer therapies that oncolytic viruses show the most promise, since combined therapies operate synergistically with no apparent negative effects.

The specificity and flexibility of oncolytic viruses means they have the potential to treat a wide range of cancers including breast cancer with minimal side effects. Oncolytic viruses have the potential to solve the problem of selectively killing cancer cells.

Nanotherapy

Nanometer-sized particles have novel optical, electronic, and structural properties that are not available from either individual molecules or bulk solids. When linked with tumor-targeting moieties, such as tumor-specific ligands or monoclonal antibodies, these nanoparticles can be used to target cancer-specific receptors, tumor antigens (biomarkers), and tumor vasculatures with high affinity and precision. The formulation and manufacturing process for cancer nanotherapy is disclosed in U.S. Pat. No. 7,179,484, and article M. N. Khalid, P. Simard, D. Hoarau, A. Dragomir, J. Leroux, Long Circulating Poly(Ethylene Glycol)Decorated Lipid Nanocapsules Deliver Docetaxel to Solid Tumors, *Pharmaceutical Research*, 23(4), 2006, all of which are herein incorporated by reference in their entireties.

RNA Therapy

RNA including but not limited to siRNA, shRNA, or microRNA may be used to modulate gene expression and treat cancers. Double stranded oligonucleotides are formed by the assembly of two distinct oligonucleotide sequences where the oligonucleotide sequence of one strand is complementary to the oligonucleotide sequence of the second strand; such double stranded oligonucleotides are generally assembled from two separate oligonucleotides (e.g., siRNA), or from a single molecule that folds on itself to form a double stranded structure (e.g., shRNA or short hairpin RNA). These double stranded oligonucleotides known in the art all have a common feature in that each strand of the duplex has a distinct nucleotide sequence, wherein only one nucleotide sequence region (guide sequence or the antisense sequence) has complementarity to a target nucleic acid sequence and the other strand (sense sequence) comprises a nucleotide sequence that is homologous to the target nucleic acid sequence.

MicroRNAs (miRNA) are single-stranded RNA molecules of about 21-23 nucleotides in length, which regulate gene expression. miRNAs are encoded by genes that are transcribed from DNA but not translated into protein (non-coding RNA); instead they are processed from primary transcripts known as pri-miRNA to short stem-loop structures called pre-miRNA and finally to functional miRNA. Mature miRNA molecules are partially complementary to one or more messenger RNA (mRNA) molecules, and their main function is to downregulate gene expression.

Certain RNA inhibiting agents may be utilized to inhibit the expression or translation of messenger RNA ("mRNA") that is associated with a cancer phenotype. Examples of such agents suitable for use herein include, but are not limited to, short interfering RNA ("siRNA"), ribozymes, and antisense oligonucleotides. Specific examples of RNA inhibiting agents suitable for use herein include, but are not limited to, Cand5, Sirna-027, fomivirsen, and angiozyme.

Small Molecule Enzymatic Inhibitors

Certain small molecule therapeutic agents are able to target the tyrosine kinase enzymatic activity or downstream signal transduction signals of certain cell receptors such as epidermal growth factor receptor ("EGFR") or vascular endothelial growth factor receptor ("VEGFR"). Such targeting by small molecule therapeutics can result in anti-cancer effects. Examples of such agents suitable for use herein include, but are not limited to, imatinib, gefitinib, erlotinib, lapatinib, canertinib, ZD6474, sorafenib (BAY 43-9006), ERB-569, and their analogues and derivatives.

Anti-Metastatic Agents

The process whereby cancer cells spread from the site of the original tumor to other locations around the body is termed cancer metastasis. Certain agents have anti-metastatic properties, designed to inhibit the spread of cancer cells. Examples of such agents suitable for use herein include, but are not limited to, marimastat, bevacizumab, trastuzumab, rituximab, erlotinib, MMI-166, GRN163L, hunter-killer peptides, tissue inhibitors of metalloproteinases (TIMPs), their analogues, derivatives and variants.

Chemopreventative Agents

Certain pharmaceutical agents can be used to prevent initial occurrences of cancer, or to prevent recurrence or metastasis. Administration of such chemopreventative agents in combination with eflornithine-NSAID conjugates of the invention can act to both treat and prevent the recurrence of cancer. Examples of chemopreventative agents suitable for use herein include, but are not limited to, tamoxifen, raloxifene, tibolone, bisphosphonate, ibandronate, estrogen receptor modulators, aromatase inhibitors (letrozole, anastrozole), luteinizing hormone-releasing hormone agonists, goserelin, vitamin A, retinal, retinoic acid, fenretinide, 9-cis-retinoid acid, 13-cis-retinoid acid, all-trans-retinoic acid, isotretinoin, tretinoid, vitamin B6, vitamin B12, vitamin C, vitamin D, vitamin E, cyclooxygenase inhibitors, non-steroidal anti-inflammatory drugs (NSAIDs), aspirin, ibuprofen, celecoxib, polyphenols, polyphenol E, green tea extract, folic acid, glucaric acid, interferon-alpha, anethole dithiolethione, zinc, pyridoxine, finasteride, doxazosin, selenium, indole-3-carbinal, alpha-difluoromethylornithine, carotenoids, beta-carotene, lycopene, antioxidants, coenzyme Q10, flavonoids, quercetin, curcumin, catechins, epigallocatechin gallate, N-acetylcysteine, indole-3-carbinol, inositol hexaphosphate, isoflavones, glucanic acid, rosemary, soy, saw palmetto, and calcium. An additional example of chemopreventative agents suitable for use in the present invention is cancer vaccines. These can be created through immunizing a patient with all or part of a cancer cell type that is targeted by the vaccination process.

Clinical Efficacy:

Staging of Breast Cancer:

Stage 0 is used to describe non-invasive breast cancers, such as DCIS and LCIS. In stage 0, there is no evidence of cancer cells or non-cancerous abnormal cells breaking out of the part of the breast in which they started, or of getting through to or invading neighboring normal tissue.

Stage I describes invasive breast cancer (cancer cells are breaking through to or invading neighboring normal tissue) in which the tumor measures up to 2 centimeters, and no lymph nodes are involved.

Stage II is divided into subcategories known as IIA and IIB. Stage IIA describes invasive breast cancer in which no tumor can be found in the breast, but cancer cells are found in the axillary lymph nodes (the lymph nodes under the arm), or the tumor measures 2 centimeters or less and has spread to the axillary lymph nodes, or the tumor is larger than 2 centimeters but not larger than 5 centimeters and has not spread to the axillary lymph nodes. Stage IIB describes invasive breast cancer in which: the tumor is larger than 2 but no larger than 5 centimeters and has spread to the axillary lymph nodes, or the tumor is larger than 5 centimeters but has not spread to the axillary lymph nodes.

Stage III is divided into subcategories known as IIIA, IIIB, and IIIC. Stage IIIA describes invasive breast cancer in which either no tumor is found in the breast. Cancer is found in axillary lymph nodes that are clumped together or sticking to other structures, or cancer may have spread to lymph nodes near the breastbone, or the tumor is 5 centimeters or smaller and has spread to axillary lymph nodes that are clumped together or sticking to other structures, or the tumor is larger than 5 centimeters and has spread to axillary lymph nodes that are clumped together or sticking to other structures. Stage IIIB describes invasive breast cancer in which the tumor may be any size and has spread to the chest wall and/or skin of the breast and may have spread to axillary lymph nodes that are clumped together or sticking to other structures, or cancer may have spread to lymph nodes near the breastbone. Stage IIIC describes invasive breast cancer in which there may be no sign of cancer in the breast or, if there is a tumor, it may be any size and may have spread to the chest wall and/or the skin of the breast, and the cancer has spread to lymph nodes above or below the collarbone, and the cancer may have spread to axillary lymph nodes or to lymph nodes near the breastbone.

Clinical efficacy may be measured by any method known in the art. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD$\geqq$6 months. The CBR for combination therapy with gemcitabine and carboplatin is 45%. Thus, the CBR for triple combination therapy with an antimetabolite, platinum complex and PARP inhibitor (e.g. gemcitabine, carboplatin and BA; $CBR_{GCB}$) may be compared to that of the double combination therapy with gemcitabine and carboplatin (CBR$_{GC}$). In some embodiments, CBR$_{GCB}$ is at least about 60%. In some embodiments, CBR is at least about 30%, at least about 40%, or at least about 50%. The CBR for combination therapy with paclitaxel and carboplatin is 45%. Thus, the CBR for triple combination therapy with a taxane, platinum complex and PARP inhibitor (e.g. paclitaxel, carboplatin and BA; CBR$_{GCB}$) may be compared to that of the double combination therapy with paclitaxel and carboplatin (CBR$_{GC}$). In some embodiments, CBR$_{GCB}$ is at least about 60%.

In some embodiments, CBR is at least about 30%, at least about 40%, or at least about 50%. In some embodiments, the therapeutic effect includes reduction in size of a breast tumor, reduction in metastasis, complete remission, partial remission, stable disease, or a pathologic complete response.

Neoadjuvant chemotherapy is now widely used in the treatment of locally advanced or potentially operable large breast cancers. Randomised trials have demonstrated neoadjuvant chemotherapy reduces the need for mastectomy (Powles et al, 1995; Fisher et al, 1998), with similar overall survival rates to adjuvant chemotherapy (Fisher et al, 1998). Women achieving no residual histological evidence of tumor after chemotherapy at the time of surgery (i.e. a pathologic complete response (pCR)) have a significantly improved survival (Bonadonna et al, 1998; Fisher et al, 1998; Kuerer et al, 1999), and pCR is often used as an early surrogate marker of treatment efficacy. However, there is no standard method for grading pathological response of breast tumours to neoadjuvant chemotherapy and a number of different classification systems have been proposed (Chevallier et al, 1993; Sataloff et al, 1995; Fisher et al, 1997; Honkoop et al, 1998; Kuerer et al, 1998; Ogston et al, 2003). Most, but not all, of these grading schemes have included both no residual disease of any sort and residual ductal carcinoma in situ (DCIS) without invasive disease in the definition of pCR.

In some embodiments disclosed herein, the methods include pre-determining that a cancer is treatable by PARP modulators. Some such methods comprise identifying a level of PARP in a breast cancer sample of a patient, determining whether the level of PARP expression in the sample is greater than a pre-determined value, and, if the PARP expression is greater than said predetermined value, treating the patient with a combination of a taxane (e.g. paclitaxel), a platinum complex (e.g. carboplatin) and a PARP inhibitor such as BA. In other embodiments, the methods comprise identifying a level of PARP in a breast cancer sample of a patient, determining whether the level of PARP expression in the sample is greater than a pre-determined value, and, if the PARP expression is greater than said predetermined value, treating the patient with a PARP inhibitor such as BA. In other embodiments, the methods include pre-determining that a cancer is treatable by PARP modulators. Some such methods comprise identifying a level of PARP in a breast cancer sample of a patient, determining whether the level of PARP expression in the sample is greater than a pre-determined value, and, if the PARP expression is greater than said predetermined value, treating the patient with a combination of an antimetabolite (e.g. gemcitabine), a platinum complex (e.g. carboplatin) and a PARP inhibitor such as BA.

Breast tumors in women who inherit faults in either the BRCA1 or BRCA2 genes occur because the tumor cells have lost a specific mechanism that repair damaged DNA. BRCA1 and BRCA2 are important for DNA double-strand break repair by homologous recombination, and mutations in these genes predispose to breast and other cancers. PARP is involved in base excision repair, a pathway in the repair of DNA single-strand breaks. BRCA1 or BRCA2 dysfunction sensitizes cells to the inhibition of PARP enzymatic activity, resulting in chromosomal instability, cell cycle arrest and subsequent apoptosis (Jones C, Plummer E R. PARP inhibitors and cancer therapy—early results and potential applications. Br J Radiol. 2008 October; 81 Spec No 1:S2-5; Drew Y, Calvert H. The potential of PARP inhibitors in genetic breast and ovarian cancers. Ann N Y Acad. Sci. 2008 September; 1138:136-45; Farmer H, et. al. Targeting the DNA repair defect in BRCA mutant cells as a therapeutic strategy. Nature. 2005 Apr. 14; 434(7035):917-21).

Patients deficient in BRCA genes can have up-regulated levels of PARP. PARP up-regulation may be an indicator of defective DNA-repair pathways and unrecognized BRCA-like genetic defects. Assessment of PARP gene expression and impaired DNA repair, especially defective homologous recombination DNA repair, can be used as an indicator of tumor sensitivity to PARP inhibitor. Hence, in some embodiments, treatment of breast cancer can be enhanced not only by determining the HR and/or HER2 status of the cancer, but also by identifying early onset of cancer in BRCA and homologous recombination DNA repair deficient patients by measuring the level of PARP. The BRCA and homologous recombination DNA repair deficient patients treatable by PARP inhibitors can be identified if PARP is up-regulated. Further, such homologous recombination DNA repair deficient patients can be treated with PARP inhibitors.

In some embodiments, a sample is collected from a patient having a breast lesion or growth suspected of being cancerous. While such sample may be any available biological tissue, in most cases the sample will be a portion of the suspected breast lesion, whether obtained by minimally invasive biopsy or by therapeutic surgery (e.g. lumpectomy, mastectomy, partial or modified mastectomy or radical mastectomy, hysterectomy, or oophorectomy). Such sample may also include all or part of one or more lymph nodes extracted during the therapeutic surgery. PARP expression may then be analyzed. In some embodiments, if the PARP expression is above a predetermined level (e.g. is up-regulated vis-à-vis normal tissue) the patient may be treated with a PARP inhibitor in combination with an antimetabolite and a platinum agent. In other embodiments, if the PARP expression is above a predetermined level (e.g. is up-regulated vis-à-vis normal tissue) the patient may be treated with a PARP inhibitor, including a PARP inhibitor, such as BA. It is thus to be understood that, while embodiments described herein are directed to treatment of triple negative metastatic breast cancer, in some embodiments the breast cancer need not have these characteristics so long as the threshold PARP up-regulation is satisfied.

In some embodiments, tumors that are homologous recombination deficient are identified by evaluating levels of PARP expression. If up-regulation of PARP is observed, such tumors can be treated with PARP inhibitors. Another embodiment is a method for treating a homologous recombination deficient cancer comprising evaluating level of PARP expression and, if overexpression is observed, the cancer is treated with a PARP inhibitor.

Sample Collection, Preparation and Separation

Biological samples may be collected from a variety of sources from a patient including a body fluid sample, or a tissue sample. Samples collected can be human normal and tumor samples, nipple aspirants. The samples can be collected from individuals repeatedly over a longitudinal period of time (e.g., about once a day, once a week, once a month, biannually or annually). Obtaining numerous samples from an individual over a period of time can be used to verify results from earlier detections and/or to identify an alteration in biological pattern as a result of, for example, disease progression, drug treatment, etc.

Sample preparation and separation can involve any of the procedures, depending on the type of sample collected and/or analysis of PARP. Such procedures include, by way of example only, concentration, dilution, adjustment of pH, removal of high abundance polypeptides (e.g., albumin, gamma globulin, and transferin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g. aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC) etc.

Identifying Level of PARP

The poly (ADP-ribose) polymerase (PARP) is also known as poly (ADP-ribose) synthase and poly ADP-ribosyltransferase. PARP catalyzes the formation of mono- and poly (ADP-ribose) polymers which can attach to cellular proteins (as well as to itself) and thereby modify the activities of those proteins. The enzyme plays a role in regulation of transcription, cell proliferation, and chromatin remodeling (for review see: D. D'amours et al. "Poly (ADP-ribosylation reactions in the regulation of nuclear functions," Biochem. J. 342: 249-268 (1999)).

PARP comprises an N-terminal DNA binding domain, an automodification domain and a C-terminal catalytic domain and various cellular proteins interact with PARP. The N-terminal DNA binding domain contains two zinc finger motifs. Transcription enhancer factor-1 (TEF-1), retinoid X receptor α, DNA polymerase α, X-ray repair cross-complementing factor-1 (XRCC1) and PARP itself interact with PARP in this domain. The automodification domain contains a BRCT motif, one of the protein-protein interaction modules. This motif is originally found in the C-terminus of BRCA1 (breast cancer susceptibility protein 1) and is present in various proteins related to DNA repair, recombination and cell-cycle checkpoint control. POU-homeodomain-containing octamer transcription factor-1 (Oct-1), Yin Yang (YY)1 and ubiquitin-conjugating enzyme 9 (ubc9) could interact with this BRCT motif in PARP.

More than 15 members of the PARP family of genes are present in the mammalian genome. PARP family proteins and poly(ADP-ribose) glycohydrolase (PARG), which degrades poly(ADP-ribose) to ADP-ribose, could be involved in a variety of cell regulatory functions including DNA damage response and transcriptional regulation and may be related to carcinogenesis and the biology of cancer in many respects.

Several PARP family proteins have been identified. Tankyrase has been found as an interacting protein of telomere regulatory factor 1 (TRF-1) and is involved in telomere regulation. Vault PARP (VPARP) is a component in the vault complex, which acts as a nuclear-cytoplasmic transporter.

PARP-2, PARP-3 and 2,3,7,8-tetrachlorodibenzo-p-dioxin inducible PARP (TiPARP) have also been identified. Therefore, poly (ADP-ribose) metabolism could be related to a variety of cell regulatory functions.

A member of this gene family is PARP-1. The PARP-1 gene product is expressed at high levels in the nuclei of cells and is dependent upon DNA damage for activation. Without being bound by any theory, it is believed that PARP-1 binds to DNA single or double stranded breaks through an amino terminal DNA binding domain. The binding activates the carboxy terminal catalytic domain and results in the formation of polymers of ADP-ribose on target molecules. PARP-1 is itself a target of poly ADP-ribosylation by virtue of a centrally located automodification domain. The ribosylation of PARP-1 causes dissociation of the PARP-1 molecules from the DNA. The entire process of binding, ribosylation, and dissociation occurs very rapidly. It has been suggested that this transient binding of PARP-1 to sites of DNA damage results in the recruitment of DNA repair machinery or may act to suppress the recombination long enough for the recruitment of repair machinery.

The source of ADP-ribose for the PARP reaction is nicotinamide adenosine dinucleotide (NAD). NAD is synthesized in cells from cellular ATP stores and thus high levels of activation of PARP activity can rapidly lead to depletion of cellular energy stores. It has been demonstrated that induction of PARP activity can lead to cell death that is correlated with depletion of cellular NAD and ATP pools. PARP activity is induced in many instances of oxidative stress or during inflammation. For example, during reperfusion of ischemic tissues reactive nitric oxide is generated and nitric oxide results in the generation of additional reactive oxygen species including hydrogen peroxide, peroxynitrate and hydroxyl radical. These latter species can directly damage DNA and the resulting damage induces activation of PARP activity. Frequently, it appears that sufficient activation of PARP activity occurs such that the cellular energy stores are depleted and the cell dies. A similar mechanism is believed to operate during inflammation when endothelial cells and pro-inflammatory cells synthesize nitric oxide which results in oxidative DNA damage in surrounding cells and the subsequent activation of PARP activity. The cell death that results from PARP activation is believed to be a major contributing factor in the extent of tissue damage that results from ischemia-reperfusion injury or from inflammation.

In some embodiments, the level of PARP in a sample from a patient is compared to predetermined standard sample. The sample from the patient is typically from a diseased tissue, such as cancer cells or tissues. The standard sample can be from the same patient or from a different subject. The standard sample is typically a normal, non-diseased sample. However, in some embodiments, such as for staging of disease or for evaluating the efficacy of treatment, the standard sample is from a diseased tissue. The standard sample can be a combination of samples from several different subjects. In some embodiments, the level of PARP from a patient is compared to a pre-determined level. This pre-determined level is typically obtained from normal samples. As described herein, a "pre-determined PARP level" may be a level of PARP used to, by way of example only, evaluate a patient that may be selected for treatment, evaluate a response to a PARP inhibitor treatment, evaluate a response to a combination of a PARP inhibitor and a second therapeutic agent treatment, and/or diagnose a patient for cancer, inflammation, pain and/or related conditions. A pre-determined PARP level may be determined in populations of patients with or without cancer.

The pre-determined PARP level can be a single number, equally applicable to every patient, or the pre-determined PARP level can vary according to specific subpopulations of patients. For example, men might have a different pre-determined PARP level than women; non-smokers may have a different pre-determined PARP level than smokers. Age, weight, and height of a patient may affect the pre-determined PARP level of the individual. Furthermore, the pre-determined PARP level can be a level determined for each patient individually. The pre-determined PARP level can be any suitable standard. For example, the pre-determined PARP level can be obtained from the same or a different human for whom a patient selection is being assessed. In one embodiment, the pre-determined PARP level can be obtained from a previous assessment of the same patient. In such a manner, the progress of the selection of the patient can be monitored over time. In addition, the standard can be obtained from an assessment of another human or multiple humans, e.g., selected groups of humans. In such a manner, the extent of the selection of the human for whom selection is being assessed can be compared to suitable other humans, e.g., other humans who are in a similar situation to the human of interest, such as those suffering from similar or the same condition(s).

In some embodiments of the present invention the change of PARP from the pre-determined level is about 0.5 fold, about 1.0 fold, about 1.5 fold, about 2.0 fold, about 2.5 fold, about 3.0 fold, about 3.5 fold, about 4.0 fold, about 4.5 fold, or about 5.0 fold. In some embodiments is fold change is less than about 1, less than about 5, less than about 10, less than about 20, less than about 30, less than about 40, or less than about 50. In other embodiments, the changes in PARP level compared to a predetermined level is more than about 1, more than about 5, more than about 10, more than about 20, more than about 30, more than about 40, or more than about 50. Preferred fold changes from a pre-determined level are about 0.5, about 1.0, about 1.5, about 2.0, about 2.5, and about 3.0.

The analysis of PARP levels in patients is particularly valuable and informative, as it allows the physician to more effectively select the best treatments, as well as to utilize more aggressive treatments and therapy regimens based on the up-regulated or down-regulated level of PARP. More aggressive treatment, or combination treatments and regimens, can serve to counteract poor patient prognosis and overall survival time. Armed with this information, the medical practitioner can choose to provide certain types of treatment such as treatment with PARP inhibitors, and/or more aggressive therapy.

In monitoring a patient's PARP levels, over a period of time, which may be days, weeks, months, and in some cases, years, or various intervals thereof, the patient's body fluid sample, e.g., serum or plasma, can be collected at intervals, as determined by the practitioner, such as a physician or clinician, to determine the levels of PARP, and compared to the levels in normal individuals over the course or treatment or disease. For example, patient samples can be taken and monitored every month, every two months, or combinations of one, two, or three month intervals according to the invention. In addition, the PARP levels of the patient obtained over time can be conveniently compared with each other, as well as with the PARP values, of normal controls, during the monitoring period, thereby providing the patient's own PARP values, as an internal, or personal, control for long-term PARP monitoring.

Techniques for Analysis of PARP

The analysis of the PARP may include analysis of PARP gene expression, including an analysis of DNA, RNA, analysis of the level of PARP and/or analysis of the activity of PARP including a level of mono- and poly-ADP-ribozylation. Without limiting the scope of the present invention, any number of techniques known in the art can be employed for the analysis of PARP and they are all within the scope of the present invention. Some of the examples of such detection technique are given below but these examples are in no way limiting to the various detection techniques that can be used in the present invention.

Gene Expression Profiling: Methods of gene expression profiling include methods based on hybridization analysis of polynucleotides, polyribonucleotides methods based on sequencing of polynucleotides, polyribonucleotides and proteomics-based methods. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and PCR-based methods, such as reverse transcription polymerase chain reaction (RT-PCR) (Weis et al., Trends in Genetics 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS), Comparative Genome Hybridisation (CGH), Chromatin Immunoprecipitation (ChIP), Single nucleotide polymorphism (SNP) and SNP arrays, Fluorescent in situ Hybridization (FISH), Protein binding arrays and DNA microarray (also commonly known as gene or genome chip, DNA chip, or gene array), RNAmicroarrays.

Reverse Transcriptase PCR(RT-PCR): One of the most sensitive and most flexible quantitative PCR-based gene expression profiling methods is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. For example, the starting material can be typically total RNA isolated from human tumors or tumor cell lines, and corresponding normal tissues or cell lines, respectively. Thus RNA can be isolated from a variety of normal and diseased cells and tissues, for example tumors, including breast, lung, colorectal, prostate, brain, liver, kidney, pancreas, spleen, thymus, testis, ovary, uterus, etc., or tumor cell lines. If the source of mRNA is a primary tumor, mRNA can be extracted, for example, from frozen or archived fixed tissues, for example paraffin-embedded and fixed (e.g. formalin-fixed) tissue samples. General methods for mRNA extraction are well known in the art and are disclosed in standard textbooks of molecular biology, including Ausubel et al., Current Protocols of Molecular Biology, John Wiley and Sons (1997).

In particular, RNA isolation can be performed using purification kit, buffer set and protease from commercial manufacturers, according to the manufacturer's instructions. RNA prepared from tumor can be isolated, for example, by cesium chloride density gradient centrifugation. As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. The derived cDNA can then be used as a template in the subsequent PCR reaction.

To minimize errors and the effect of sample-to-sample variation. RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe. Real time PCR is compatible both with quantitative competitive PCR, where internal competitor for each target sequence is used for normalization, and with quantitative comparative PCR using a normalization gene contained within the sample, or a housekeeping gene for RT-PCR.

Fluorescence Microscopy: Some embodiments of the invention include fluorescence microscopy for analysis of PARP. Fluorescence microscopy enables the molecular composition of the structures being observed to be identified through the use of fluorescently-labeled probes of high chemical specificity such as antibodies. It can be done by directly conjugating a fluorophore to a protein and introducing this back into a cell. Fluorescent analogue may behave like the native protein and can therefore serve to reveal the distribution and behavior of this protein in the cell. Along with NMR, infrared spectroscopy, circular dichroism and other techniques, protein intrinsic fluorescence decay and its associated observation of fluorescence anisotropy, collisional quenching and resonance energy transfer are techniques for protein detection. The naturally fluorescent proteins can be used as fluorescent probes. The jellyfish *aequorea victoria* produces a naturally fluorescent protein known as green fluorescent protein (GFP). The fusion of these fluorescent probes to a target protein enables visualization by fluorescence microscopy and quantification by flow cytometry.

By way of example only, some of the probes are labels such as, fluorescein and its derivatives, carboxyfluoresceins, rhodamines and their derivatives, atto labels, fluorescent red and fluorescent orange: cy3/cy5 alternatives, lanthanide complexes with long lifetimes, long wavelength labels—up to 800 nm, DY cyanine labels, and phycobili proteins. By way of example only, some of the probes are conjugates such as, isothiocyanate conjugates, streptavidin conjugates, and biotin conjugates. By way of example only, some of the probes are enzyme substrates such as, fluorogenic and chromogenic substrates. By way of example only, some of the probes are fluorochromes such as, FITC (green fluorescence, excitation/emission=506/529 nm), rhodamine B (orange fluorescence, excitation/emission=560/584 nm), and nile blue A (red fluorescence, excitation/emission=636/686 nm). Fluorescent nanoparticles can be used for various types of immunoassays. Fluorescent nanoparticles are based on different materials, such as, polyacrylonitrile, and polystyrene etc. Fluorescent molecular rotors are sensors of microenvironmental restriction that become fluorescent when their rotation is constrained. Few examples of molecular constraint include increased dye (aggregation), binding to antibodies, or being trapped in the polymerization of actin. IEF (isoelectric focusing) is an analytical tool for the separation of ampholytes, mainly proteins. An advantage for IEF-gel electrophoresis with fluorescent IEF-marker is the possibility to directly observe the formation of gradient. Fluorescent IEF-marker can also be detected by UV-absorption at 280 nm (20° C.).

A peptide library can be synthesized on solid supports and, by using coloring receptors, subsequent dyed solid supports can be selected one by one. If receptors cannot indicate any color, their binding antibodies can be dyed. The method can not only be used on protein receptors, but also on screening binding ligands of synthesized artificial receptors and screening new metal binding ligands as well. Automated methods for HTS and FACS (fluorescence activated cell sorter) can also be used. A FACS machine originally runs cells through a capillary tube and separate cells by detecting their fluorescent intensities.

Immunoassays: Some embodiments of the invention include immunoassay for the analysis of PARP. In immunoblotting like the western blot of electrophoretically separated proteins a single protein can be identified by its antibody. Immunoassay can be competitive binding immunoassay where analyte competes with a labeled antigen for a limited pool of antibody molecules (e.g. radioimmunoassay, EMIT). Immunoassay can be non-competitive where antibody is present in excess and is labeled. As analyte antigen complex is increased, the amount of labeled antibody-antigen complex may also increase (e.g. ELISA). Antibodies can be polyclonal if produced by antigen injection into an experimental animal, or monoclonal if produced by cell fusion and cell culture techniques. In immunoassay, the antibody may serve as a specific reagent for the analyte antigen.

Without limiting the scope and content of the present invention, some of the types of immunoassays are, by way of example only, RIAs (radioimmunoassay), enzyme immunoassay's like ELISA (enzyme-linked immunosorbent assay), EMIT (enzyme multiplied immunoassay technique), microparticle enzyme immunoassay (MEIA), LIA (luminescent immunoassay), and FIA (fluorescent immunoassay). These techniques can be used to detect biological substances in the nasal specimen. The antibodies—either used as primary or secondary ones—can be labeled with radioisotopes (e.g. 125I), fluorescent dyes (e.g. FITC) or enzymes (e.g. HRP or AP) which may catalyse fluorogenic or luminogenic reactions.

Biotin, or vitamin H is a co-enzyme which inherits a specific affinity towards avidin and streptavidin. This interaction makes biotinylated peptides a useful tool in various biotechnology assays for quality and quantity testing. To improve biotin/streptavidin recognition by minimizing steric hindrances, it can be necessary to enlarge the distance between biotin and the peptide itself. This can be achieved by coupling a spacer molecule (e.g., 6-nitrohexanoic acid) between biotin and the peptide.

The biotin quantitation assay for biotinylated proteins provides a sensitive fluorometric assay for accurately determining the number of biotin labels on a protein. Biotinylated peptides are widely used in a variety of biomedical screening systems requiring immobilization of at least one of the interaction partners onto streptavidin coated beads, membranes, glass slides or microtiter plates. The assay is based on the displacement of a ligand tagged with a quencher dye from the biotin binding sites of a reagent. To expose any biotin groups in a multiply labeled protein that are sterically restricted and inaccessible to the reagent, the protein can be treated with protease for digesting the protein.

EMIT is a competitive binding immunoassay that avoids the usual separation step. A type of immunoassay in which the protein is labeled with an enzyme, and the enzyme-protein-antibody complex is enzymatically inactive, allowing quantitation of unlabelled protein. Some embodiments of the invention include ELISA to analyze PARP. ELISA is based on selective antibodies attached to solid supports combined with enzyme reactions to produce systems capable of detecting low levels of proteins. It is also known as enzyme immunoassay or EIA. The protein is detected by antibodies that have been made against it, that is, for which it is the antigen. Monoclonal antibodies are often used. The test may require the antibodies to be fixed to a solid surface, such as the inner surface of a test tube, and a preparation of the same antibodies coupled to an enzyme. The enzyme may be one (e.g., β-galactosidase) that produces a colored product from a colorless substrate. The test, for example, may be performed by filling the tube with the antigen solution (e.g., protein) to be assayed. Any antigen molecule present may bind to the immobilized antibody molecules. The antibody-enzyme conjugate may be added to the reaction mixture. The antibody part of the conjugate binds to any antigen molecules that are bound previously, creating an antibody-antigen-antibody "sandwich". After washing away any unbound conjugate, the substrate solution may be added. After a set interval, the reaction is stopped (e.g., by adding 1 N NaOH) and the concentration of colored product formed is measured in a spectrophotometer. The intensity of color is proportional to the concentration of bound antigen.

ELISA can also be adapted to measure the concentration of antibodies, in which case, the wells are coated with the appropriate antigen. The solution (e.g., serum) containing antibody may be added. After it has had time to bind to the immobilized antigen, an enzyme-conjugated anti-immunoglobulin may be added, consisting of an antibody against the antibodies being tested for. After washing away unreacted reagent, the substrate may be added. The intensity of the color produced is proportional to the amount of enzyme-labeled antibodies bound (and thus to the concentration of the antibodies being assayed).

Some embodiments of the invention include radioimmunoassays to analyze PARP. Radioactive isotopes can be used to study in vivo metabolism, distribution, and binding of small amount of compounds. Radioactive isotopes of $^1$H, $^{12}$C, $^{31}$P, $^{32}$S, and $^{127}$I in body are used such as $^3$H, $^{14}$C, $^{32}$P, $^{35}$S, and $^{125}$I. In receptor fixation method in 96 well plates, receptors may be fixed in each well by using antibody or chemical methods and radioactive labeled ligands may be added to each well to induce binding. Unbound ligands may be washed out and then the standard can be determined by quantitative analysis of radioactivity of bound ligands or that of washed-out ligands. Then, addition of screening target compounds may induce competitive binding reaction with receptors. If the compounds show higher affinity to receptors than standard radioactive ligands, most of radioactive ligands would not bind to receptors and may be left in solution. Therefore, by analyzing quantity of bound radioactive ligands (or washed-out ligands), testing compounds' affinity to receptors can be indicated.

The filter membrane method may be needed when receptors cannot be fixed to 96 well plates or when ligand binding needs to be done in solution phase. In other words, after ligand-receptor binding reaction in solution, if the reaction solution is filtered through nitrocellulose filter paper, small molecules including ligands may go through it and only protein receptors may be left on the paper. Only ligands that strongly bound to receptors may stay on the filter paper and the relative affinity of added compounds can be identified by quantitative analysis of the standard radioactive ligands.

Some embodiments of the invention include fluorescence immunoassays for the analysis of PARP. Fluorescence based immunological methods are based upon the competitive binding of labeled ligands versus unlabeled ones on highly specific receptor sites. The fluorescence technique can be used for immunoassays based on changes in fluorescence lifetime with changing analyte concentration. This technique may work with short lifetime dyes like fluorescein isothiocyanate (FITC) (the donor) whose fluorescence may be quenched by energy transfer to eosin (the acceptor). A number of photoluminescent compounds may be used, such as cyanines, oxazines, thiazines, porphyrins, phthalocyanines, fluorescent infrared-emitting polynuclear aromatic hydrocarbons, phycobiliproteins, squaraines and organo-metallic complexes, hydrocarbons and azo dyes.

Fluorescence based immunological methods can be, for example, heterogenous or homogenous. Heterogenous immunoassays comprise physical separation of bound from free labeled analyte. The analyte or antibody may be attached to a solid surface. The technique can be competitive (for a higher selectivity) or noncompetitive (for a higher sensitivity). Detection can be direct (only one type of antibody used) or indirect (a second type of antibody is used). Homogenous immunoassays comprise no physical separation. Double-antibody fluorophore-labeled antigen participates in an equilibrium reaction with antibodies directed against both the antigen and the fluorophore. Labeled and unlabeled antigen may compete for a limited number of anti-antigen antibodies.

Some of the fluorescence immunoassay methods include simple fluorescence labeling method, fluorescence resonance energy transfer (FRET), time resolved fluorescence (TRF), and scanning probe microscopy (SPM). The simple fluorescence labeling method can be used for receptor-ligand binding, enzymatic activity by using pertinent fluorescence, and as a fluorescent indicator of various in vivo physiological changes such as pH, ion concentration, and electric pressure. TRF is a method that selectively measures fluorescence of the lanthanide series after the emission of other fluorescent molecules is finished. TRF can be used with FRET and the lanthanide series can become donors or acceptors. In scanning probe microscopy, in the capture phase, for example, at least one monoclonal antibody is adhered to a solid phase and a scanning probe microscope is utilized to detect antigen/antibody complexes which may be present on the surface of the solid phase. The use of scanning tunneling microscopy eliminates the need for labels which normally is utilized in many immunoassay systems to detect antigen/antibody complexes.

Protein identification methods: By way of example only, protein identification methods include low-throughput sequencing through Edman degradation, mass spectrometry techniques, peptide mass fingerprinting, de novo sequencing, and antibody-based assays. The protein quantification assays include fluorescent dye gel staining, tagging or chemical modification methods (i.e. isotope-coded affinity tags (ICATS), combined fractional diagonal chromatography (COFRADIC)). The purified protein may also be used for determination of three-dimensional crystal structure, which can be used for modeling intermolecular interactions. Common methods for determining three-dimensional crystal structure include x-ray crystallography and NMR spectroscopy. Characteristics indicative of the three-dimensional structure of proteins can be probed with mass spectrometry. By using chemical crosslinking to couple parts of the protein that are close in space, but far apart in sequence, information about the overall structure can be inferred. By following the exchange of amide protons with deuterium from the solvent, it is possible to probe the solvent accessibility of various parts of the protein.

In one embodiment, fluorescence-activated cell-sorting (FACS) is used to identify PARP expressing cells. FACS is a specialised type of flow cytometry. It provides a method for sorting a heterogenous mixture of biological cells into two or more containers, one cell at a time, based upon the specific light scattering and fluorescent characteristics of each cell. It provides quantitative recording of fluorescent signals from individual cells as well as physical separation of cells of particular interest. In yet another embodiment, microfluidic based devices are used to evaluate PARP expression.

Mass spectrometry can also be used to characterize PARP from patient samples. The two methods for ionization of whole proteins are electrospray ionization (ESI) and matrix-assisted laser desorption/ionization (MALDI). In the first, intact proteins are ionized by either of the two techniques described above, and then introduced to a mass analyser. In the second, proteins are enzymatically digested into smaller peptides using an agent such as trypsin or pepsin. Other proteolytic digest agents are also used. The collection of peptide products are then introduced to the mass analyser. This is often referred to as the "bottom-up" approach of protein analysis.

Whole protein mass analysis is conducted using either time-of-flight (TOF) MS, or Fourier transform ion cyclotron resonance (FT-ICR). The instrument used for peptide mass analysis is the quadrupole ion trap. Multiple stage quadrupole-time-of-flight and MALDI time-of-flight instruments also find use in this application.

Two methods used to fractionate proteins, or their peptide products from an enzymatic digestion. The first method fractionates whole proteins and is called two-dimensional gel electrophoresis. The second method, high performance liquid chromatography is used to fractionate peptides after enzymatic digestion. In some situations, it may be necessary to combine both of these techniques.

There are two ways mass spectroscopy can be used to identify proteins. Peptide mass uses the masses of proteolytic peptides as input to a search of a database of predicted masses that would arise from digestion of a list of known proteins. If a protein sequence in the reference list gives rise to a significant number of predicted masses that match the experimental values, there is some evidence that this protein is present in the original sample.

Tandem MS is also a method for identifying proteins. Collision-induced dissociation is used in mainstream applications to generate a set of fragments from a specific peptide ion. The fragmentation process primarily gives rise to cleavage products that break along peptide bonds.

A number of different algorithmic approaches have been described to identify peptides and proteins from tandem mass spectrometry (MS/MS), peptide de novo sequencing and sequence tag based searching. One option that combines a comprehensive range of data analysis features is PEAKS. Other existing mass spec analysis software include: Peptide fragment fingerprinting SEQUEST, Mascot, OMSSA and XITandem).

Proteins can also be quantified by mass spectrometry. Typically, stable (e.g. non-radioactive) heavier isotopes of carbon (C13) or nitrogen (N15) are incorporated into one sample while the other one is labelled with corresponding light isotopes (e.g. C12 and N14). The two samples are mixed before the analysis. Peptides derived from the different samples can be distinguished due to their mass difference. The ratio of their peak intensities corresponds to the relative abundance ratio of the peptides (and proteins). The methods for isotope labelling are SILAC (stable isotope labelling with amino acids in cell culture), trypsin-catalyzed O18 labeling, ICAT (isotope coded affinity tagging), ITRAQ (isotope tags for relative and absolute quantitation). "Semi-quantitative" mass spectrometry can be performed without labeling of samples. Typically, this is done with MALDI analysis (in linear mode). The peak intensity, or the peak area, from individual molecules (typically proteins) is here correlated to the amount of protein in the sample. However, the individual signal depends on the primary structure of the protein, on the complexity of the sample, and on the settings of the instrument.

N-terminal sequencing aids in the identification of unknown proteins, confirm recombinant protein identity and fidelity (reading frame, translation start point, etc.), aid the interpretation of NMR and crystallographic data, demonstrate degrees of identity between proteins, or provide data for the design of synthetic peptides for antibody generation, etc. N-terminal sequencing utilises the Edman degradative chemistry, sequentially removing amino acid residues from the N-terminus of the protein and identifying them by reverse-phase HPLC. Sensitivity can be at the level of 100 s femtomoles and long sequence reads (20-40 residues) can often be obtained from a few 10 s picomoles of starting material. Pure proteins (>90%) can generate easily interpreted data, but insufficiently purified protein mixtures may also provide useful data, subject to rigorous data interpretation. N-terminally modified (especially acetylated) proteins cannot be sequenced directly, as the absence of a free primary amino-group prevents the Edman chemistry. However, limited proteolysis of the blocked protein (e.g. using cyanogen bromide) may allow a mixture of amino acids to be generated in each cycle of the instrument, which can be subjected to database analysis in order to interpret meaningful sequence information. C-terminal sequencing is a post-translational modification, affecting the structure and activity of a protein. Various disease situations can be associated with impaired protein processing and C-terminal sequencing provides an additional tool for the investigation of protein structure and processing mechanisms.

EXAMPLES

Example 1

PARP1 Expression in IDC Breast Cancer

Previous studies have shown increased PARP activity in ovarian cancers, hepatocellular carcinomas, and rectal tumors, compared with normal healthy control tissues, as well as in human peripheral blood lymphocytes from leukemia patients (Yalcintepe L, et. al. Braz J Med Biol Res 2005; 38:361-5. Singh N. et. al. Cancer Lett 1991; 58:131-5; Nomura F, et. al. J Gastroenterol Hepatol 2000; 15:529-35). This invention uses the gene expression databases to examine PARP1 gene regulation in more than 2000 primary malignant and normal human tissues. While PARP1 expression and activity is very low and uniform across the majority of normal human tissues and organs, it is upregulated in selected tumor cells and primary human malignancies, with the most striking differences found in breast, ovarian, lung, and uterine cancers (FIG. 1).

Tissue Samples

Specimens are harvested as part of a normal surgical procedure and flash frozen within 30 minutes of resection. Internal pathology review and confirmation are performed on samples subjected to analysis. Hematoxylin and eosin (H&E)-stained glass slides generated from adjacent tissues are used to confirm and classify diagnostic categories and to evaluate neoplastic cellularity. Expression of ER. PR, and HER2 is determined using immunohistochemistry and fluorescence in sill hybridization. These results, as well as attendant pathology and clinical data, are annotated with sample inventory and management databases (Ascenta, BioExpress databases; GeneLogic, Inc., Gaithersburg, Md.).

RNA Extraction and Expression Profiling

RNA extraction and hybridization are performed as described by Hansel et al. Array data quality is evaluated using array high throughput application (Ascenta, BioExpress Gene Logic, Gaithersburg Md. and Affymetrix, Santa Clara, Calif.), which assesses the data against multiple objective standards including 5'/3' GAPDH ratio, signal/noise ratio, and background as well as other additional metrics. GeneChip analysis is performed with Affymetrix Microarray Analysis Suite version 5.0, Data Mining Tool 2.0, and Microarray database software (Affymetrix, Santa Clara, Calif.). All of the genes represented on the GeneChip are globally normalized and scaled to a signal intensity of 100.

Microarray Data Analysis

Pathologically normal tissue samples are used to determine baseline expression of the PARP1 mRNA. The mean and 90%, 95%, 99%, and 99.9% upper confidence limits (UCLs) for an individual predicted value are calculated. Because we are assessing the likelihood that individual samples external to the normal set are within the baseline distribution, the prediction interval, rather than the confidence interval for the mean, is selected to estimate the expected range for future individual measurements. The prediction interval is defined by the formula, $\overline{X} \pm AS\sqrt{1+(1/n)}$, where $\overline{X}$ is the mean of the normal breast samples, S is the standard deviation, n is the sample size, and A is the $100(1-(p/2))^{th}$ percentile of the Student's t-distribution with n−1 degrees of freedom.

Pathologically normal tissue samples is used to determine baseline expression of the PARP1. Samples are grouped into various subcategories according to characteristics including tumor stage, smoking status, CA 125 status, or age. Each tumor sample is evaluated according to 90%, 95%, 99%, or 99.9% UCLs Analysis is performed using SAS v8.2 for Windows (www.sas.com).

Pearson's correlations are calculated for 11 probe sets as compared to PARP1. Correlations are based on the complete set of 194 samples. The Pearson's product-moment correlation is defined by the formula, $$r_{xy} = \frac{\sum (x_i - \overline{x})(y_i - \overline{y})}{\sqrt{\sum (x_i - \overline{x})^2 \sum (y_i - \overline{y})^2}},$$

where $\overline{X}$ is the mean of the PARP1 probe set and $\overline{Y}$ is the mean of the probe set to which PARP1 is being correlated. Statistical significance is determined by the formula, $$\frac{(n-2)^{1/2} r}{(1-r^2)^{1/2}},$$

where r is the correlation and n is the number of samples. The resultant value is assumed to have at distribution with n−2 degrees of freedom.

Multiplex Reverse Transcriptase-Polymerase Chain Reaction (RT-PCR):

Multiplex RT-PCR is performed using 25 ng of total RNA of each sample as previously described (Khan et al., 2007). The multiplex assay used for this study is designed to detect RNA from formalin fixed paraffin embedded (FFPE) samples or from frozen tissues. The concentration of the RNA is determined using the RiboGreen RNA Quantitation Kit (Invitrogen) with Wallac Victo r2 1420 Multilabel Counter. A sample of RNA from each sample is analyzed on an Agilent Bioanalyzer following instructions of Agilent 2100 Bioanalyzer. Reverse transcription (RT) reactions are carried out as previously described with the Applied Biosystems 9700. PCR reactions are carried out on each cDNA with the Applied Biosystems 9700. RT reactions are spiked with Kanamycin RNA to monitor efficiency of the RT and PCR reactions. Controls used included positive control RNA, a no template control, and a no reverse transcriptase control. PCR reactions are analyzed by capillary electrophoresis. The fluorescently labeled PCR reactions are diluted, combined with Genome Lab size standard-400 (Beckman-Coulter,), denatured, and assayed with the CEQ 8800 Genetic Analysis System. The expression of each target gene relative to the expression of β-glucuronidase (GUSB) within the same reaction is reported as the mean and standard deviation of 3 independent assessments for each sample.

Breast cancer patients with infiltrating ductal carcinoma (IDC) have a 1.8-fold increase in mean PARP1 expression compared with normal breast tissues (P<0.00001). Importantly, PARP1 overexpression occurs most frequently in breast cancer tissues that are negative for ER, PR, or HER2 (Table 1).

TABLE 1

PARP1 overexpression in IDC breast tissues

| IDC Subtype | n | % Samples w/PARP1 Overexpression |
|---|---|---|
| Normal | 68 | 2.9% |
| IDC | 169 | 30.2% |
| ER+ | 35 | 22.9% |
| ER− | 18 | 55.6% |
| PR+ | 26 | 23.1% |
| PR− | 20 | 45.0% |
| HER2+ | 24 | 29.2% |
| HER2− | 10 | 70.0% |
| ER+/PR+ | 26 | 23.1% |
| ER−/PR− | 8 | 62.5% |
| ER+/PR− | 8 | 25.0% |

PARP1 overexpression was defined by samples that exceeded the 95% upper confidence limit in a normal breast tissue distribution.

Example 2

Combination of 4-iodo-3-nitrobenzamide (BA) with Chemotherapy Cell Culture

Breast cancer cells are obtained from ATCC and cultured in Dulbecco Modified Eagle Medium with 10% fetal bovine serum. Cells are plated at $10^5$ cells per P100 cell culture dish or at $10^4$ cells per P60 cell culture dish in the presence of different concentrations compounds or DMSO control. Following treatment, the number of attached cells is measured using Coulter counter, and by staining with 1% methylene blue. Methylene blue is dissolved in 50%-50% mixture of Methanol and water. Cells are plated in 24- or 96-well plates and treated as planned, media are aspirated, cells are washed with PBS, fixed in methanol for 5-10 min, methanol is aspirated and plates are allowed to dry completely. Methylene blue solution is added to wells and plates are incubated for 5 min. Staining solution is removed and plates are washed with dH2O until washes are no longer blue. After plates are completely dry, a small amount of 1N HCl is added to each well to extract the methylene blue. The OD readout at 600 nm and a calibration curve are used to determine cell number.

Compounds

Compounds are dissolved directly from dry powder to 10 mM stock solution in DMSO for each separate experiment. Control experiments are carried out with the matching volume/concentration of the vehicle (DMSO); in these controls, the cells show no changes in their growth or cell cycle distribution.

PI Exclusion, Cell Cycle and TUNEL Assays

After the addition of drugs and incubation, cells are trypsinized and aliquots of the samples are taken for counting and PI (Propidium Iodide) exclusion assay. One part of the cells is centrifuged and resuspended in 0.5 ml ice-cold PBS containing 5 μg/ml of PI. The other part of the cells is fixed in ice-cold 70% ethanol and stored in a freezer overnight. For cell cycle analysis, cells are stained with propidium iodide (PI) by standard procedures. Cellular DNA content is determined by flow cytometry using BD LSRII FACS, and the percentages of cells in G1, S or G2/M are determined using ModFit software.

The cells are labeled for apoptosis with the "In Situ Cell Death Detection Kit, Fluorescein" (Roche Diagnostics Corporation, Roche Applied Science, Indianapolis, Ind.). Briefly, fixed cells are centrifuged and washed once in phosphate-buffered saline (PBS) containing 1% bovine serum albumin (BSA), then resuspended in 2 ml permeabilization buffer (0.1% Triton X-100 and 0.1% sodium citrate in PBS) for 25 min at room temperature and washed twice in 0.2 ml PBS/1% BSA. The cells are resuspended in 50 μl TUNEL reaction mixture (TdT enzyme and labeling solution) and incubated for 60 min at 37° C. in a humidified dark atmosphere in an incubator. The labeled cells are washed once in PBS/1% BSA, then resuspended in 0.5 ml ice-cold PBS containing 1 μg/ml 4',6-diamidino-2-phenylindole (DAPI) for at least 30 min. All cell samples are analyzed with a BD LSR II (BD Biosciences, San Jose, Calif.).

Bromodeoxyuridine (BrdU) Labeling Assay

50 μl of BrdU (Sigma Chemical Co., St. Louis, Mo.) stock solution (1 mM) is added to give 10 μM BrdU final concentration. The cells are incubated for 30 min at 37° C. and fixed in ice-cold 70% ethanol and stored in a cold room (4° C.) overnight. Fixed cells are centrifuged and washed once in 2 ml PBS, then resuspended in 0.7 ml of denaturation solution (0.2 mg/ml pepsin in 2 N HCl) for 15 min at 37° C. in the dark and suspended with 1.04 ml 1M Tris buffer (Trizma base, Sigma Chemical Co.) and washed in 2 ml PBS. Then cells are resuspended in 100-μl anti-BrdU antibody (DakoCytomation, Carpinteria, Calif.) with 1:100 dilution in TBFP permeable buffer (0.5% Tween-20, 1% bovine serum albumin and 1% fetal bovine serum in PBS) and incubated for 25 min at room temperature in the dark and washed in 2 ml PBS. The primary antibody-labeled cells are resuspended in 100 μl Alexa Fluor F(ab')2 fragment of goat anti-mouse IgG (H+L) (2 mg/mL) (Molecular Probes, Eugene, Oreg.) with 1:200 dilution in TBFP permeable buffer and incubated for 25 min at room temperature in the dark and washed in 2 ml PBS, then resuspended in 0.5 ml ice-cold PBS containing 1 μg/ml 4',6-diamidino-2-phenylindole (DAPI) for at least 30 min. All cell samples are analyzed with a BD LSR II (BD Biosciences, San Jose, Calif.).

Figure 2:
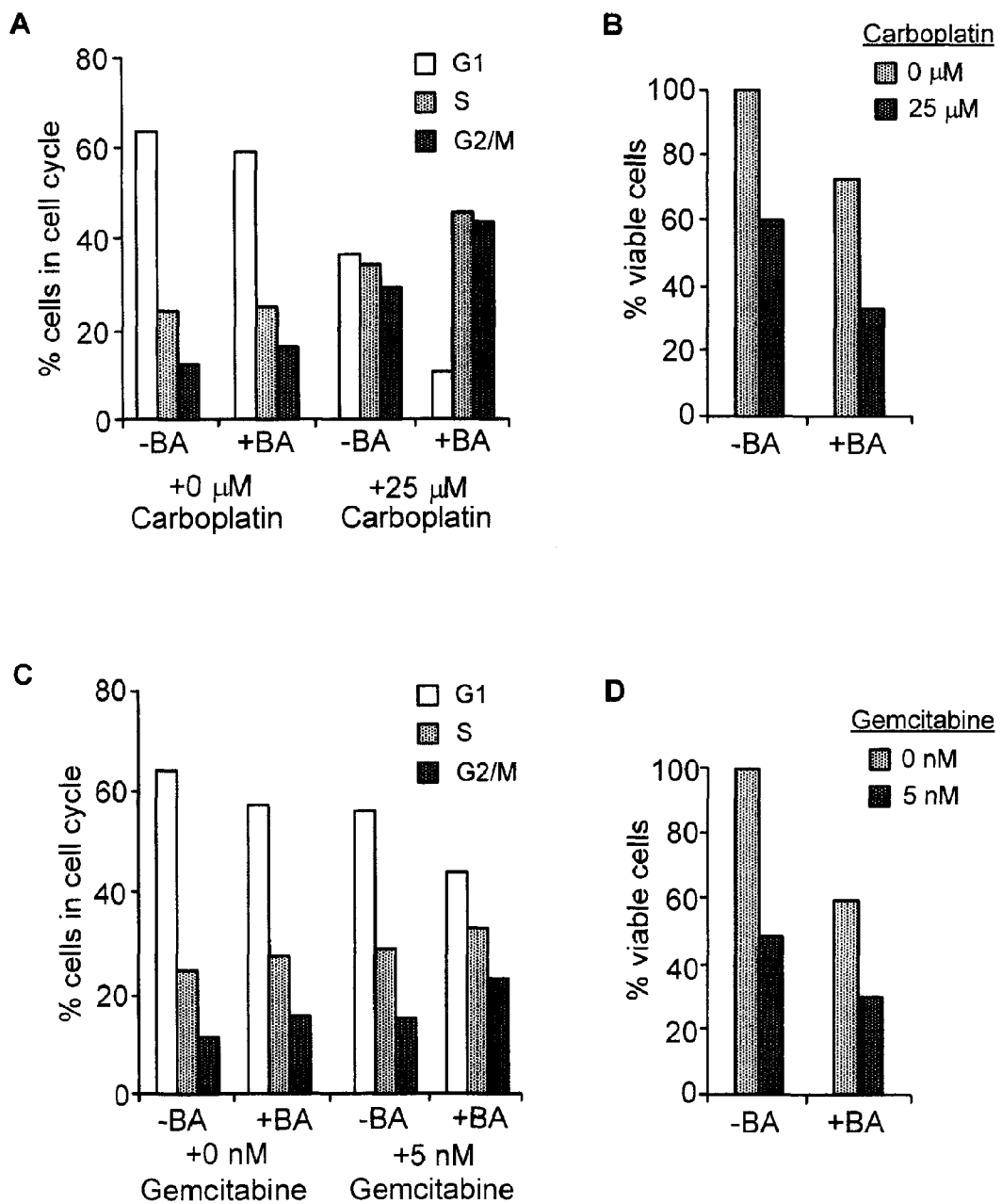
FIG. 2 shows effect of 4-iodo-3-nitrobenzamide plus carboplatin or gemcitabine on in vitro TNBC cell cycle progression. Viability of MDA-MB-463 TNBC cells is quantified by FACS analysis.

Combinations of 4-iodo-3-nitrobenzamide (BA) with various chemotherapeutic agents have been tested in in vitro and in vivo models of cancer. Evaluation of BA in combination with gemcitabine or carboplatin in the MDA-MB-468 breast adenocarcinoma cell line, derived from a patient with metastatic triple negative adenocarcinoma, shows that BA potentiates S- and G2/M cell cycle arrest and enhances cytotoxic effects induced by either carboplatin or gemcitabine (FIG. 2).

BA activity in a combination with gemcitabine and carboplatin is evaluated in the human triple negative metastatic breast carcinoma MDA-MB-231 xenograft model in nude nu/nu mice. BA increases the activity of the combination of gemcitabine and carboplatin and results in 4 partial responses (PR) and 2 complete responses (CR) and 1 tumor-free survivor (TFS) after 35 days of drugs administration (Table 2). The combination of BA with gemcitabine and carboplatin is well tolerated.

TABLE 2

In vivo activity of BA in combination with gemcitabine/carboplatin in MDA-MB-231 xenograft model of triple negative breast adenocarcinoma

| Treatment | Partial Response | Complete Response | Tumor-Free Survivors |
|---|---|---|---|
| Control | 0 | 0 | 0 |
| Gemcitabine (15 mg/kg; ip; q3dx4 ip) + Carboplatin (10 mg/kg; ip; qwkx3) | 4 | 0 | 0 |
| BSI-201 (50 mg/kg; ip; biwk) + Gemcitabine (15 mg/kg; ip; q3dx4 ip) + Carboplatin (10 mg/kg; ip; qwkx3) | 4 | 2 | 1 |

Thus, 4-iodo-3-nitrobenzamide (BA) can potentiate the activity of a variety of cytotoxic chemotherapeutic agents, including carboplatin and gemcitabine.

Example 3

Combination of 4-iodo-3-nitrobenzamide (BA) with Irinotecan

Breast cancer cells are obtained from ATCC and cultured in Dulbecco Modified Eagle Medium with 10% fetal bovine serum. Cells are plated at $10^5$ cells per P100 cell culture dish or at $10^4$ cells per P60 cell culture dish in the presence of different concentrations compounds or DMSO control. Following treatment, the number of attached cells is measured using Coulter counter, and by staining with 1% methylene blue. Methylene blue is dissolved in 50%-50% mixture of Methanol and water. Cells are plated in 24- or 96-well plates and treated as planned, media are aspirated, cells are washed with PBS, fixed in methanol for 5-10 min. methanol is aspirated and plates are allowed to dry completely. Methylene blue solution is added to wells and plates are incubated for 5 min. Staining solution is removed and plates are washed with dH2O until washes are no longer blue. After plates are completely dry, a small amount of 1N HCl is added to each well to extract the methylene blue. The OD readout at 600 nm and a calibration curve are used to determine cell number.

Compounds are dissolved directly from dry powder to 10 mM stock solution in DMSO for each separate experiment. Control experiments are carried out with the matching volume/concentration of the vehicle (DMSO); in these controls, the cells show no changes in their growth or cell cycle distribution.

PI exclusion, cell cycle, TUNEL assays, and BrdU labeling assays are performed as described above in Example 2.

Combinations of various concentrations of 4-iodo-3-nitrobenzamide (BA) with irinotecan are tested in in vitro models of cancer. Evaluation of BA in combination with irinotecan in the MDA-MB-468 triple negative breast adenocarcinoma cell line, derived from a patient with metastatic triple negative adenocarcinoma, shows that BA potentiates S- and G2/M cell cycle arrest and enhances cytotoxic effects induced by irinotecan (Table 3).

TABLE 3

Cell cycle regulation of triple negative MDA-MB-468 breast carcinoma treated with 4-iodo-3-nitrobenzamide (BA) in a combination with irinotecan

| Irinotecan | G1 | S | G2/M | vital cells, % control |
|---|---|---|---|---|
| Irinotecan 0 uM + BA uM | | | | |
| 0 | 64.40 | 24.18 | 11.42 | 100.0 |
| 50 | 65.50 | 23.48 | 11.02 | 91.5 |
| 100 | 57.72 | 26.93 | 15.34 | 67.5 |
| Irinotecan 5 uM + BA uM | | | | |
| 0 | 38.17 | 33.77 | 28.05 | 48.6 |
| 50 | 24.94 | 41.85 | 33.21 | 31.6 |
| 100 | 9.28 | 51.43 | 39.29 | 23.4 |

Thus, 4-iodo-3-nitrobenzamide (BA) can potentiate the activity of a variety of cytotoxic chemotherapeutic agents, including carboplatin, gemcitabine and irinotecan.

Example 4

Combination of 4-iodo-3-nitrobenzamide (BA) with IGF1R inhibitor Picropodophyllin (PPP)

Breast cancer cells are obtained from ATCC and cultured in Dulbecco Modified Eagle Medium with 10% fetal bovine serum. Cells are plated at $10^5$ cells per P100 cell culture dish or at $10^4$ cells per P60 cell culture dish in the presence of different concentrations compounds or DMSO control. Following treatment, the number of attached cells is measured using Coulter counter, and by staining with 1% methylene blue. Methylene blue is dissolved in 50%-50% mixture of Methanol and water. Cells are plated in 24- or 96-well plates and treated as planned, media are aspirated, cells are washed with PBS, fixed in methanol for 5-10 min, methanol is aspirated and plates are allowed to dry completely. Methylene blue solution is added to wells and plates are incubated for 5 min. Staining solution is removed and plates are washed with dH2O until washes are no longer blue. After plates are completely dry, a small amount of 1N HCl is added to each well to extract the methylene blue. The OD readout at 600 nm and a calibration curve are used to determine cell number.

Compounds are dissolved directly from dry powder to 10 mM stock solution in DMSO for each separate experiment. Control experiments are carried out with the matching volume/concentration of the vehicle (DMSO); in these controls, the cells show no changes in their growth or cell cycle distribution.

PI exclusion, cell cycle, TUNEL assays, and BrdU labeling assays are performed as described above in Example 2.

Combinations of various concentrations of 4-iodo-3-nitrobenzamide (BA) with insulin-like growth factor 1 receptor (IGF1R) inhibitor Picropodophyllin (PPP) are tested in in vitro models of cancer. Evaluation of BA in combination with PPP in the MDA-MB-468 triple negative breast adenocarcinoma cell line, derived from a patient with metastatic triple negative adenocarcinoma, shows that BA potentiates S- and G2/M cell cycle arrest and enhances cytotoxic effects induced by PPP (Table 4).

TABLE 4

Cell cycle regulation of triple negative MDA-MB-468 breast carcinoma treated with 4-iodo-3-nitrobenzamide (BA) in a combination with IGF1R inhibitor Picropodophyllin (PPP)

|  | G1 | S | G2/M | Vital Cell % control |
|---|---|---|---|---|
| PPP 0 nM + 201 uM | | | | |
| 0 | 50.96 | 30.37 | 16.04 | 100 |
| 50 | 50.20 | 31.34 | 15.21 | 82 |
| 100 | 40.63 | 34.52 | 20.16 | 61 |
| PPP 200 nM + 201 uM | | | | |
| 0 | 51.42 | 30.22 | 15.01 | 89 |
| 50 | 49.75 | 31.41 | 15.10 | 77 |
| 100 | 37.51 | 35.58 | 21.30 | 59 |
| PPP 400 nM + 201 uM | | | | |
| 0 | 37.29 | 25.32 | 20.17 | 60 |
| 50 | 32.88 | 28.47 | 22.37 | 42 |
| 100 | 23.62 | 31.78 | 29.98 | 32 |

Thus, 4-iodo-3-nitrobenzamide (BA) can potentiate the activity of targeted inhibitors of growth factor receptors including picropodophyllin (PPP).

Example 5

Treatment of Triple Negative Breast Cancer with BA

A multi-center, open-label, randomized study to demonstrate the therapeutic effectiveness in the treatment of triple negative metastatic breast cancer with 4-iodo-3-nitrobenzamide (BA) is conducted.

Study Objectives: the Primary Objectives of this Study are as Follows:

Clinical Benefit Rate (CBR=CR+PR+SD≧6 months): Determine that BA will produce a CBR of 30% or greater as compared to the CBR of 45% associated with treatment with gemcitabine and carboplatin.
  To further study the safety and tolerability of BA
  The secondary objectives of this study are as follows:
  Overall Response Rate (ORR)
  Progression-free survival (PFS)
  Evaluation of the toxicity associated with each arm
  The exploratory objectives of this study are as follows:
  To characterize the inhibition of PARP activity by BA
  To characterize PARP activity in historic tumor tissue samples
  To study the status of BRCA in triple negative breast cancer
  To study the response in subjects with cancer and known BRCA mutations compared to subjects without these mutations
  To classify breast cancer tissue as either basal or luminal
  Study Design: An open label, 2-arm randomized, safety and efficacy study in which up to 90 patients (45 in each arm) will be randomized to either:
  Study Arm 1: Gemcitabine (1000 mg/m$^2$; 30 min IV infusion) and Carboplatin (AUC 2; 60 min IV infusion) on days 1 and 8 of a 21-day cycle; or
  Study Arm 2: 4-iodo-3-nitrobenzamide (4 mg/kg 1 hour IV infusion) on days 1, 4, 8 and 11 of each 21-day cycle
  Patients randomized to Study Arm 2 will be discontinued from the study at the time of disease progression
  Crossover: Patients randomized to Study Arm 1 may cross over to receive continued treatment with gemcitabine/carboplatin in combination with 4-iodo-3-nitrobenzamide at the time of disease progression
  Sample Size: Up to 90 subjects, up to 45 in each arm participate in the study. Subjects will be randomized, up to 45 in each of Arm-1 or Arm-2.
Subject Population:
Inclusion Criteria:
At least 18 years of age
Metastatic breast cancer (Stage 1V) with measurable disease by RECIST criteria
0-2 prior chemotherapy regimens in the metastatic setting. Prior adjuvant/neoadjuvant therapy is allowed.
Histology documents (either primary or metastatic site) breast cancer that is ER-negative, PR-negative and HER-2 non-overexpressing by immunohistochemistry (0, 1) or non-gene amplified by FISH performed upon the primary tumor or metastatic lesion.
Completion of prior chemotherapy at least 3 weeks prior to study entry.
Patients may have received therapy in the adjuvant or metastatic setting, however if taking bisphosphonates, bone lesions may not be used for progression or response.
Radiation therapy must be completed at least 2 weeks prior to study entry, and radiated lesions may not serve as measurable disease.
Patients may have CNS metastases if stable (no evidence of progression) for at least 3 months after local therapy
ECOG performance status 0-1
Adequate organ function defined as: ANC greater than or equal to 1,5000/mm$^3$, platelets greater than or equal to 100,000/mm$^3$, creatinine clearance greater than 50 mL/min, ALT and AST lower than 2.5× upper limit of normal (ULN) (Or lower than 5×ULN in case of liver metastases); total biliruibin lower than 1.5 mg/dL.
Tissue block available for PARP studies is recommended, although will not exclude patients from participating
Pregnant or lactating women will be excluded. Women of child bearing potential must have documented negative pregnancy test within two weeks of study entry and agree to acceptable birth control during the duration of the study therapy
Signed, IRB approved written informed consent
Exclusion Criteria:
Lesions identifiable only by PET
More than 2 prior chemotherapy regimens (including adjuvant). Sequential regimens such as AC-paclitaxel are considered one regimen.
Has received prior treatment with gemcitabine, carboplatin, cisplatin or 4-iodo-3-nitrobenzamide.
Major medical conditions that might affect study participation (uncontrolled pulmonary, renal or hepatic dysfunction, uncontrolled infection).
Significant history of uncontrolled cardiac disease; i.e., uncontrolled hypertension, unstable angina, recent myocardial infarction (within prior 6 months), uncontrolled congestive heart failure, and cardiomyopathy that is either symptomatic or asymptomatic but with decreased ejection fraction lower than 45%.
Other significant comorbid condition which the investigator feels might compromise effective and safe participation in the study.
Subject enrolled in another investigational device of drug trial, or is receiving other investigational agents Concurrent or prior (within 7 days of study day 1) anticoagulation therapy (low dose for port maintenance allowed)

Specified concomitant medications

Concurrent radiation therapy is not permitted throughout the course of the study Inability to comply with the requirements of the study Screening tests and evaluation will be performed only after a signed, written Institutional Review Board (IRB) approved informed consent is obtained from each subject. Procedures will be performed within 14 days of dosing (day 1) unless otherwise noted.

Clinical evaluation: Complete history, physical examination, ECOG status, height, weight, vital signs, and documentation of concomitant medications.

Laboratory studies: Hematology (with differential, reticulocyte count, and platelets); prothrombin time (PT) and partial thromboplastin time (PTT); comprehensive chemistry panel (sodium, potassium, chloride, $CO_2$, creatinine, calcium, phosphorus, magnesium, BUN, uric acid, albumin, AST, ALT, alkaline phosphatase, total bilirubin, and cholesterol, HDL and LDL), urinalyisis with microscopic examination, PARP inhibition in PBMCs, serum or urine pregnancy test for women of child bearing potential. BRCA profiling will be obtained if a separate informed consent is signed. This information may be also pulled from a subject's medical history. Clinical staging: imaging for measurable disease by computed tomography (CT) or magnetic resonance (MRI).

Treatment: Eligible patients will be enrolled in the study and randomized to either Arm 1 or Arm 2:

Study Arm 1: Gemcitabine (1000 mg/m$^2$; 30 min IV infusion) and Carboplatin (AUC 2; 60 min IV infusion) on days 1 and 8 of a 21-day cycle; or Study Arm 2: 4-iodo-3-nitrobenzamide (4 mg/kg, 1 hour IV infusion) on days 1, 4, 8 and 11 of each 21-day cycle.

Crossover: Patients randomized to study arm 1 may crossover to receive continued treatment with gemcitabine/carboplatin in combination with 4-iodo-3-nitrobenzamide at the time of disease progression.

Pre-dose and post-dose tests will be performed as outlined in the study protocol.

Dosing for both treatment arms will be repeated in 21-day cycles.

Subjects may participate in this study until they experience a drug intolerance or disease progression or withdraw consent. Subjects that achieve a CR would receive an additional 4 cycles. Subjects that discontinue treatment before PD should undergo regular staging evaluation per protocol until time of PD. Once a subject discontinues treatment, evaluation for progression free survival and overall response rate will continue at 3-month intervals until disease progression or death.

The first scheduled tumor response measurement for measurable disease will be performed after cycle 2, and then every other cycles of therapy (approximately every 6-8 weeks) in addition to the initial staging done at baseline. Tumor response according to the modified Response Evaluation Criteria in Solid Tumors (RECIST) will be used to establish disease progression by CT or MRI (the same technique used during screening must be used).

End of Treatment: All subjects should have the end of treatment procedures as described in the protocol completed no more than 30 days after the last dose of 4-iodo-3-nitrobenzamide. Additionally, subjects will have overall tumor response assessed via clinical imaging if not done within 30 days prior to the last dose of 4-iodo-3-nitrobenzamide.

Assessment of Safety: Safety will be assessed by standard clinical and laboratory tests (hematology, blood chemistry, and urinalysis). Toxicity grade is defined by the National Cancer Institute CTCAE v3.0.

Pharmacokinetics/Pharmacodynamics

Blood samples for PK and pharmacodynamic analysis will be obtained only from subjects who are enrolled onto study arm 2. This includes crossover subjects.

PK Samples will be collected during cycle 1, pre dose and immediately at the end of infusion on days 1 and 11.

Pharmacodynamic or PARP samples will be collected during cycle 1, pre dose on days 1, 4, 8 and 1. Post dose samples only on day 1.

Sites that are unable to perform the PK or pharmacodynamic sample collection as specified will be permitted to participate in the study, and the protocol will be amended accordingly at those sites.

Efficacy: Tumors will be assessed by standard methods (eg, CT) at baseline and then approximately every 6-8 weeks thereafter in the absence of clinically evident progression of disease.

Statistical Methods

The primary objective of the study is to estimate the clinical benefit rate (CBR) in the BA arm. In each of the two arms, the primary efficacy endpoint (CBR) will be estimated, and the exact binomial 90% confidence interval will be calculated. The CBRs in the two arms will be compared using a one-sided Fisher's exact test at the 5% level of significance. Secondary and exploratory efficacy endpoints of progression-free survival and overall survival will be estimated, and 95% confidence intervals will be calculated using the Kaplan-Meier method. The distributions of progression-free survival and overall survival in the two arms will be compared using the log-rank test. Analyses of PARP inhibition data will be exploratory and descriptive in nature. For the primary safety endpoint, AEs and serious adverse events (SAEs) will be tabulated by study arm, system organ class, and preferred terms. Laboratory test results after the first cycle will be summarized with regard to shifts from baseline values.

Follow-Up: On day 90 and every 90 days (±20 days) after the last dose of study drug follow-up information will be obtained.

Laboratory assessments—Blood and urine samples for hematology, serum chemistry, and urinalysis will be prepared using standard procedures. Laboratory panels are defined as follows:

Hematology: WBC count with differential, RBC count, hemoglobin, hematocrit, and platelet count Serum chemistry: albumin, ALP, ALT, AST, BUN, calcium, carbon dioxide, chloride, creatinine, γ-glutamyl transferase, glucose, lactate dehydrogenase, phosphorus, potassium, sodium, total bilirubin, and total protein Urinalysis: appearance, color, pH, specific gravity, ketones, protein, glucose, bilirubin, nitrite, urobilinogen, and occult blood (microscopic examination of sediment will be performed only if the results of the urinalysis dipstick evaluation are positive)

Pharmacokinetic blood samples will be obtained only from subjects who are enrolled in study arm 2 or who crossover onto study arm 2. Samples will be collected immediately pre dose and immediately at the end of each infusion during cycle 1 on study days 1 and 11.

Biomarkers are objectively measured and evaluated indicators of normal biologic processes, pathogenic processes, or pharmacologic responses to a therapeutic intervention. In oncology, there is particular interest in the molecular changes underlying the oncogenic processes that may identify cancer subtypes, stage disease, assess the amount of tumor growth, or predict disease progression, metastasis, and responses to BA.

The functional activity of PARP before and after treatment of BA will be determined using a PARP activity assay in Peripheral Blood Mononuclear Cells (PBMCs). PBMCs will be prepared from 5 mL blood samples according to procedures described in detail in the study manual and PARP activity/inhibition will be measured.

Refer to the study manual that will be provided to each site for detailed collection, handling, and shipping procedures for all PARP samples.

A breast cancer (BRCA) gene test is a blood test to check for specific changes (mutations) in genes (BRCA1 and BRCA2) that help control normal cell growth. Women who have BRCA mutations have been shown to have between a 36% and 85% chance of developing breast cancer and between a 16% and 60% chance of developing ovarian cancer. Administration of a PARP inhibitor to women with a BRCA mutation may prove to be beneficial. This study is an initial attempt to determine any association between BRCA status and response to treatment with BA.

In order to accomplish this, BRCA status should be determined (if not already known) for all subjects. A subject will need to sign a separate informed consent form. As this is not an inclusion criteria for the study, potential subjects who do not agree to this testing will not be excluded from participating in this study for this reason alone.

In each of the two arms, the primary efficacy endpoint (CBR) will be estimated, and the exact binomial 90% confidence interval will be calculated. The CBRs in the two arms will be compared using a one-sided Fisher's exact test at the 5% level of significance. Secondary and exploratory efficacy endpoints of progression-free survival and overall survival in the two arms will be compared using the log-rank test.

Tumor response data will be reported descriptively as listings for all subjects in the safety population for purposes of determining whether BA treatment has had a measurable clinical effect (e.g. time to progression) and should be continued beyond the first 8 weeks. Response data will be categorized using the modified RECIST.

PARP inhibition analysis will be exploratory as appropriate and descriptive in nature. Statistical group comparisons for differences in PARP inhibition and any pharmacogenomic results (e.g. BRCA) from samples taken before, during and after BA treatment will be considered.

Analyses of safety will be completed for all subjects who receive at least 1 dose of BA.

BA used in the study will be formulated in a 10 mg/mL concentration containing 25% hydroxypropylbetacyclodextrin in a 10 mM phosphate buffer (pH 7.4).

Response Evaluation Criteria in Solid Tumors (RECIST): Eligibility

Only patients with measurable disease at baseline should be included in protocols where objective tumor response is the primary endpoint.

Measurable disease—the presence of at least one measurable lesion. If the measurable disease is restricted to a solitary lesion, its neoplastic nature should be confirmed by cytology/histology.

Measurable lesions—lesions that can be accurately measured in at least one dimension with longest diameter $\geq 20$ mm using conventional techniques or $\geq 10$ mm with spiral CT scan.

Non-measurable lesions—all other lesions, including small lesions (longest diameter <20 mm with conventional techniques or <10 mm with spiral CT scan), i.e., bone lesions, leptomeningeal disease, ascites, pleural/pericardial effusion, inflammatory breast disease, lymphangitis cutis/pulmonis, cystic lesions, and also abdominal masses that are not confirmed and followed by imaging techniques; and.

All measurements should be taken and recorded in metric notation, using a ruler or calipers. All baseline evaluations should be performed as closely as possible to the beginning of treatment and never more than 4 weeks before the beginning of the treatment.

The same method of assessment and the same technique should be used to characterize each identified and reported lesion at baseline and during follow-up.

Clinical lesions will only be considered measurable when they are superficial (e.g., skin nodules and palpable lymph nodes). For the case of skin lesions, documentation by color photography, including a ruler to estimate the size of the lesion, is recommended.

Methods of Measurement

CT and MRI are the best currently available and reproducible methods to measure target lesions selected for response assessment. Conventional CT and MRI should be performed with cuts of 10 mm or less in slice thickness contiguously. Spiral CT should be performed using a 5 mm contiguous reconstruction algorithm. This applies to tumors of the chest, abdomen and pelvis. Head and neck tumors and those of extremities usually require specific protocols.

Lesions on chest X-ray are acceptable as measurable lesions when they are clearly defined and surrounded by aerated lung. However, CT is preferable.

When the primary endpoint of the study is objective response evaluation, ultrasound (US) should not be used to measure tumor lesions. It is, however, a possible alternative to clinical measurements of superficial palpable lymph nodes, subcutaneous lesions and thyroid nodules. US might also be useful to confirm the complete disappearance of superficial lesions usually assessed by clinical examination.

The utilization of endoscopy and laparoscopy for objective tumor evaluation has not yet been fully and widely validated. Their uses in this specific context require sophisticated equipment and a high level of expertise that may only be available in some centers. Therefore, the utilization of such techniques for objective tumor response should be restricted to validation purposes in specialized centers. However, such techniques can be useful in confirming complete pathological response when biopsies are obtained.

Tumor markers alone cannot be used to assess response. If markers are initially above the upper normal limit, they must normalize for a patient to be considered in complete clinical response when all lesions have disappeared.

Cytology and histology can be used to differentiate between PR and CR in rare cases (e.g., after treatment to differentiate between residual benign lesions and residual malignant lesions in tumor types such as germ cell tumors).

Baseline Documentation of "Target" and "Non-Target" Lesions

All measurable lesions up to a maximum of five lesions per organ and 10 lesions in total, representative of all involved organs should be identified as target lesions and recorded and measured at baseline.

Target lesions should be selected on the basis of their size (lesions with the longest diameter) and their suitability for accurate repeated measurements (either by imaging techniques or clinically).

A sum of the longest diameter (LD) for all target lesions will be calculated and reported as the baseline sum LD. The baseline sum LD will be used as reference by which to characterize the objective tumor.

All other lesions (or sites of disease) should be identified as non-target lesions and should also be recorded at baseline. Measurements of these lesions are not required, but the presence or absence of each should be noted throughout follow-up.

Response Criteria

Evaluation of Target Lesions:

Complete Response (CR): Disappearance of all target lesions

Partial Response (PR): At least a 30% decrease in the sum of the LD of target lesions, taking as reference the baseline sum LD Progressive Disease (PD): At least a 20% increase in the sum of the LD of target lesions, taking as reference the smallest sum LD recorded since the treatment started or the appearance of one or more new lesions Stable Disease (SD): Neither sufficient shrinkage to qualify for PR nor sufficient increase to qualify for PD, taking as reference the smallest sum LD since the treatment started Evaluation of Non-Target Lesions:

Complete Response (CR): Disappearance of all non-target lesions and normalization of tumor marker level Incomplete Response/Stable Disease (SD): Persistence of one or more non-target lesion(s) or/and maintenance of tumor marker level above the normal limits Progressive Disease (PD): Appearance of one or more new lesions and/or unequivocal progression of existing non-target lesions (1)

Although a clear progression of "non target" lesions only is exceptional, in such circumstances, the opinion of the treating physician should prevail and the progression status should be confirmed later on by the review panel (or study chair).

Evaluation of Best Overall Response

The best overall response is the best response recorded from the start of the treatment until disease progression/recurrence (taking as reference for PD the smallest measurements recorded since the treatment started). In general, the patient's best response assignment will depend on the achievement of both measurement and confirmation criteria

| Target lesions | Non-Target lesions | New Lesions | Overall response |
| --- | --- | --- | --- |
| CR | CR | No | CR |
| CR | Incomplete response/SD | No | PR |
| PR | Non-PD | No | PR |
| SD | Non-PD | No | SD |
| PD | Any | Yes or No | PD |
| Any | PD | Yes or No | PD |
| Any | Any | Yes | PD |

Patients with a global deterioration of health status requiring discontinuation of treatment without objective evidence of disease progression at that time should be classified as having "symptomatic deterioration." Every effort should be made to document the objective progression even after discontinuation of treatment.

In some circumstances it may be difficult to distinguish residual disease from normal tissue. When the evaluation of complete response depends on this determination, it is recommended that the residual lesion be investigated (fine needle aspirate/biopsy) to confirm the complete response status.

Confirmation

The main goal of confirmation of objective response is to avoid overestimating the response rate observed. In cases where confirmation of response is not feasible, it should be made clear when reporting the outcome of such studies that the responses are not confirmed.

To be assigned a status of PR or CR, changes in tumor measurements must be confirmed by repeat assessments that should be performed no less than 4 weeks after the criteria for response are first met. Longer intervals as determined by the study protocol may also be appropriate.

In the case of SD, follow-up measurements must have met the SD criteria at least once after study entry at a minimum interval (in general, not less than 6-8 weeks) that is defined in the study protocol Duration of Overall Response The duration of overall response is measured from the time measurement criteria are met for CR or PR (whichever status is recorded first) until the first date that recurrence or PD is objectively documented, taking as reference for PD the smallest measurements recorded since the treatment started.

Duration of Stable Disease

SD is measured from the start of the treatment until the criteria for disease progression are met, taking as reference the smallest measurements recorded since the treatment started.

The clinical relevance of the duration of SD varies for different tumor types and grades. Therefore, it is highly recommended that the protocol specify the minimal time interval required between two measurements for determination of SD. This time interval should take into account the expected clinical benefit that such a status may bring to the population under study.

Response Review

For trials where the response rate is the primary endpoint it is strongly recommended that all responses be reviewed by an expert(s) independent of the study at the study's completion. Simultaneous review of the patients' files and radiological images is the best approach.

Reporting of Results

All patients included in the study must be assessed for response to treatment, even if there are major protocol treatment deviations or if they are ineligible. Each patient will be assigned one of the following categories: 1) complete response, 2) partial response, 3) stable disease, 4) progressive disease, 5) early death from malignant disease, 6) early death from toxicity, 7) early death because of other cause, or 9) unknown (not assessable, insufficient data).

All of the patients who met the eligibility criteria should be included in the main analysis of the response rate. Patients in response categories 4-9 should be considered as failing to respond to treatment (disease progression). Thus, an incorrect treatment schedule or drug administration does not result in exclusion from the analysis of the response rate. Precise definitions for categories 4-9 will be protocol specific.

All Conclusions should be Based on all Eligible Patients.

Sub-analyses may then be performed on the basis of a subset of patients, excluding those for whom major protocol deviations have been identified (e.g., early death due to other reasons, early discontinuation of treatment, major protocol violations, etc.). However, these subanalyses may not serve as the basis for drawing conclusions concerning treatment effi cacy, and the reasons for excluding patients from the analysis should be clearly reported.

The 95% confidence intervals should be provided.

Example 6

Treatment of Breast Cancer with BA

Figure 3:
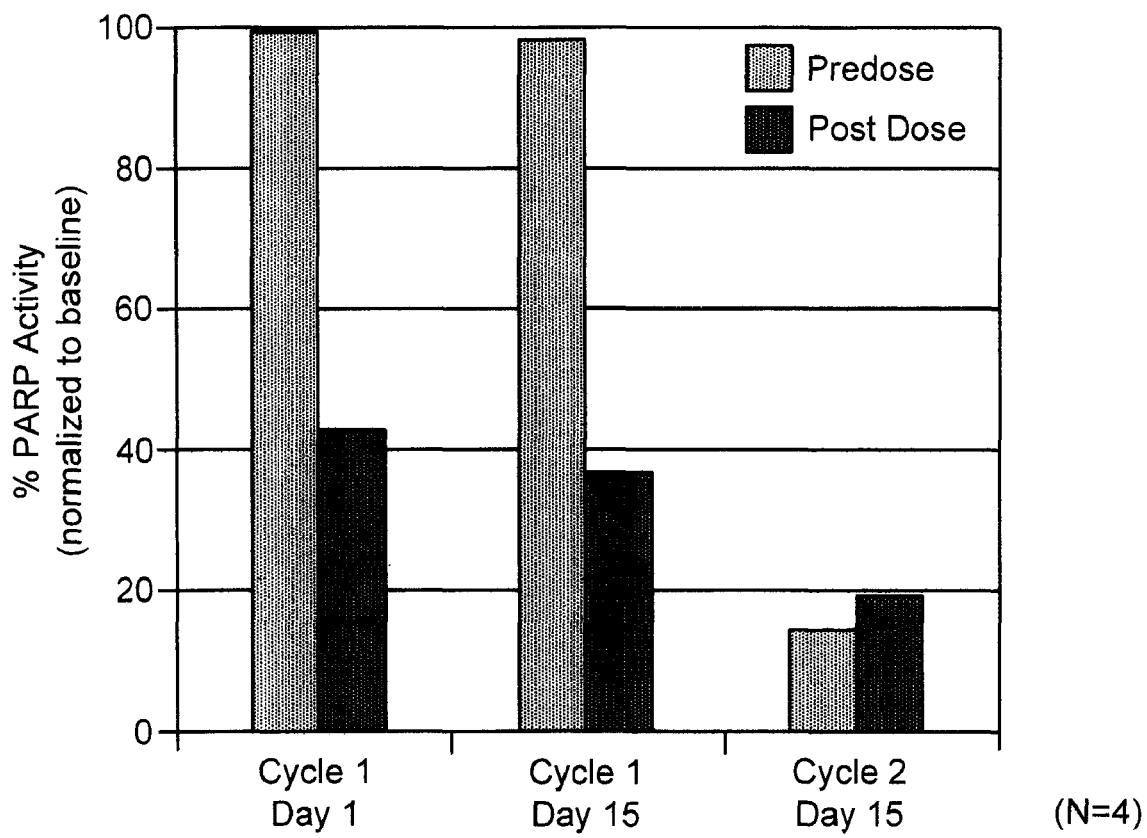
FIG. 3 shows PARP inhibition in peripheral mononuclear blood cells (PMBCs) from patients receiving 4-iodo-3-nitrobenzamide.

A Phase 1b, open-label, dose escalation study evaluates the safety of BA (2.0, 2.8, 4.0, 5.6, 8.0, and 11.2 mg/kg) in combination with chemotherapeutic regimens (topotecan, gemcitabine, temozolomide, and carboplatin+paclitaxel) in subjects with advanced breast tumors. Evaluation of PBMCs from patients shows significant and prolonged PARP inhibition after multiple dosing with BA doses of 2.8 mg/kg or higher (FIG. 3).

A well tolerated combination of BA with each cytotoxic regimen is identified. Any toxicities observed are consistent with known and expected side effects of each chemotherapeutic regimen. There is no evidence that the addition of BA to any tested cytotoxic regimen either potentiates known toxicities or increases the frequency of their expected toxicities. A biologically relevant dose (2.8 mg/kg) that elicits significant and sustained PARP inhibition at effective preclinical blood concentrations is identified. Approximately 80% of subjects demonstrate evidence of stable disease for 2 cycles of treatment or more, indicating potential clinical benefit.

Example 7

Phase 2 Study in Metastatic Triple Negative Breast Cancer (TNBC) with BA Alone or a Combination of BA with Gemcitabine/Carboplatin A Phase 2, open-label, 2-arm randomized, safety and efficacy trial investigates whether inhibiting PARP activity by combining BA with gemcitabine/carboplatin in metastatic TNBC breast cancer patients improves the clinical benefit rate (CBR=CR+PR+SD≧6 months) compared with standard chemotherapy alone. The hypothesis being tested is that the addition of BA to gemcitabine/carboplatin will be associated with a CBR of 60% compared with 45% achieved with gemcitabine/carboplatin alone in subjects with TNBC.

Endpoints

Primary Endpoints
  Clinical Benefit Rate (CBR=CR+PR+SD≧6 months)
  Safety and tolerability of BA
Secondary Endpoints
  Overall Response Rate (ORR)
  Progression-free survival (PFS)
Exploratory Endpoints
  Characterization of PARP gene expression and pharmacogenomics in archived tumor tissues samples
  BRCA status
  Response in subjects with cancer and known BRCA mutations compared to subjects without these mutations
  Classification of breast tissue as either basal or luminal
Dose/Schedule Subjects are randomized in a 1:1 ratio to either:
  Trial Arm 1: Gemcitabine (1000 mg/m$^2$; 30-min IV infusion)+Carboplatin (AUC 2; 60-min IV infusion) on days 1 and 8 of a 21-day cycle
  Trial Arm 2: Gemcitabine (1000 mg/m$^2$; 30-min IV infusion)+Carboplatin (AUC 2; 60-mm IV infusion) on days 1 and 8+BA (5.6 mg/kg 1-hr IV infusion) on days 1, 4, 8, and 11 of a 21-day cycle All dosing cycles are repeated every 21 days.

Subjects randomized to trial arm 2 are discontinued from the trial upon disease progression. Subjects randomized to trial arm I are allowed to crossover to receive BA in combination with gemcitabine/carboplatin upon disease progression.

Key Eligibility Criteria
  Metastatic breast cancer (Stage 1V) with measurable disease by RECIST
  0-2 prior chemotherapy regimens in the metastatic setting; prior adjuvant/neoadjuvant therapy allowed
  Histologically documented (either primary or metastatic site) breast cancer that is ER-negative, PR-negative, and HER-2 non-overexpressing by immunohistochemistry (0, 1) or non-gene amplification by FISH
  ECOG 0-1

Study Population 85 patients have been enrolled at 23 study sites to date (Table 5).

TABLE 5

Phase II Study Patient Demographics

|  |  | Arm A: Gemcitabine/ Carboplatin | Arm B: BSI-201 + Gemcitabine/ Carboplatin |
|---|---|---|---|
| n |  | 43 | 42 |
| Age (yrs), median (range) |  | 51 (32-80) | 54 (35-68) |
| Gender | Male | 0 (0%) | 0 (0%) |
|  | Female | 43 (100%) | 42 (100%) |
| Race | White | 29 (67%) | 32 (76%) |
|  | Black | 8 (19%) | 6 (14%) |
|  | Unknown | 6 (14%) | 4 (10%) |
| # prior chemotherapy regimens* | Neoadjuvant | 5 | 4 |
|  | 0 | 5 | 3 |
|  | 1 | 18 | 13 |
|  | 2 | 7 | 13 |
|  | 3 | 1 | 0 |

*based on available daia

ER, PR, and HER2 Expression Profiling

Inclusion into the study is based on traditional histologic testing at study site. Paraffin embedded sections of original biopsied tissue are obtained from patients enrolled in the trial and characterized the status of genes that are markers of TNBC including ER, PR, HER2, as well as PARP1, Top2A, and Ki-67. The method is based on optimized multiplex quantitative RT-PCR for quantitative assessment of gene expression in formalin-fixed and paraffin-embedded (FFPE) tissue. The clinical trial samples are compared to independently obtained control samples that represent FFPE normal and tumor tissues. In addition, a number of samples are obtained from patients who are documented HER2 overexpressors.

Tissue Samples

Specimens are harvested as part of a normal surgical procedure and flash frozen within 30 minutes of resection. Internal pathology review and confirmation are performed on samples subjected to analysis. Hematoxylin and eosin (H&E)-stained glass slides generated from adjacent tissues are used to confirm and classify diagnostic categories and to evaluate neoplastic cellularity. Expression of ER, PR, and HER2 is determined using immunohistochemistry and fluorescence in silt hybridization. These results, as well as attendant pathology and clinical data, are annotated with sample inventory and management databases (Ascenta, BioExpress databases; GeneLogic, Inc., Gaithersburg, Md.).

RNA Extraction and Expression Profiling

RNA extraction and hybridization are performed as described by Hansel et al. Array data quality is evaluated using array high throughput application (Ascenta, Bioexpress Gene Logic, Gaithersburg Md. and Affymetrix, Santa Clara, Calif.), which assesses the data against multiple objective standards including 5'/3' GAPDH ratio, signal/noise ratio, and background as well as other additional metrics. Gene-Chip analysis is performed with Affymetrix Microarray Analysis Suite version 5.0, Data Mining Tool 2.0, and Microarray database software (Affymetrix, Santa Clara, Calif.). All of the genes represented on the GeneChip are globally normalized and scaled to a signal intensity of 100.

Microarray Data Analysis

Pathologically normal tissue samples are used to determine baseline expression of the PARP1 mRNA. The mean and 90%, 95%, 99%, and 99.9% upper confidence limits (UCLs) for an individual predicted value are calculated. Because we are assessing the likelihood that individual samples external to the normal set are within the baseline distribution, the prediction interval, rather than the confidence interval for the mean, is selected to estimate the expected range for future individual measurements. The prediction interval is defined by the formula, $\bar{X} \pm AS\sqrt{1+(1/n)}$, where $\bar{X}$ is the mean of the normal breast samples, S is the standard deviation, n is the sample size, and A is the $100(1-(p/2))^{th}$ percentile of the Student's t-distribution with n−1 degrees of freedom.

Pathologically normal tissue samples is used to determine baseline expression of the PARP1. Samples are grouped into various subcategories according to characteristics including tumor stage, smoking status, CA125 status, or age. Each tumor sample is evaluated according to 90%, 95%, 99%, or 99.9% UCLs Analysis is performed using SAS v8.2 for Windows (www.sas.com).

Pearson's correlations are calculated for 11 probe sets as compared to PARP1. Correlations are based on the complete set of 194 samples. The Pearson's product-moment correlation is defined by the formula, $$r_{xy} = \frac{\sum (x_i - \bar{x})(y_i - \bar{y})}{\sqrt{\sum (x_i - \bar{x})^2 \sum (y_i - \bar{y})^2}},$$

where $\bar{X}$ is the mean of the PARP1 probe set and $\bar{Y}$ is the mean of the probe set to which PARP1 is being correlated. Statistical significance is determined by the formula, $$\frac{(n-2)^{1/2} r}{(1-r^2)^{1/2}},$$

where r is the correlation and n is the number of samples. The resultant value is assumed to have at distribution with n−2 degrees of freedom.

Multiplex Reverse Transcriptase-Polymerase Chain Reaction (RT-PCR):

Multiplex RT-PCR is performed using 25 ng of total RNA of each sample as previously described (Khan et al., 2007). The multiplex assay used for this study is designed to detect RNA from formalin fixed paraffin embedded (FFPE) samples or from frozen tissues. The concentration of the RNA is determined using the RiboGreen RNA Quantitation Kit (Invitrogen) with Wallac Victo r2 1420 Multilabel Counter. A sample of RNA from each sample is analyzed on an Agilent Bioanalyzer following instructions of Agilent 2100 Bioanalyzer. Reverse transcription (RT) reactions are carried out as previously described with the Applied Biosystems 9700. PCR reactions are carried out on each cDNA with the Applied Biosystems 9700. RT reactions are spiked with Kanamycin RNA to monitor efficiency of the RT and PCR reactions. Controls used included positive control RNA, a no template control, and a no reverse transcriptase control. PCR reactions are analyzed by capillary electrophoresis. The fluorescently labeled PCR reactions are diluted, combined with Genome Lab size standard-400 (Beckman-Coulter,), denatured, and assayed with the CEQ 8800 Genetic Analysis System. The expression of each target gene relative to the expression of β-glucuronidase (GUSB) within the same reaction is reported as the mean and standard deviation of 3 independent assessments for each sample.

Figure 4:
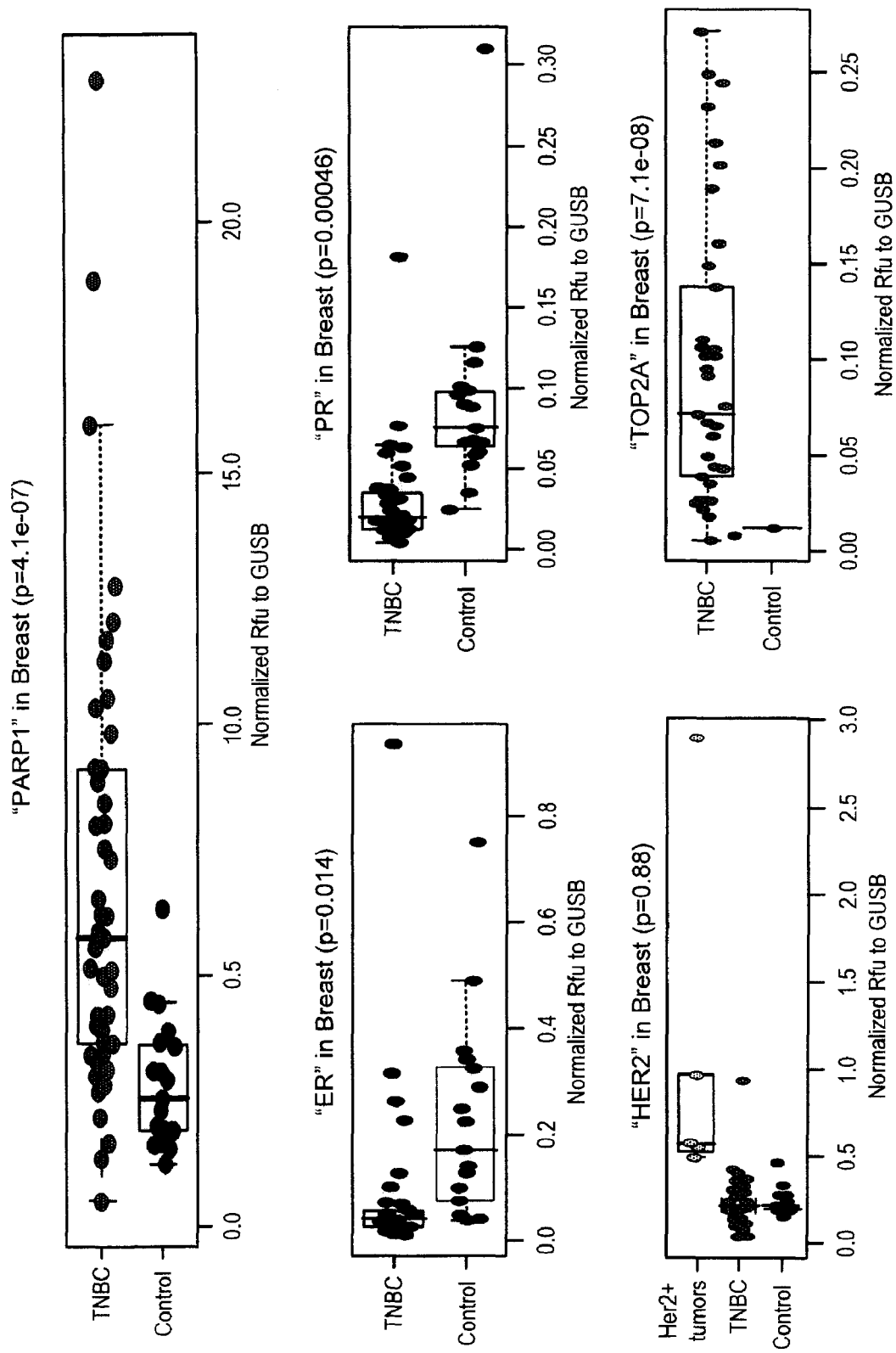
FIG. 4 shows PARP1, ER, PR, and HER2 expression profiling in human breast tumor samples from Phase 2 trial in metastatic TNBC. Data are normalized to beta-glucuronidase gene expression. Data represent the analysis of 50 clinical breast cancer samples and 19 normal breast samples. Vertical line represents median gene expression, and box represents the interquartile range.

FIG. 4 illustrates results for the first 50 patients enrolled in the trial. While the classification of patients as "triple negative" is based on results of ER, PR and HER2 using routine clinical methodology these results show that ER and PR gene expression are both low compared with normal tissue. HER2 expression is comparable to normal and distinct from patients who overexpress PARP1 gene expression is significantly increased confirming our previous observation.

Preliminary Results

Safety

Dose reductions, both in terms of percentage of patients with reductions and total number of reductions, are similar in both groups (Table 6).

TABLE 6

| | Dose Reductions | |
|---|---|---|
| | Arm A: Gemcitabine/ Carboplatin | Arm B: BSI-201 + Gemcitabine/ Carboplatin |
| Patients with dose reductions, n of N (%) | 15/39 (38.5%) | 11/39 (28.2%) |
| Total Reductions | 20 | 19 |

Gemcitabine/carboplatin reductions, as defined by algorithm in protocol

In the chemotherapy only arm, 15 of 39 subjects (38.9%) have dose reductions, and in the BA+chemotherapy arm, 11 of 39 subjects (28.2%) have dose reductions. Overall, there are 20 dose reductions in the gemcitabine/carboplatin group and 19 in the BA+gemcitabine/carboplatin group. Considering there are approximately three times the number of doses given in Arm B compared with Arm A, evidence for the safety of adding BA to gemcitabine/carboplatin is further strengthened.

Evaluation of adverse effects (AEs) shows that the two study arms are comparable (risk ratio=1.0, without correction for overall time in study; Table 7).

TABLE 7

Adverse Effects

| System Organ Class | Arm A (Gemcitabine/Carboplatin) n = 33 | | | | | Arm B (Gem/Carb + BSI-201) n = 23 | | | | |
|---|---|---|---|---|---|---|---|---|---|---|
| | G1 | G2 | G3 | G4 | Total | G1 | G2 | G3 | G4 | Total |
| Blood and lymphatic system disorders | 1 | 3 | 12 | 9 | 25 | 3 | 2 | 11 | 4 | 20 |
| Cardiac disorders | | 2 | | | 2 | 1 | | | | 1 |
| Ear and labyrinth disorders | 1 | | | | 1 | 1 | 1 | | | 2 |
| Endocrine disorders | | | | | 0 | 1 | 1 | | | 2 |
| Eye disorders | 2 | | | | 2 | 5 | | | | 5 |
| Gastrointestinal disorders | 16 | 10 | 1 | | 27 | 14 | 8 | | | 22 |
| General disorders and administration site conditions | 11 | 8 | 4 | | 23 | 11 | 7 | | | 18 |
| Hepatobiliary disorders | 1 | | 1 | | 2 | | 1 | | | 1 |
| Immune system disorders | | 1 | | | 1 | 2 | 1 | | | 3 |
| Infections and infestations | 8 | 6 | | | 14 | 8 | 5 | | | 13 |
| Injury, poisoning and procedural complications | 1 | 3 | | | 4 | 1 | | | | 1 |
| Investigations | 3 | 3 | 1 | | 7 | 4 | 1 | 2 | | 7 |
| Metabolism and nutrition disorders | 10 | 2 | 2 | | 14 | 4 | 1 | | | 5 |
| Musculoskeletal and connective tissue disorders | 9 | 8 | 2 | | 19 | 6 | 1 | 1 | | 8 |
| Neoplasms benign, malignant and unspecified (incl cysts and polyps) | | 1 | | | 1 | | | 1 | | 1 |
| Nervous system disorders | 5 | 6 | 3 | | 14 | 8 | 5 | | | 13 |
| Psychiatric disorders | 5 | 2 | | | 7 | 4 | 2 | | | 6 |
| Renal and urinary disorders | 4 | 2 | | | 6 | 4 | | | | 4 |
| Reproductive system and breast disorders | 2 | | | | 2 | 1 | | | | 1 |
| Respiratory, thoracic and mediastinal disorders | 13 | 5 | 2 | | 20 | 4 | 2 | | | 6 |
| Skin and subcutaneous tissue disorders | 9 | 6 | | | 15 | 7 | 1 | | | 8 |
| Surgical and medical procedures | | | 1 | | 1 | 2 | | | | 2 |
| Vascular disorders | 6 | 2 | | | 8 | 2 | | | | 2 |
| TOTAL | 107 | 70 | 29 | 9 | 215 | 93 | 39 | 15 | 4 | 151 |
| Risk Ratio | | | | | | | | | | 1.0 |

Efficacy

Patients in study arm A (gemcitabine/carboplatin alone) seem to demonstrate progressive disease much earlier than patients randomized to study arm B (gemcitabine/carboplatin+BA). Approximately 50% of subjects in Arm A progress by the end of cycle 2 compared with less than 15% of subjects in Arm B progressing in the same time frame.

Figure 5:
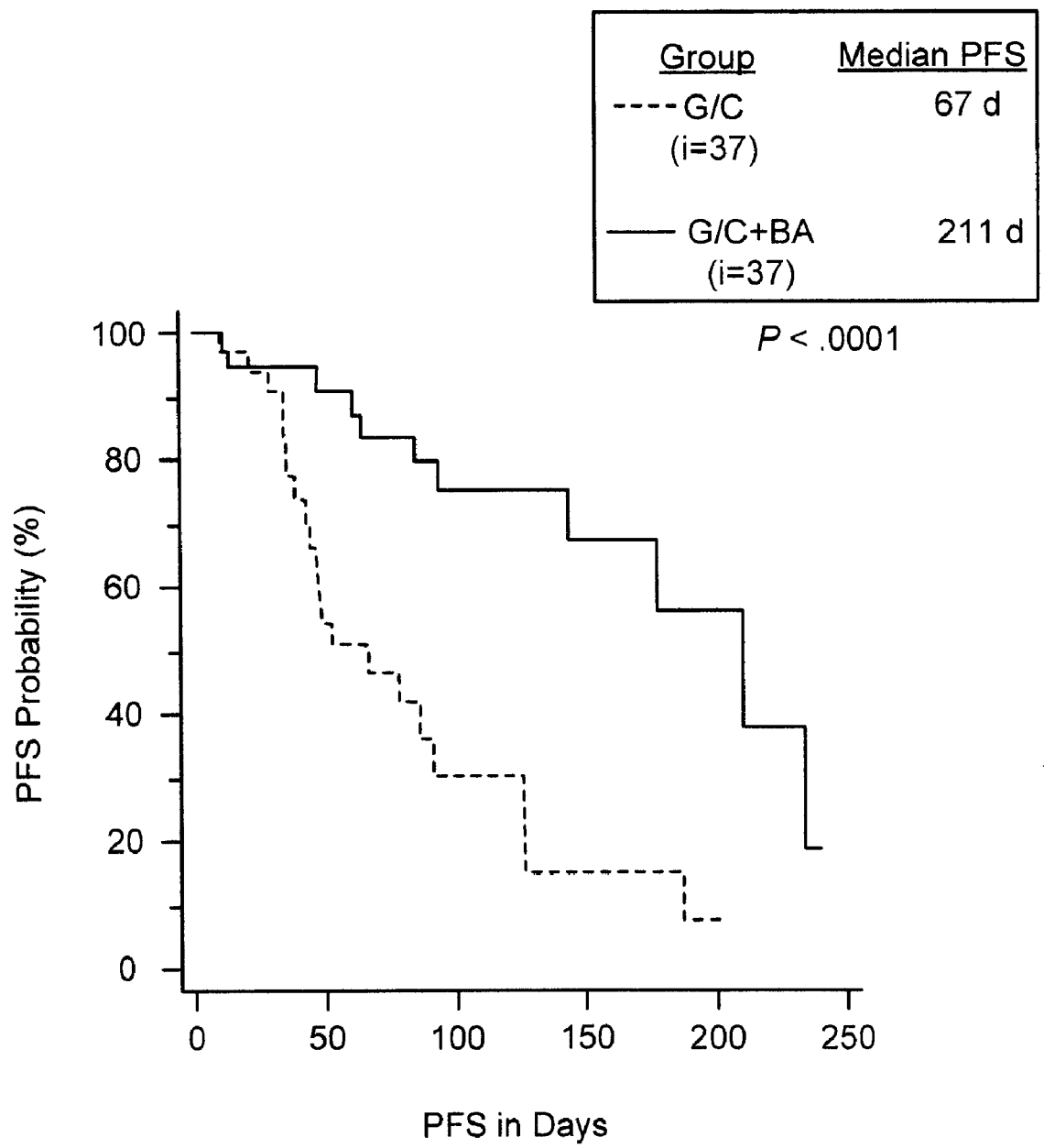
FIG. 5 shows Kaplan-Meier curve of PFS in metastatic TNBC patients receiving 4-iodo-3-nitrobenzamide plus gemcitabine/carboplatin versus gemcitabine/carboplatin alone. The distributions of PFS in the two treatment arms are summarized using the Kaplan-Meier method. The two arms are compared using a 2-sided log-rank test at the 5% level of significance. G/C, gemcitabine/carboplatin; G/C+BA, gemcitabine/carboplatin+4-iodo-3-nitrobenzamide (BA).

A formal statistical analysis is conducted using available preliminary data. This analysis shows that patients who have received BA in combination with gemcitabine/carboplatin have a significantly longer median PFS, compared with patients who have received gemcitabine/carboplatin alone (211 days vs. 67 days; P<0.0001; FIG. 5).

A preliminary assessment of the clinical benefit rate (CBR) is estimated for patients on study for 120 and 180 days (CBR-120 and CBR-180, respectively), and is shown in Table 8.

TABLE 8

Preliminary Assessment of Clinical Effect

| Endpoint | Arm A: Gemcitabine/ Carboplatin | Arm B: Gemcitabine/ Carboplatin + BSI-201 | P |
|---|---|---|---|
| Median PFS | 67 days | 211 days | <.0001 |
| CBR-180[a] | 5/20 (25%) | 10/20 (50%) | 0.1908 |
| CBR-120[b] | 6/20 (30%) | 14/20 (70%) | 0.0256 |

[a]SD (180 days) + PR + CR, for first 40 pts enrolled;
[b]SD (120 days) + PR + CR, for first 40 pts enrolled
Determination of PR includes confirmed and unconfirmed responses.

Results show a trend toward greater CBR in the gemcitabine/carboplatin+BA arm.

Preliminary Study Conclusions

Based on the results presented above, the following conclusions can be reached for the Phase 2 metastatic TNBC study:

Appropriate patients are enrolled. Results from genomic profiling for the initial 50 patients enrolled indicate that these patients are indeed ER- and PR-negative and did not overexpress HER2 using both traditional IHC and gene expression profiling.

The patient population in the two study arms is comparable.

Demographic information shows a similar median age and performance status in each group.

Extent of prior chemotherapeutic treatment in the metastatic setting is similar in both groups. Data from the initial 69 patients show no significant differences in pre-treatment in either study arm. More patients in the BA arm receive 2 courses of prior chemotherapy, suggesting that these subjects are potentially more refractory to chemotherapy than subjects receiving gemcitabine/carboplatin alone.

Dose reductions, both in terms of percentage of patients with reductions and total number of reductions, are similar in both groups. In the chemotherapy only arm, 15 of 39 subjects (38.9%) have dose reductions, and in the BA+chemotherapy arm, 11 of 39 subjects (28.2%) have dose reductions. Overall, there are 20 dose reductions in the gemcitabine/carboplatin group and 19 in the BA+gemcitabine/carboplatin group.

The rate of AEs is similar in both groups, supporting the conclusion that the addition of BA to gemcitabine/carboplatin does not potentiate known toxicities or cause any new toxicities.

Patients who have received BA in combination with gemcitabine/carboplatin show significant clinical benefit over those who have received gemcitabine/carboplatin alone, based on interim analysis of median progression-free survival (211 days vs. 67 days; P<0.0001). These results represent a significant improvement over PFS from other metastatic TNBC studies.

Analysis of clinical benefit rate on the initial 40 patients enrolled shows a trend for improvement upon addition of BA to gemcitabine/carboplatin. This effect is expected to become more robust as the study matures.

Example 8

Treatment of Breast Cancer with a Combination of Paclitaxel, Carboplatin and BA

Patients have triple negative metastatic breast cancer with documented disease progression. Histologic confirmation of the original primary tumor is required.

All patients will have measurable disease. Measurable disease is defined as at least one lesion that can be accurately measured in at least one dimension (longest dimension to be recorded). Each lesion must be ≧20 mm when measured by conventional techniques, including palpation, plain x-ray, CT, and MRI, or ≧10 mm when measured by spiral CT.

Patients will have at least one "target lesion" to be used to assess response on this protocol as defined by RECIST (Section 8.1). Tumors within a previously irradiated field will be designated as "non-target" lesions unless progression is documented or a biopsy is obtained to confirm persistence at least 90 days following completion of radiation therapy. In addition, patients must have recovered from effects of recent surgery, radiotherapy or other therapy, and should be free of active infection requiring antibiotics.

Any hormonal therapy directed at the malignant tumor must be discontinued at least one week prior to registration. Continuation of hormone replacement therapy is permitted.

Patients must have adequate:

Bone marrow function: Platelet count greater than or equal to 100,000/microliter, and ANC count greater than or equal to 1,500/microliter, equivalent to CTCAE v3.0 grade 1.

Renal function: creatinine less than or equal to 1.5× institutional upper limit normal (ULN), CTCAE v3.0 grade 1.

Hepatic function: Bilirubin less than or equal to 1.5×ULN (CTCAE v3.0 grade 1). SGOT and alkaline phosphatase less than or equal to 2.5×ULN (CTCAE v3.0 grade I).

Neurologic function: Neuropathy (sensory and motor) less than or equal to CTCAE v3.0 grade 1.

Patients of childbearing potential must have a negative serum pregnancy test prior to the study entry and be practicing an effective form of contraception.

Ineligible Patients:

Patients who have received prior cytotoxic chemotherapy for management of breast cancer.

Patients with a history of other invasive malignancies, with the exception of non-melanoma skin cancer and other specific malignancies as noted in Sections 3.23 and 3.24 are excluded if there is any evidence of other malignancy being present within the last five years. Patients are also excluded if their previous cancer treatment contraindicates this protocol therapy.

Patients who have received prior radiotherapy to any portion of the abdominal cavity or pelvis OTHER THAN for the treatment of breast cancer within the last five years are excluded. Prior radiation for localized cancer of the breast, head and neck, or skin is permitted, provided that it is completed more than three years prior to registration, and the patient remains free of recurrent or metastatic disease.

Patients MAY have received prior adjuvant chemotherapy for localized breast cancer, provided that it is completed more than three years prior to registration, and that the patient remains free of recurrent or metastatic disease.

Symptomatic or untreated brain metastases requiring concurrent treatment, inclusive of but not limited to surgery, radiation, and corticosteroids.

Myocardial infarction (MI) within 6 months of study day 1, unstable angina, congestive heart failure (CHF) with New York Heart Association (NYHA)>class 11, or uncontrolled hypertension.

History of seizure disorder or currently on anti-seizure medication.

Study Modalities

Carboplatin (Paraplatin®, NSC #241240)

Formulation: Carboplatin is supplied as a sterile lyophilized powder available in single-dose vials containing 50 mg, 150 mg and 450 mg of carboplatin for administration by intravenous infusion. Each vial contains equal parts by weight of carboplatin and mannitol.

Solution Preparation: Immediately before use, the content of each vial must be reconstituted with either sterile water for injection, USP, 5% dextrose in water, or 0.9% sodium chloride injection, USP, according to the following schedule:

| Vial Strength | Diluent Volume |
|---|---|
| 50 mg | 5 ml |
| 150 mg | 15 ml |
| 450 mg | 45 ml |

These dilutions all produce a carboplatin concentration of 10 mg/ml.

NOTE: Aluminum reacts with carboplatin causing precipitate formation and loss of potency. Therefore, needles or intravenous sets containing aluminum parts that may come in contact with the drug must not be used for the preparation or administration of carboplatin.

Storage: Unopened vials of carboplatin are stable for the life indicated on the package when stored at controlled room temperature and protected from light.

Stability: When prepared as directed, carboplatin solutions are stable for eight hours at room temperature. Since no antibacterial preservative is contained in the formulation, it is recommended that carboplatin solutions be discarded eight hours after dilution.

Supplier: Commercially available from Bristol-Myers Squibb Company.

Paclitaxel (Taxol®, NSC #673089)

Formulation: Paclitaxel is a poorly soluble plant product from *Taxus baccata*. Improved solubility requires a mixed solvent system with further dilutions of either 0.9% sodium chloride or 5% dextrose in water.

Paclitaxel is supplied as a sterile solution concentrate, 6 mg/ml in 5 ml vials (30 mg/vial) in polyoxyethylated castor oil (Cremophor EL) 50% and dehydrated alcohol, USP, 50%.

The contents of the vial must be diluted just prior to clinical use. It is also available in 100 and 300 mg vials.

Solution Preparation: Paclitaxel, at the appropriate dose, will be diluted in 500-1000 ml of 0.9% Sodium Chloride injection, USP or 5% Dextrose injection, USP (D5W) (500 ml is adequate if paclitaxel is a single agent). Paclitaxel must be prepared in glass or polyolefin containers due to leaching of diethylhexlphthalate (DEHP) plasticizer from polyvinyl chloride (PVC) bags and intravenous tubing by the Cremophor vehicle in which paclitaxel is solubilized.

NOTE: Formation of a small number of fibers in solution (within acceptable limits established by the USP Particulate Matter Test for LVPs) has been observed after preparation of paclitaxel. Therefore, in-line filtration is necessary for administration of paclitaxel solutions. In-line filtration should be accomplished by incorporating a hydrophilic, microporous filter of pore size not greater than 0.22 microns (e.g.: IVEX-II. IVEX-HP or equivalent) into the IV fluid pathway distal to the infusion pump. Although particulate formation does not indicate loss of drug potency, solutions exhibiting excessive particulate matter formation should not be used.

Storage: The intact vials can be stored in a temperature range between 20-25° C. (36-77° F.) in the original package. Freezing or refrigeration will not adversely affect the stability of the product.

Stability: All solutions of paclitaxel exhibit a slight haziness directly proportional to the concentration of drug and the time elapsed after preparation, although when prepared as described above, solutions of paclitaxel (0.3-1.2 mg/mL) are physically and chemically stable for 27 hours at ambient temperature (approximately 25° C.) and room lighting conditions.

Supplier: Commercially available from Bristol-Myers Squibb Company.

Administration: Paclitaxel, at the appropriate dose and dilution, will be given as a 3-hour continuous IV infusion. Paclitaxel will be administered via an infusion control device (pump) using non-PVC tubing and connectors, such as the IV administration sets (polyethylene or polyolefin) that are used to infuse parenteral Nitroglycerin. Nothing else is to be infused through the line where paclitaxel is being administered. See section 5.2.

BA (4-Iodo-3-Nitrobenzamide)

BA will be manufactured and packaged on behalf of BiPar Sciences and distributed using BiPar-approved clinical study drug distribution procedures. BA will be presented as a liquid sterile product in 10 mL single-entry vials. BA is formulated in 25% hydroxypropylbetacyclodextrin/10 mM phosphate buffer, pH 7.4 with an active ingredient concentration of 10 mg/mL. Each vial contains not less than 9.0 mL of extractable volume. Information presented on the labels for the study drug will comply with ICH requirements and those of the US Food and Drug Administration (FDA). Bulk vials of BA will be shipped in cartons of 10 vials per carton and will be labeled with a one-part label. The label will contain the following information: The U.S. cautionary statement for investigational drugs, study number, product name, concentration, storage, retest date, and the name of the study sponsor.

Solution Preparation: BA will be prepared as described below and administered intravenously over a one-hour period:

Calculate the amount (4 mg/kg) of BA required for dosing by using the subject's baseline weight multiplied by the dose level. For example Subject baseline weight=70 kg Dose=4 mg/kg Required dose=(4 mg/kg×70 kg)=280 mg BA Divide the dose of BA needed by the BA concentration in the vial (10 mg/mL) to determine the quantity in mL of BA drug product required for administration. Example:

280 mg÷10 mg/mL=28 mL

Calculate the number of vials of BA at 10 mL per vial to obtain the required volume. (Using this example, 3 vials would be needed.) An additional vial may be used if needed to obtain the needed volume of BA.

Withdraw by syringe the appropriate volume of BA drug product from the vial and set it aside while preparing the IV bag as follows:

It is recommended that a total of 250 mL of solution be in the IV bag and delivered over a one hour period. Use an IV solution of either 0.9% NS or D5W. If starting with an IV bag containing greater than 250 mL of solution, remove and discard the excess solution plus the total volume of drug product to be added to the solution. Inject the calculated volume of BA drug product into the IV bag and ensure adequate mixing. Attach the IV tubing and prime it with the solution. Note: It is acceptable to use an empty IV bag and inject the BA volume as calculated, and then add the 0.9% NS or 5DW to reach a total volume of 250 mL. This would likely be useful for BA volumes of greater than 50 mL.

Storage: The BA drug product vials must be stored at 2-8° C. and protected from light. Keep the drug product vials in the original carton and place in a 2-8° C. temperature-controlled unit. BA may be stored at 25° C. for as long as 24 hours as needed. If BA is determined to have not been handled under these storage conditions, please contact BiPar immediately. Do not use vials that have not been stored at the recommended storage conditions without authorization from BiPar.

Stability: Administer BA within 8 hours after preparation. The dosing solution should be kept at ambient (room) temperature until administered to a study subject.

Supplier: BiPar Sciences Inc.

Treatment Plan

Paclitaxel 175 mg/m$^2$ as a three-hour infusion followed by Carboplatin dosed to an AUC=6.0 over 30 minutes, on Day 1, every 21 days plus BA 4 mg/kg IV over a one hour infusion period twice weekly beginning on Day 1 (doses of BA must be separated by at least 2 days) until disease progression or adverse affects limit further therapy. This three-week period of time is considered one treatment cycle. Number of cycles beyond complete clinical response will be at the discretion of the treating physician. Patients not meeting the criteria for progression of disease (partial response or stable disease) should be continued on study treatment until limited by toxicity.

Dosing of Carboplatin: The dose will be calculated to reach a target area under the curve (AUC) of concentration x time according to the Calvert formula using an estimated glomerular filtration rate (GFR) from the Jelliffe formula. The initial dose will be AUC=6 infused over 30 minutes.

The initial dose of carboplatin must be calculated using GFR. In the absence of new renal obstruction or other renal toxicity greater than or equal to CTCAE v3.0 grade 2 (serum creatinine>1.5×ULN), the dose of carboplatin will not be recalculated for subsequent cycles, but will be subject to dose modification as noted.

In patients with an abnormally low serum creatinine (less than or equal to 0.6 mg/dl), due to reduced protein intake and/or low muscle mass, the creatinine clearance should be estimated using a minimum value of 0.6 mg/dl. If a more appropriate baseline creatinine value is available within 4 weeks of treatment that may also be used for the initial estimation of GFR.

Calvert Formula: Carboplatin dose (mg)=target AUC×(GFR+25).

For the purposes of this protocol, the GFR is considered to be equivalent to the creatinine clearance. The creatinine clearance (Ccr) is estimated by the method of Jelliffe using the following formula: {98−[0.8 (age−20)]} Ccr=0.9×Scr Where: Ccr=estimated creatinine clearance in ml/min; Age=patient's age in years (from 20-80); Scr=serum creatinine in mg/dl. In the absence of new renal obstruction or elevation of serum creatinine above 1.5×ULN (CTCAE v3.0 grade 2), the dose of carboplatin will not be recalculated for subsequent cycles, but will be subject to dose modification for hematologic criteria and other events as noted.

Suggested Method of Chemotherapy Administration: The regimen can be administered in an outpatient setting. Paclitaxel will be administered in a 3-hour infusion followed by carboplatin over 30 minutes, followed by BA over one hour. BA % will be administered intravenously (as an infusion over a time period of one hour) twice weekly for the duration of the study. Doses of BA must be separated by at least 2 days (for example doses can be given on Monday/Thursday, Monday/Friday, or Tuesday/Friday). An antiemetics regimen is recommended for day 1 treatment with paclitaxel and carboplatin treatment. The antiemetics regimen used should be based on peer-reviewed consensus guidelines. Prophylactic antiemetics are not needed for BA doses given alone.

Preparative Regimen for Paclitaxel: Paclitaxel will be administered as a 3-hour infusion on this study. For all cycles where paclitaxel is to be administered, it is recommended that a preparative regimen be employed to reduce the risk associated with hypersensitivity reactions. This regimen should include dexamethasone (either IV or PO), anti-histamine H1 (such as diphenhydramine) and anti-histamine H2 (such as cimetidine, ranitidine, or famotidine.)

Maximum body surface area used for dose calculations will be 2.0 m².

If side effects are not severe, a patient may remain on a study agent indefinitely at the investigator's discretion. Patients achieving a complete clinical response may be continued for additional cycles at the discretion of the treating physician.

Evaluation Criteria

Parameters of Response—RECIST Criteria

Measurable disease is defined as at least one lesion that can be accurately measured in at least one dimension (longest dimension to be recorded). Each lesion must be ≧20 mm when measured by conventional techniques, including palpation, plain x-ray, CT, and MRI, or ≧10 mm when measured by spiral CT.

Baseline documentation of "Target" and "Non-Target" lesions

All measurable lesions up to a maximum of 5 lesions per organ and 10 lesions in total representative of all involved organs should be identified as target lesions and will be recorded and measured at baseline. Target lesions should be selected on the basis of their size (lesions with the longest dimension) and their suitability for accurate repetitive measurements by one consistent method of assessment (either by imaging techniques or clinically). A sum of the longest dimension (LD) for all target lesions will be calculated and reported as the baseline sum LD. The baseline sum LD will be used as reference to further characterize the objective tumor response of the measurable dimension of the disease.

All other lesions (or sites of disease) should be identified as non-target lesions and should also be recorded at baseline. Measurements are not required and these lesions should be followed as "present" or "absent".

All baseline evaluations of disease status should be performed as close as possible to the start of treatment and never more than 4 weeks before the beginning of treatment.

Best Response

Measurement of the longest dimension of each lesion size is required for follow up. Change in the sum of these dimensions affords some estimate of change in tumor size and hence therapeutic efficacy. All disease must be assessed using the same technique as baseline. Reporting of these changes in an individual case should be in terms of the best response achieved by that case since entering the study.

Complete Response (CR) is disappearance of all target and non-target lesions and no evidence of new lesions documented by two disease assessments at least 4 weeks apart.

Partial Response (PR) is at least a 30% decrease in the sum of longest dimensions (LD) of all target measurable lesions taking as reference the baseline sum of LD. There can be no unequivocal progression of non-target lesions and no new lesions. Documentation by two disease assessments at least 4 weeks apart is required. In the case where the ONLY target lesion is a solitary pelvic mass measured by physical exam, which is not radiographically measurable, a 50% decrease in the LD is required.

Increasing Disease is at least a 20% increase in the sum of LD of target lesions taking as references the smallest sum LD or the appearance of new lesions within 8 weeks of study entry. Unequivocal progression of existing non-target lesions, other than pleural effusions without cytological proof of neoplastic origin, in the opinion of the treating physician within 8 weeks of study entry is also considered increasing disease (in this circumstance an explanation must be provided). In the case where the ONLY target lesion is a solitary pelvic mass measured by physical exam, which is not radiographically measurable, a 50% increase in the LD is required.

Symptomatic deterioration is defined as a global deterioration in health status attributable to the disease requiring a change in therapy without objective evidence of progression.

Stable Disease is any condition not meeting the above criteria.

Inevaluable for response is defined as having no repeat tumor assessments following initiation of study therapy for reasons unrelated to symptoms or signs of disease.

Progression (measurable disease studies) is defined as ANY of the following:

At least a 20% increase in the sum of LD target lesions taking as reference the smallest sum LD recorded since study entry In the case where the ONLY target lesion is a solitary pelvic mass measured by physical exam which is not radiographically measurable, a 50% increase in the LD is required taking as reference the smallest LD recorded since study entry The appearance of one or more new lesions Death due to disease without prior objective documentation of progression Global deterioration in health status attributable to the disease requiring a change in therapy without objective evidence of progression Unequivocal progression of existing non-target lesions, other than pleural effusions without cytological proof of neoplastic origin, in the opinion of the treating physician (in this circumstance an explanation must be provided)

Recurrence (non-measurable disease studies) is defined as increasing clinical, radiological or histological evidence of disease since study entry.

Survival is the observed length of life from entry into the study to death or the date of last contact.

Progression-Free Survival (measurable disease studies) is the period from study entry until disease progression, death or date of last contact.

Recurrence-Free Survival (non-measurable disease studies) is the period from study entry until disease recurrence, death or date of last contact.

Subjective Parameters including performance status, specific symptoms, and side effects are graded according to the CTCAE v3.0.

Duration of Study Patients will receive therapy until disease progression or intolerable toxicity intervenes. The patient can refuse the study treatment at any time. Patients with complete clinical response to therapy will be continued on therapy with additional numbers of cycles at the treating physician's discretion. Patients with partial response or stable disease should be continued on therapy unless intolerable toxicity prohibits further therapy.

All patients will be treated (with completion of all required case report forms) until disease progression or study withdrawal. Patients will then be followed (with physical exams and histories) every three months for the first two years and then every six months for the next three years. Patients will be monitored for delayed toxicity and survival for this 5-year period with Q forms submitted to the GOG Statistical and Data Center, unless consent is withdrawn.

Example 9

Combination of 4-iodo-3-nitrobenzamide (BA) with Gamma Irradiation

Triple negative breast cancer cells MDA-MB-468 are obtained from ATCC and cultured in Dulbecco Modified Eagle Medium with 10% fetal bovine serum. Cells are plated at $10^5$ cells per P100 cell culture dish or at $10^4$ cells per P60 cell culture dish in the presence of different concentrations compounds or DMSO control. Following treatment, the number of attached cells is measured using Coulter counter, and by staining with 1% methylene blue. Methylene blue is dissolved in 50%-50% mixture of Methanol and water. Cells are plated in 24- or 96-well plates and treated as planned, media are aspirated, cells are washed with PBS, fixed in methanol for 5-10 min, methanol is aspirated and plates are allowed to dry completely. Methylene blue solution is added to wells and plates are incubated for 5 min. Staining solution is removed and plates are washed with dH2O until washes are no longer blue. After plates are completely dry, a small amount of 1N HCl is added to each well to extract the methylene blue. The OD readout at 600 nm and a calibration curve are used to determine cell number.

BA compounds are dissolved directly from dry powder to 10 mM stock solution in DMSO for each separate experiment. Control experiments are carried out with the matching volume/concentration of the vehicle (DMSO); in these controls, the cells show no changes in their growth or cell cycle distribution.

PI exclusion, cell cycle, TUNEL assays, and BrdU labeling assays are performed as described above in Example 2.

Figure 6:
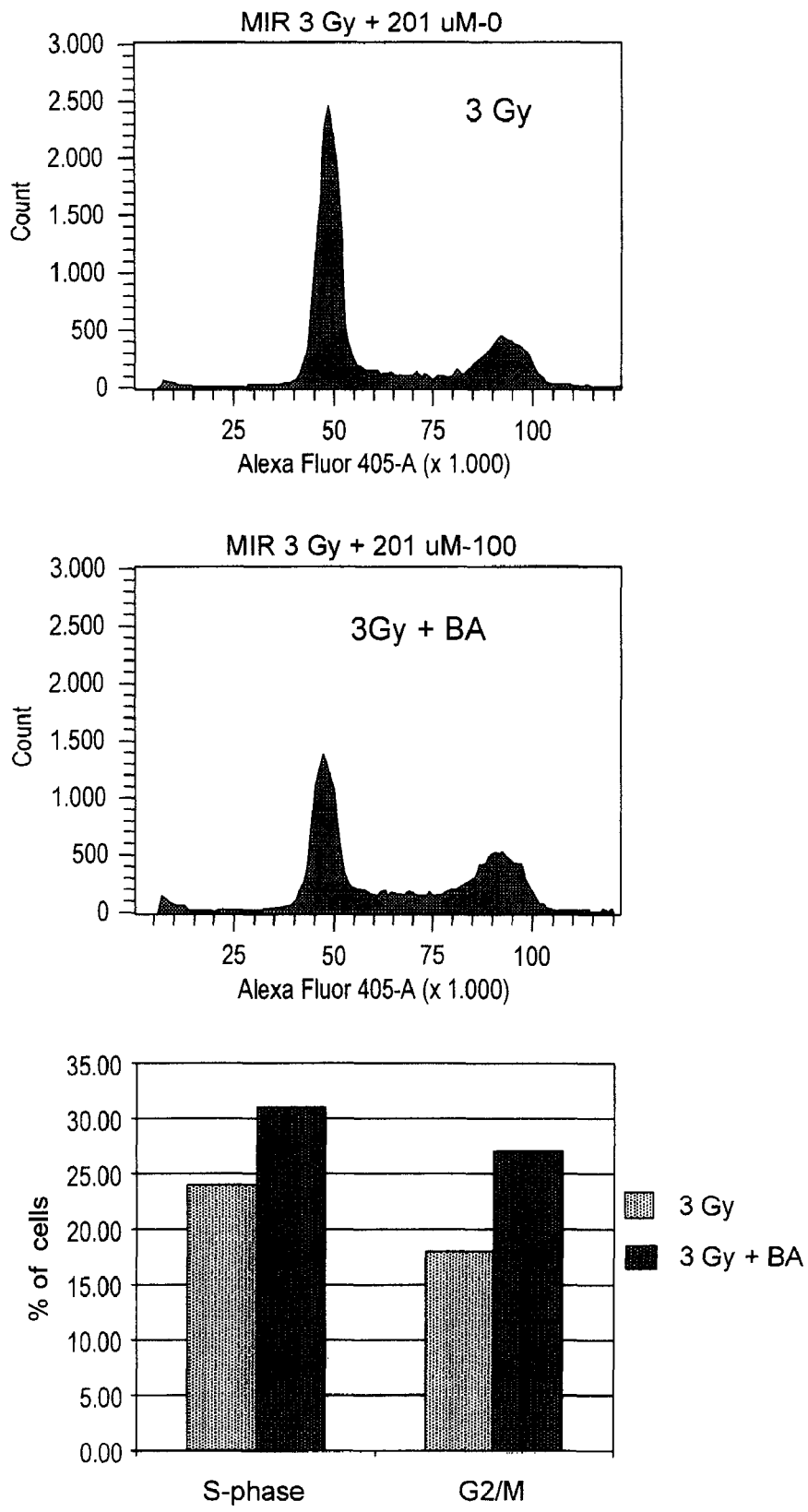
FIG. 6 shows that 4-iodo-3-nitrobenzamide (BA) potentiates S- and G2/M cell cycle arrest and enhances the antiproliferative effect of gamma irradiation in human triple negative breast MDA-MB-468 cancer cells.

MDA-MB-468 cancer cells are treated with 3 gray of gamma irradiation with or without 100 µM of BA. As shown in FIG. 6, BA potentiates S- and G2/M cell cycle arrest and enhances the antiproliferative effect of gamma irradiation in human triple negative breast MDA-MB-468 cancer cells.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating breast cancer that is negative for estrogen receptor ("ER"), progesterone receptor ("PR"), and human epidermal growth factor 2 receptor ("HER2") in a patient, comprising administering to the patient having breast cancer that is negative for ER, PR and HER2 an effective amount of 4-iodo-3-nitrobenzamide or a metabolite or a pharmaceutically acceptable salt thereof, gemcitabine, and carboplatin.

2. The method of claim 1, wherein the effective amount produces at least one therapeutic effect selected from the group consisting of reduction in size of a breast tumor, reduction in metastasis, complete remission, partial remission, stable disease, or a pathologic complete response.

3. The method of claim 1, wherein a comparable clinical benefit rate (CBR=CR (complete remission)+PR (partial remission)+SD (stable disease)≧6 months) is obtained as compared to treatment with said gemcitabine and said carboplatin administered without 4-iodo-3-nitrobenzamide.

4. The method of claim 3, wherein the improvement of clinical benefit rate is about 60% or higher.

5. The method of claim 1, wherein the breast cancer is at stage I, stage II, or stage III.

6. The method of claim 1, further comprising surgery, radiation therapy, chemotherapy, gene therapy, DNA therapy, viral therapy, RNA therapy, DNA therapy, adjuvant therapy, neoadjuvant therapy, immunotherapy, nanotherapy or a combination thereof.

7. The method of claim 1, further comprising administering to the patient gamma irradiation.

8. The method of claim 1, wherein said breast cancer is an infiltrating duct carcinoma.

9. The method of claim 1, wherein said breast cancer is metastatic.

10. The method of claim 1, wherein an effective amount of 4-iodo-3-nitrobenzamide or a pharmaceutically acceptable salt thereof is administered.

* * * * *

UNITED STATES PATENT AND TRADEMARK OFFICE
CERTIFICATE OF CORRECTION

PATENT NO. : 7,732,491 B2
APPLICATION NO. : 12/269024
DATED : June 8, 2010
INVENTOR(S) : Sherman et al.

It is certified that error appears in the above-identified patent and that said Letters Patent is hereby corrected as shown below:

In the Specification:

- At column 6, line number 16, please replace "1, 4, 8 and 1" with --1, 4, 8 and 11--

- At column 24, line number 16, please replace "interferon a from" with --interferon α from--

- At column 25, line numbers 14-15, please replace "Arabino- sylcvtosine," with --Arabinosyl- cytosine,--

- At column 25, line number 46, please replace "Hexylen" with --Hexalen--

- At column 26, line number 3, please replace "Orapred." with --Orapred,--

- At column 26, line number 10, please replace "Revilmid," with --Revlimid,--

- At column 26, line number 14, please replace "SUI 1248" with --SU 11248--

- At column 31, line number 44, please replace "B1-6C9" with --BI-6C9--

- At column 33, line number 37, please replace "form." with --form,--

- At column 56, line number 8, please replace "variation. RT" with --variation, RT--

- At column 57, line number 34, please replace "noassay's" with --noassays--

- At column 62, line number 4, please replace "ER." with --ER,--

- At column 62, line number 6, please replace "in sill" with --in situ--

- At column 62, line number 66, please replace "have at distribution" with -- have a t distribution--

Signed and Sealed this
Thirty-first Day of May, 2011

David J. Kappos
*Director of the United States Patent and Trademark Office*

CERTIFICATE OF CORRECTION (continued)
U.S. Pat. No. 7,732,491 B2

- At column 76, line number 64, please replace "in silt" with --in situ--

- At column 77, line number 58, please replace "have at distribution" with --have a t distribution--

- At column 85, line number 28, please replace "BA%" with --BA--

- At column 85, line number 33, please replace "An antiemetics" with --An antiemetic--

- At column 85, line number 35, please replace "The antiemetics" with --The antiemetic--

- At column 87, line number 25, please replace "Duration of Study Patients will receive therapy until dis-" with a header and paragraph
  --Duration of Study
  Patients will receive therapy until dis- --

In the Claims:

- At column 88, claim number 6, line number 50, please delete "DNA therapy"

Disclaimer

7,732,491 B2 — Barry M. Sherman, Hillsborough, CA (US); Charles Bradley, Half Moon Bay, CA (US); Valeria S. Ossovskaya, San Francisco, CA (US), TREATMENT OF BREAST CANCER WITH A PARP INHIBITOR ALONE OR IN COMBINATION WITH ANTI-TUMOR AGENTS. Patented date June 8, 2010. Disclaimer filed December 19, 2013 by the Assignee, BiPar Sciences, Inc.

Hereby enter this disclaimer to the entire term of said patent.

*(Official Gazette, April 1, 2014)*